United States Patent
Parks et al.

(10) Patent No.: US 12,305,190 B2
(45) Date of Patent: *May 20, 2025

(54) VESICULAR STOMATITIS VIRUS AND VIRUS RESCUE SYSTEM

(71) Applicant: INTERNATIONAL AIDS VACCINE INITIATIVE, INC., New York, NY (US)

(72) Inventors: Christopher L. Parks, Boonton, NJ (US); Maoli Yuan, Brooklyn, NY (US); Kevin Wright, Brooklyn, NY (US); Christy Jurgens, Rahway, NJ (US)

(73) Assignee: INTERNATIONAL AIDS VACCINE INITIATIVE, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/318,325

(22) Filed: May 16, 2023

(65) Prior Publication Data

US 2023/0340535 A1    Oct. 26, 2023

Related U.S. Application Data

(63) Continuation of application No. 16/717,360, filed on Dec. 17, 2019, now Pat. No. 11,667,930, which is a continuation of application No. 15/417,256, filed on Jan. 27, 2017, now Pat. No. 10,544,430, which is a continuation of application No. 13/623,437, filed on Sep. 20, 2012, now abandoned.

(60) Provisional application No. 61/537,497, filed on Sep. 21, 2011.

(51) Int. Cl.
 *C12N 15/86* (2006.01)
 *C12N 7/00* (2006.01)

(52) U.S. Cl.
 CPC ............... *C12N 15/86* (2013.01); *C12N 7/00* (2013.01); *C12N 2760/20221* (2013.01); *C12N 2760/20243* (2013.01); *C12N 2800/22* (2013.01)

(58) Field of Classification Search
 None
 See application file for complete search history.

(56) References Cited

U.S. PATENT DOCUMENTS

2008/0286848 A1   11/2008   Skiadopoulos et al.

OTHER PUBLICATIONS

Gen Bank: EF197793.1. Vesicular stomatitis Indiana virus, complete genome. Dated Apr. 15, 2007.
Gen Bank: AF473864.1. Vesicular stomatitis Indiana virus strain 98COE, complete genome. dated Sep. 24, 2002.
Baklanov, et al., Effect on DNA transcription of nucleotide sequences upstream to T7 promoter', Nucleic Acids Research (1996) 24(18):3659-3660.
Chowrira, et al., In Vitro and in Vivo Comparison on Hammerhead, Hairpin, and Hepatitis Delta Virus Self-Processing Ribozyme Cassettes, The Journal of Biological Chemistry (1994) 269(41):25856-25864.
Inoue, et al., An Improved Method for Recovering Rabies Virus from Cloned cDNA, Journal of Virological Methods (2003) 107:229-236.
Kenny et al., The cysteine knot of platelet glycoprotein Ibb (GPIbb) is critical for the interaction of GPIb with GPIX. Blood. 2002;99: 4428-4433.
Lopez, et al., The Low Processivity of T7 Rna Polymerase Over the Initially Transcribed Sequence Can Limit Productive Initiation in Vivo, J. Mol. Biol. (1997) 269:41-51.
Ternette, et al., Expression of RNA Virus Proteins by RNA Polymerase II Dependent Expression Plasmids is Hindered at Multiple Steps, Virology Journal (2007) 4:51.
Witko, et al., An Efficient Helper-Virus-Free Method for Rescue of Recombinant Paramyxoviruses and Rhadoviruses From a Cell Line Suitable for Vaccine Development, Journal of Virological Methods (2006) 135:91-101.
Gen Bank: X65332.2, Cloning vector pSP72, Dated Jan. 25, 2000.

*Primary Examiner* — Nianxiang Zou
(74) *Attorney, Agent, or Firm* — Duane Morris LLP; Thomas J. Kowalski

(57) ABSTRACT

The present relation relates to recombinant vesicular stomatitis virus for use as prophylactic and therapeutic vaccines as well as the preparation and purification of immunogenic compositions which are formulated into the vaccines of the present invention.

18 Claims, 17 Drawing Sheets
Specification includes a Sequence Listing.

GENOME FRAGMENT VSV-A/G (1489 bp)
atagtcgagacgACGAAGACAAACAAACCATTATTATCATTAAAAGGCTC
AGGAGAAACTTTAACAGTAATCAAATGTCTGTTACAGTCAAGAGAATCA
TTGACAACACAGTCATAGTTCCAAAACTTCCTGCAAATGAGGATCCAGTG
GAATACCCGGCAGATTACTTCAGAAAATCAAAGGAGATTCCTCTTTACAT
CAATACTACAAAAAGTTTGTCAGATCTAAGAGGATATGTCTACCAAGGCC
TCAAATCCGGAAATGTATCAATCATACATGTCAACAGCTACTTGTATGGA
GCATTGAAGGACATCCGGGGTAAGTTGGATAAAGATTGGTCAAGTTTCGG
AATAAACATCGGGAAGGCAGGGGATACAATCGGAATATTTGACCTTGTAT
CCTTGAAAGCCCTGGACGGTGTACTTCCAGATGGAGTATCGGATGCTTCC
AGAACCAGCGCAGATGACAAATGGTTGCCTTTGTATCTACTTGGCTTATA
CAGAGTGGGCAGAACACAAATGCCTGAATACAGAAAAAGGCTCATGGATG
GGCTGACAAATCAATGCAAAATGATCAATGAACAGTTTGAACCTCTTGTG
CCAGAAGGTCGTGACATTTTTGATGTGTGGGGAAATGACAGTAATTACAC
AAAAATTGTCGCTGCAGTGGACATGTTCTTCCACATGTTCAAAAAACATG
AATGTGCCTCGTTCAGATACGGAACTATTGTTTCCAGATTCAAAGATTGT
GCTGCATTGGCAACATTTGGACACCTCTGCAAAATAACCGGAATGTCTAC
AGAAGATGTGACGACCTGGATCTTGAACCGAAGTTGCAGATGAGATGG
TCCAAATGATGCTTCCAGGCCAAGAAATTGACAAGGCTGATTCATACATG
CCTTATTTGATCGACTTTGGATTGTCTTCTAAGTCTCCATATTCTTCCGT
CAAAAACCCTGCCTTCCACTTCTGGGGGCAATTGACAGCTCTTCTGCTCA
GATCCACCAGAGCAAGGAATGCCCGACAGCCTGATGACATTGAGTATACA
TCTCTTACTACAGCAGGTTTGTTGTACGCTTATGCAGTAGGATCCTCTGC
TGACTTGGCACAACAGTTTTGTGTTGGAGATAGCAAATACACTCCAGATG
ATAGTACCGGAGGATTGACGACTAATGCACCGCCACAAGGCAGAGATGTG
GTCGAATGGCTCGGATGGTTTGAAGATCAAAACAGAAAACCGACTCCTGA
TATGATGCAGTATGCGAAACGAGCAGTCATGTCACTGCAAGGCCTAAGAG
AGAAGACAATTGGCAAGTATGCTAAGTCAGAGTTTGACAAATGACCCTAT
AATTCTCAGATCACCTATTATATATTATGCTAGCTTGTTCGAACTCTTAA
TTAACGCCCCGAGTATGTCGACGTACTTAAGACCCTCTTGTGGTTTTTAT
TTTTTATCTGGTTTTGTGGTCTTCGTcgtctccggccgg

FIG. 2B

GENOME FRAGMENT B (1645 bp)
gctagctatgaaaaaaactaacagatatcATGGATAATCTCACAAAAGTT
CGTGAGTATCTCAAGTCCTATTCTCGTCTAGATCAGGCGGTAGGAGAGAT
AGATGAGATCGAAGCACAACGAGCTGAAAAGTCCAATTATGAGTTGTTCC
AAGAGGACGGAGTGGAAGAGCATACTAGGCCCTCTTATTTTCAGGCAGCA
GATGATTCTGACACAGAATCTGAACCAGAAATTGAAGACAATCAAGGCTT
GTATGTACCAGATCCGGAAGCTGAGCAAGTTGAAGGCTTTATACAGGGGC
CTTTAGATGACTATGCAGATGAGGACGTGGATGTTGTATTCACTTCGGAC
TGGAAACAGCCTGAGCTTGAATCCGACGAGCATGGAAAGACCTTACGGTT
GACATTGCCAGAGGGTTTAAGTGGAGAGCAGAAATCCCAGTGGCTTTTGA
CGATTAAAGCAGTCGTTCAAAGTGCCAAACACTGGAATCTGGCAGAGTGC
ACATTTGAAGCATCGGGAGAAGGGGTCATCATAAAAAAGCGCCAGATAAC
TCCGGATGTATATAAGGTCACTCCAGTGATGAACACACATCCGTcCCAAT
CAGAAGCCGTATCAGATGTTTGGTCTCTCTCAAAGACATCCATGACTTTC
CAACCCAAGAAAGCAAGTCTTCAGCCTCTCACCATATCCTTGGATGAATT
GTTCTCATCTAGAGGAGAATTCATCTCTGTCGGAGGTAACGGACGAATGT
CTCATAAAGAGGCCATCCTGCTCGGTCTGAGGTACAAAAAGTTGTACAAT
CAGGCGAGAGTCAAATATTCTCTGTAGactagtatgaaaaaaagtaacag
atatcacaatctaagtgttatcccaatccattcatcATGAGTTCCTTAAA
GAAGATTCTCGGTCTGAAGGGGAAAGGTAAGAAATCTAAGAAATTAGGGA
TCGCACCACCCCCTTATGAAGAGGACACTAACATGGAGTATGCTCCGAGC
GCTCCAATTGACAAATCCTATTTTGGAGTTGACGAGATGGACACTCATGA
TCCGAATCAATTAAGATATGAGAAATTCTTCTTTACAGTGAAAATGACGG
TTAGATCTAATCGTCCGTTCAGAACATACTCAGATGTGGCAGCCGCTGTA
TCCCATTGGGATCACATGTACATCGGAATGGCAGGGAAACGTCCCTTCTA
CAAGATCTTGGCTTTTTTGGGTTCTTCTAATCTAAAGGCCACTCCAGCGG
TATTGGCAGATCAAGGTCAACCAGAGTATCATGCTCACTGTGAAGGCAGG
GCTTATTTGCCACACAGAATGGGGAAGACCCCTCCCATGCTCAATGTACC
AGAGCACTTCAGAAGACCATTCAATATAGGTCTTTACAAGGGAACGATTG
AGCTCACAATGACCATCTACGATGATGAGTCACTGGAAGCAGCTCCTATG
ATCTGGGATCATTTCAATTCTTCCAAATTTTCTGATTTCAGAGAGAAGGC
CTTAATGTTTGGCCTGATTGTCGAGAAAAAGGCATCTGGAGCTTGGGTCC
TGGATTCTGTCAGCCACTTCAAATGAgctagtctagcttccagcttctga
Acaatccccggtttactcagtctctcctaattccagccttcgaa

FIG. 2C

GENOME FRAGMENT C (1689 bp)
ttcgaacaactaatatcctgtcttctctatccctatgaaaaaaactaaca
gagatcgatctgtttccttgacaccATGAAGTGCCTTTTGTACTTAGCTT
TTTTATTCATCGGGGTGAATTGCAAGTTCACCATAGTTTTTCCACACAAC
CAAAAAGGAAACTGGAAAAATGTTCCTTCCAATTACCATTATTGCCCGTC
AAGCTCAGATTTAAATTGGCATAATGACTTAaTAGGCACAGCCTTACAAG
TCAAAATGCCCAAGAGTCACAAGGCTATTCAAGCAGACGGTTGGATGTGT
CATGCTTCCAAATGGGTCACTACTTGTGATTTCCGCTGGTACGGACCGAA
GTATATAACACATTCCATCCGATCCTTCACTCCATCTGTAGAACAATGCA
AGGAAAGCATTGAACAAACGAAACAAGGAACTTGGCTGAATCCAGGCTTC
CCTCCTCAAAGTTGTGGATATGCAACTGTGACGGATGCTGAAGCAGCGAT
TGTCCAGGTGACTCCTCACCATGTGCTTGTTGATGAATACACAGGAGAAT
GGGTTGATTCACAGTTCATCAACGGAAAATGCAGCAATGACATATGCCCC
ACTGTCCATAACTCCACAACCTGGCATTCCGACTATAAGGTCAAAGGGCT
ATGTGATTCTAACCTCATTTCCATGGACATCACCTTCTTCTCAGAGGACG
GAGAGCTATCATCCCTAGGAAAGgAGGGCACAGGGTTCAGAAGTAACTAC
TTTGCTTATGAAACTGGAGACAAGGCCTGCAAAATGCAGTACTGCAAGCA
TTGGGGAGTCAGACTCCCATCAGGTGTCTGGTTCGAGATGGCTGATAAGG
ATCTCTTTGCTGCAGCCAGATTCCCTGAATGCCCAGAAGGGTCAAGTATC
TCTGCTCCATCTCAGACCTCAGTGGATGTAAGTCTCATTCAGGACGTTGA
GAGGATCTTGGATTATTCCCTCTGCCAAGAAACCTGGAGCAAAATCAGAG
CGGGTCTTCCCATCTCTCCAGTGGATCTCAGCTATCTTGCTCCTAAAAAC
CCAGGAACCGGTCCTGTCTTTACCATAATCAATGGTACCCTAAAATACTT
TGAGACCAGATACATCAGAGTCGATATTGCTGCTCCAATCCTCTCAAGAA
TGGTCGGAATGATCAGTGGAACTACCACAGAAAGGGaACTGTGGGATGAC
TGGGCTCCATATGAAGACGTGGAAATTGGACCCAATGGAGTTCTGAGGAC
CAGTTCAGGATATAAGTTTCCTTTATATATGATTGGACATGGTATGTTGG
ACTCCGATCTTCATCTTAGCTCAAAGGCTCAGGTGTTTGAACATCCTCAC
ATTCAAGACGCTGCTTCGCAGCTTCCTGATGaTGAGACTTTATTTTTTGG
TGATACTGGGCTATCCAAAAATCCAATCGAGTTTGTAGAAGGTTGGTTCA
GTAGTTGGAAGAGCTCTATTGCCTCTTTTTTCTTTAtCATAGGGTTAATC
ATTGGACTATTCTTGGTTCTCCGAGTTGGTATTTATCTTTGCATTAAATT
AAAGCACACCAAGAAAAGACAGATTTATACAGACATAGAGATGAACCGAC
TTGGAAAGTAActcaaatcctgcacaacagattcttcatgtttgaaccaa
Atcaacttgtgatatcatgctcaaagaggccttaattaa

FIG. 2D

GENOME FRAGMENT D (2851 bp)
ttaattaaattttaattttttaattttttatgaaaaaaactaacagcaatcA
TGGAAGTCCACGATTTTGAGACCGACGAGTTCAATGATTTCAATGAAGAT
GACTATGCCACAAGAGAATTCCTGAATCCCGATGAGCGCATGACGTACTT
GAATCATGCTGATTACAATTTGAATTCTCCTCTAATTAGTGATGATATTG
ACAATTTGATCAGGAAATTCAATTCTCTTCCGATTCCCTCGATGTGGGAT
AGTAAGAACTGGGATGGAGTTCTTGAGATGTTAACATCATGTCAAGCCAA
TCCCATCTCAACATCTCAGATGCATAAATGGATGGGAAGTTGGTTAATGT
CTGATAATCATGATGCCAGTCAAGGGTATAGTTTTTTACATGAAGTGGAC
AAAGAGGCAGAAATAACATTTGACGTGGTGGAGACCTTCATCCGCGGCTG
GGGCAACAAACCAATTGAATACATCAAAAAGGAAAGATGGACTGACTCAT
TCAAAATTCTCGCTTATTTGTGTCAAAAGTTTTTGGACTTACACAAGTTG
ACATTAATCTTAAATGCTGTCTCTGAGGTGGAATTGCTCAACTTGGCGAG
GACTTTCAAAGGCAAAGTCAGAAGAAGTTCTCATGAACGAACATATGCA
GGcTTAGGGTTCCCAGCTTGGGTCCTACTTTTATTTCAGAAGGATGGGCT
TACTTCAAGAAACTTGATATTCTAATGGACCGAAACTTTCTGTTAATGGT
CAAAGATGTGATTATAGGGAGGATGCAAACGGTGCTATCCATGGTATGTA
GAATAGACAACCTGTTCTCAGAGCAAGACATCTTCTCCCTTCTAAATATC
TACAGAATTGGAGATAAAATTGTGGAGAGGCAGGGAAATTTTTCTTATGA
CTTGATTAAAATGGTGGAACCGATATGCAACTTGAAGCTGATGAAATTAG
CAAGAGAATCAAGGCCTTTAGTCCCACAATTCCCTCATTTTGAAAATCAT
ATCAAGACTTCTGTTGATGAAGGGCAAAAATTGACCGAGGTATAAGATT
CCTCCATGATCAGATAATGAGTGTGAAAACAGTGGATCTCACACTGGTGA
TTTATGGATCGTTCAGACATTGGGGTCATCCTTTTATAGATTATTACgCT
GGACTAGAAAAATTACATTCCCAAGTAACCATGAAGAAAGATATTGATGT
GTCATATGCAAAAGCACTTGCAAGTGATTTAGCTCGGATTGTTCTATTTC
AACAGTTCAATGATCATAAAAAGTGGTTCGTGAATGGAGACTTGCTCCCT
CATGATCATCCCTTTAAAAGTCATGTTAAAGAAAATACATGGCCTACAGC
TGCTCAAGTTCAAGATTTTGGAGATAAATGGCATGAACTTCCGCTGATTA
AATGTTTTGAAATACCCGACTTACTAGACCCATCGATAATATACTCTGAC
AAAAGTCATTCAATGAATAGGTCAGAGGTGTTGAAACATGTCCGAATGAA
TCCGAACACTCCTATCCCTAGTAAAAAGGTGTTGCAGACTATGTTGGACA
CAAAGGCTACCAATTGGAAAGAATTTCTTAAAGAGATTGATGAGAAGGGC
TTAGATGATGATGATCTAATTATTGGTCTTAAAGGAAAGGAGAGGGAACT
GAAGTTGGCAGGTAGATTTTTCTCCCTAATGTCTTGGAAATTGCGAGAAT
ACTTTGTAATTACCGAATATTTGATAAAGACTCATTTCGTCCCTATGTTT
AAAGGCCTGACAATGGCGGACGATCTAACTGCAGTCATTAAAAAGATGTT
AGATTCCTCATCCGGCCAAGGATTGAAGTCATATGAGGCAATTTGCATAG
CCAATCACATTGATTACGAAAAATGGAATAACCACCAAAGGAAGTTATCA
AACGGCCCAGTGTTCCGAGTTATGGGCCAGTTCTTAGGTTATCCATCCTT
AATCGAGAGAACTCATGAATTTTTTGAGAAAAGTCTTATATACTACAATG
GAAGACCAGACTTGATGCGTGTTCACAACAACACACTGATCAATTCAACC
TCCCAACGAGTTTGTTGGCAAGGACAAGAGGGTGGACTGGAAGGTCTACG
GCAAAAAGGATGGAGTATCCTCAATCTACTGGTTATTCAAAGAGAGGCTA
AAATCAGAAACACTGCTGTCAAAGTCTTGGCACAAGGTGATAATCAAGTT
ATTTGCACACAGTATAAAACGAAGAAATCGAGAAACGTTGTAGAATTACA
GGGTGCTCTCAATCAAATGGTTTCTAATAATGAGAAAATTATGACTGCAA
TCAAAATAGGGACAGGGAAGTTAGGACTTTTGATAAATGACGATGAGACT
ATGCAATCTGCAGATTACTTGAATTATGGAAAAATACCGATTTTCCGTGG
AGTGATTAGAGGGTTAGAGACCAAGAGATGGTCACGAGTGACTTGTGTCA
CCAATGACCAAATACCCACTTGTGCTAATATAATGAGCTCAGTTTCCACA
AATGCTCTCACCGTAGCTCATTTTGCTGAGAACCCAATCAATGCCATGAT
ACAGTACAATTATTTTGGGACATTTGCTAGACTCTTGTTGATGATGCATG
ATCCTGCTCTTCGTCAATCATTGTATGAAGTTCAAGATAAGATACCGGGC
TTGCACAGTTCTACTTTCAAATACGCCATGTTGTATTTGGACCCTTCCAT
TGGAGGAGTGTCGGGCATGTCTTTGTCCAGGTTTTTGATTAGAGCCTTCC
CAGATCCCGTAACAGAAAGTCTCTCATTCTGGAGATTCATCCATGTACAT
GCTCGAAGTGAGCATCTGAAGGAGATGAGTGCAGTATTTGGAAACCCCGA
G

FIG. 2E

FRAGMENT E (2664)
CCCGAGATAGCCAAGTTcCGAATAACTCACATAGACAAGCTAGTAGAAGA
TCCAACCTCTCTGAACATCGCTATGGGAATGAGTCCAGCGAACTTGTTAA
AGACTGAGGTTAAAAAATGCTTAATCGAATCAAGACAAACCATCAGGAAC
CAGGTGATTAAGGATGCAACCATATATTTGTATCATGAAGAGGATCGGCT
CAGAAGTTTCTTATGGTCAATAAATCCTCTGTTCCCTAGATTTTTAAGTG
AATTCAAATCAGGCACTTTTTTGGGAGTCGCAGACGGGCTCATCAGTCTA
TTTCAAAATTCTCGTACTATTCGGAACTCCTTTAAGAAAAAGTATCATAG
GGAATTGGATGATTTGATTGTGAGGAGTGAGGTATCCTCTTTGACACATT
TAGGGAAACTTCATTTGAGAAGGGGATCATGTAAAATGTGGACATGTTCA
GCTACTCATGCTGACACATTAAGATACAAATCCTGGGGCCGTACAGTTAT
TGGGACAACTGTACCCCATCCATTAGAAATGTTGGGTCCACAACATCGAA
AAGAGACTCCTTGTGCACCATGTAACACATCAGGGTTCAATTATGTTTCT
GTGCATTGTCCAGACGGGATCCATGACGTCTTTAGTTCACGGGGACCATT
GCCTGCTTATCTAGGGTCTAAAACATCTGAATCTACATCTATTTTGCAGC
CTTGGGAAAGGGAAAGCAAAGTCCCACTGATTAAAAGAGCTACACGTCTT
AGAGATGCTATCTCTTGGTTTGTTGAACCCGACTCTAAACTAGCAATGAC
TATACTTTCTAACATCCACTCTTTAACAGGCGAAGAATGGACCAAAAGGC
AGCATGGGTTCAAAAGAACAGGGTCTGCCCTTCATAGGTTTTCGACATCT
CGGATGAGCCATGGTGGGTTCGCATCTCAGAGCACTGCAGCATTGACCAG
GTTGATGGCAACTACAGACACCATGAGGGATCTGGGAGATCAGAATTTCG
ACTTTTTATTCCAAGCAACGTTGCTCTATGCTCAAATTACCACCACTGTT
GCAAGAGACGGATGGATCACCAGTTGTACAGATCATTATCATATTGCCTG
TAAGTCCTGTTTGAGACCCATAGAAGAGATCACCCTGGACTCAAGTATGG
ACTACACGCCCCAGATGTATCCCATGTGCTGAAGACATGGAGGAATGGG
GAAGGTTCGTGGGGACAAGAGATAAAACAGATCTATCCTTTAGAAGGGAA
TTGGAAGAATTTAGCACCTGCTGAGCAATCCTATCAAGTCGGCAGATGTA
TAGGTTTTCTATATGGAGACTTGGCGTATAGAAAATCTACTCATGCCGAG
GACAGTTCTCTATTTCCTCTATCTATACAAGGTCGTATTAGAGGTCGAGG
TTTCTTAAAAGGGTTGCTAGACGGATTAATGAGAGCAAGTTGCTGCCAAG
TAATACACCGGAGAAGTCTGGCTCATTTGAAGAGGCCGGCCAACGCAGTG
TACGGAGGTTTGATTTACTTGATTGATAAATTGAGTGTATCACCTCCATT
CCTTTCTCTTACTAGATCAGGACCTATTAGAGACGAATTAGAAACGATTC
CCCACAAGATCCCAACCTCCTATCCGACAAGCAACCGTGATATGGGGTG
ATTGTCAGAAATTACTTCAAATACCAATGCCGTCTAATTGAAAAGGGAAA
ATACAGATCACATTATTCACAATTATGGTTATTCTCAGATGTCTTATCCA
TAGACTTCATTGGACCATTCTCTATTTCCACCACCCTCTTGCAAATCCTA
TACAAGCCATTTTTATCTGGGAAAGATAAGAATGAGTTGAGAGAGCTGGC
AAATCTTTCTTCATTGCTAAGATCAGGAGAGGGGTGGGAAGACATACATG
TGAAATTCTTCACCAAGGACATATTATTGTGTCCAGAGGAAATCAGACAT
GCTTGCAAGTTCGGGATTGCTAAGGATAATAATAAAGACATGAGCTATCC
CCCTTGGGGAAGGGAATCCAGAGGGACAATTACAACAATCCCTGTTTATT
ATACGACCACCCCTTACCCAAAGATGCTAGAGATGCCTCCAAGAATCCAA
AATCCCCTGCTGTCCGGAATCAGGTTGGGCCAATTACCAACTGGCGCTCA
TTATAAAATTCGGAGTATATTACATGGAATGGGAATCCATTACAGGGACT
TCTTGAGTTGTGGAGACGGCTCCGGAGGGATGACTGCTGCATTACTACGA
GAAAATGTGCATAGCAGAGGAATATTCAATAGTCTGTTAGAATTATCAGG
GTCAGTCATGCGAGGCGCCTCTCCTGAGCCCCCAGTGCCCTAGAAACTT
TAGGAGGAGATAAATCGAGATGTGTAAATGGTGAAACATGTTGGGAATAT
CCATCTGACTTATGTGACCCAAGGACTTGGGACTATTTCCTCCGACTCAA
AGCAGGCTTGGGGCTTCAAATTGATTTAATTGTAATGGATATGGAAGTTC
GGGATTCTTCTACTAGCCTGAAAATTGAGACGAATGTTAGAAATTATGTG
CACCGGATTTTGGATGAGCAAGGAGTTTTAATCTACAAGACTTATGGAAC
ATATATTTGTGAGAGCGAAAAGAATGCAGTAACAATCCTTGGTCCCATGT
TCAAGACGGTCGAC

FIG. 2F

FRAGMENT F (930)

GTCGACTTAGTTCAAACAGAATTTAGTAGTTCTCAAACGTCTGAAGTATA
TATGGTATGTAAAGGTTTGAAGAAATTAATCGATGAACCCAATCCCGATT
GGTCTTCCATCAATGAATCCTGGAAAAACCTGTACGCATTCCAGTCATCA
GAACAGGAATTTGCCAGAGCAAAGAAGGTTAGTACATACTTTACCTTGAC
AGGTATTCCCTCCCAATTCATTCCTGATCCTTTTGTAAACATTGAGACTA
TGCTACAAATATTCGGAGTACCCACGGGTGTGTCTCATGCGGCTGCCTTA
AAATCATCTGATAGACCTGCAGATTTATTGACCATTAGCCTTTTTTATAT
GGCGATTATATCGTATTATAACATCAATCATATCAGAGTAGGACCGATAC
CTCCGAACCCCCCATCAGATGGAATTGCACAAAATGTGGGGATCGCTATA
ACTGGTATAAGCTTTTGGCTGAGTTTGATGGAGAAAGACATTCCACTATA
TCAACAGTGTTTAGCAGTTATCCAGCAATCATTCCCGATTAGGTGGGAGG
CTGTTTCAGTAAAAGGAGGATACAAGCAGAAGTGGAGTACTAGAGGTGAT
GGGCTCCCAAAAGATACCCGAATTTCAGACTCCTTGGCCCCAATCGGGAA
CTGGATCAGATCTCTGGAATTGGTCCGAAACCAAGTTCGTCTAAATCCAT
TCAATGAGATCTTGTTCAATCAGCTATGTCGTACAGTGGATAATCATTTG
AAATGGTCAAATTTGCGAAaAAACACAGGAATGATTGAATGGATCAATAG
ACGAATTTCAAAAGAAGACCGGTCTATACTGATGTTGAAGAGTGACCTAC
ACGAGGAAAACTCTTGGAGAGATTAAaaaatcatgaggagactccaaact
Ttaagtatgaaaaaactttgatccttaag

FIG. 2G

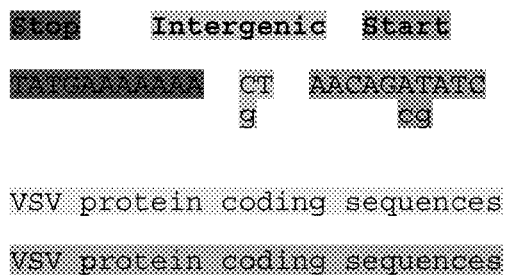

```
                                                                                    PacI                    L protein
4701 attttaatt tt                 ctca aatcctgcac aacagattct tcatgttga   accaaatcaa cttgtgatat catgctcaaa gaggccttaa ttaaattta 4700
     CGGCCTTGCA AAATTAA           AGTCCACGAT                                                                               4800
4801 AGAATTCCTG AATCCCGATG AGCGCATGAC GTACTTGAAT CATGCTGATT ACAATTTGAA TTCTCCCTCA ATTAGTGATG TGATTTCAAT GAAGATGACT ATGCCACAAG 4900
4901 AAATTCAATT CTCTTCCGAT TCCCTCGATG TGGATAGTGA AGAACTCGGA TGGAGTTTTT GAGATGTAAA CATCATGTCA AGCCAATCCC ATCTCAACAT TTTGATCAGG 5000
5001 CTCAGATGCA TAAATGGATG GGAAGTTGGT TAATGTCTGA AACCAATGAT GCCAGTCAAG GGTATAGTTT TTTACATGAA GTGGACAAAG AGGCAGAAAT 5100
5101 AACATTTGAC GTGGTGGACA CCTTCATCCG CGGCTGGAGC AACAAACCAA TTGAAAAGAA AGATGGACTG ACTCATTCAA AATTCTCGCT 5200
5201 TATTTGTGTC AAAAGTTTTT CGACTTACAC AAGTTGACAT TAATCTTAAA TGCTGTCTCT GAGTGTGAAT TGCTCAACTT GGCGAGGACT TTCAAAGGCA 5300
5301 AAGTCAGAAG AAGTTCTCAT TGAACGACAA TATGCAGGCT TACGGTTCCC AGCTTGGGTC CTACTTTTAT TTCAGAAGGA TGGCTTACT TCAAGAAACT ACACAACCTG 5400
5401 TGATATTCTA ATGGACCGAA ACTTTCTCTT CTCCCTTTTA AATGCTCAAA GATGTGAATA AATATCTACA GAATTGGACA TAAAATTGTG GAGAGGCAAG GAAATTTTTC TTATGACTTG ATTAAAATGG 5500
5501 TTCCTCGAGC AAGACATCTT CTCCCTTTTA AATGCTCAAA GATGTGAATA AATATCTACA GAATTGGACA TAAAATTGTG GAGAGGCAAG GAAATTTTTC TTATGACTTG ATTAAAATGG 5600
5601 TGGAACCGAT ATGCAACTTG AACTGATGA AATTAGCAAG AGAATCAAGG CCTTTAGTTC CACAGATTTC TCATTTTGAA AATCATATCA AGACTTCTGT 5700
5701 TGATGAACGG GCAAAATTCG ACCGAGGTAT AAGATTCCTC CATGATCAGA TAATGAGTGT GAAAACAGTG GATCTCACAC TGGTCGATTA TGGATCGTTC 5800
5801 AGACATTGGG GTCATCCTTT TATAGATTAT TACGCTGGAC TAGAAAAATT ACATTCCAA GTAACCATGA AGAAAGATAT TGATGTGTCA TATGCAAAAG 5900
5901 CACTTTGCAA TGATTTAGCT TATTTAGGT CGGATTGTTC GTTCAATGAT CATAAAAAGT GGTTCGTGAA TGGAGACTTG CTCCCCTCATG ATCATCCCTT 6000
```

```
8101 ATGTAACACA TCAGGGTTCA ATTATGTTTC TGTCCATTGT CCAAGACGGGA TCCATGACGT CTTTAGTTCA CGGGGACCAT TGCCCTGCTTA TCTAGGGTCT 8200
8201 AAAACATCTG AATCTACATC TATTTTGCAG CCTTGGGAAA CGGAAAGCAA AGTCCCACTG ATTAAAAGAG CTACACGTCT TAGAGAATGG ATCTCTTGGT 8300
8301 TTGTTGAACC CGACTCTAAA CTAGCAATGA CTATACTTTC TAACATCCAC TCTTTAACAG GCGAAGAATG GACCAAAAGG CAGCATGGGT TCAAAGAAAC 8400
8401 AGGGTTCTGCC CTTCATAGGT TTTCGACATC TCGATGAGC CATGTGGGT TGGCATCTCA GAGCACTGCA GGTTGATGGC AACTACAGAC 8500
8501 ACCATGAGGG ATCTGGGAGA TCAGAATTTC GACTTTTTAT TCCAAGCAAC GTTGCTCTAT GCTCAAATTA CCACCACTGT TGCCAAGAGAC GGATGGATCA 8600
8601 CCAGTTGTAC AGATCATTAT CATATTGCCT GTAAGTCCTG TTTGAGACCC ATAGAAGAGA TCACCCTGGA CTTCAAGTATG GACTACGGC CCCCAGATGT 8700
8701 ATCCCATGTG CTTGAAGATG CTGAGAATGG GGAAGGTTCG TGGGACACAAG GATAAAAACA GATCTATCCT TTAGAAGGGA ATTGGAAGAA TTTAGCACCT 8800
8801 GCTGAGCAAT CCTATCAAGT GTTCTTAAAA AGAGTCGAAG CTTGGCCGTAT CGGACGCAGT ATAGGTTTTC TATATGGAGA CTTGGCCGTAT AGAAAATCTA CTCATGCCGA GGACAGTTCT CTATTTCCTC 8900
8901 TATCTATACA AGTTCGTATT AGAGGTCGAG GTTCTTAAA AGGGTTGCTA GACGGATTAA TGATTGATAA ATTGAGTGTA TCCATCTCAT TCCTTTCTCT TACTAGATCA 9100
9001 GGCTCATTTG AAGAGGCCGG CCTAACGCAGT GTACGGAGGT TTGATTTACT TGATTGATAA ATTGAGTGTA TCCATCTCAT TCCTTTCTCT TACTAGATCA 9100
9101 CGAACTCATTA GAGACGAATT AGAAACGATT CCCCACAAGA TCCCAACCTC CTATCCGACA AGCAACCCGT ATATGGGGT GATTGTCAAGA AATTACTTCA 9200
9201 AATACCAATG CCGTCTAATT GAAAAGGGAA AATACAGATC ACATTATTCA CAATTATGGT TATTCTCAGA TGTCTTATCC ATAGAGCTGG CAAATCTTTC TTCATTGCTA 9300
9301 CTCTATTTCC ACCACCTCTG AGGGGTGGCA AGACATACAT GTGAAATCCT ATACAAGCCA TTTTTATCTG GGAAGATAAA GAATGAGTTG TGTTCAAGAGG AAATGACACA TGCTTGCAAG TTCGGATTG 9400
9401 AGATCAGGAG AGGGGTGGCA TAATAAAAGAC ATTAGCTATC CCCTTGGGG AAGGAAATCC AGAGGGACAA TTACAACAAT CCTTTTTAT TATACGACCA CCCCTTACCC 9500
9501 CTAAAGGATAA GACATGCTA GAGTGCCTC CAGAATTCA CTGCCTTTGCC AAGCCCGAGGA CCAATTCCA ACATTGCTA ACTGCCGCTC ATTATAAAT TGGAGTATA 9600
9601 AAGATGCTA GAGGTCCGAC TTCTTGACTT TTACAGCGAC TTTTATCAT GGTTGAGTCAT CCTCCGAGG ATGACTGCTG CATTACTACG AGAAAATGTG CATAGCACAG 9800
9701 TTACATGGAA TGGAATCCA TTCAGCCGAC TTCTTGACTT TTACAGCGAC TTTTATCAT GGTTGAGTCAT CCTCCTGAGC CCCCAGTGC CCTAGAAACT TTAGAGCGAG ATAAATGCAG 9900
9801 GAATATTCAA TAGTCTGTTA GAATTATCAG GTTGGAATA TCCATCTGAC TATGTGACC CAAGGACTTG GGACTATTTC CTGGACTCA AAGCAGGCTT GGGGCTTCAA 10000
9901 ATGTGTAAAT GGTGGAATA TCCATCTGAC TATGTGACC CAAGGACTTG GGACTATTTC CTGGACTCA AAGCAGGCTT GGGGCTTCAA 10000
10001 ATTGAGTTAA TTCTAATGCA TATGAGTT CGGATTCTT CTACTAGCCT CGGATTGTT CTACAGCCT GAATGATGAC ACCATGATGTT GCACCGGATT TTGGATGAGC TCGACTTAGT 10200
10101 AAGGAGTTTT AATCTACAAG CATATATTG TGAGAGCAA AAGAATGCAG TAACAATCCT TGGTCCCATG TTCAAGACGG TTGGATGAGC TCGACTTAGT 10200
```

SalI

Rescue by Calcium-Phosphate Transfection

DAY 1
- Feed monolayers cultured in 6-well plates and incubate 1-3h (32°C, 3% $CO_2$).

- Prepare calcium-phosphate-DNA precipitates and distribute onto cells (viral genomic cDNA, pT7-N, pT7-P, pT7-L, pT7-M, pT7-G, pCMV-T7)

- Incubate 3h (32°C, 3% $CO_2$).

- Heat shock 3h (43°C, 3% $CO_2$).

- Return cells to 32°C incubator (3% $CO_2$) and continue incubation overnight.

DAY 2
- Wash monolayers and feed with fresh medium. Incubate 2-3 days (32-37°C, 5% $CO_2$).

DAY 4-5
- Transfer transfected cells onto a fresh cell monolayer to initiate coculture. Replace medium and incubate 3-5 days and examine for evidence of CPE.

FIG. 5

VESICULAR STOMATITIS VIRUS AND VIRUS RESCUE SYSTEM

INCORPORATION BY REFERENCE

This application is a continuation of U.S. application Ser. No. 16/717,360 filed Dec. 17, 2019, now allowed, which is a continuation of U.S. application Ser. No. 15/417,256 filed Jan. 27, 2017, now U.S. Pat. No. 10,544,430, which is a continuation of U.S. application Ser. No. 13/623,437 filed Sep. 20, 2012, which claims priority to U.S. provisional patent application Ser. No. 61/537,497 filed Sep. 21, 2011. Reference is made to U.S. patent application Ser. No. 12/708,940 filed Feb. 19, 2010.

The foregoing applications, and all documents cited therein or during their prosecution ("appln cited documents") and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SEQUENCE LISTING

The instant application contains a Sequence Listing which has been submitted in XML format and is hereby incorporated by reference in its entirety. Said XML copy, created on May 12, 2023, is named Y7969_04018SL.xml and is 59,882 bytes in size.

FIELD OF THE INVENTION

The present invention relates to a novel vesicular stomatitis virus for use in prophylactic and therapeutic vaccines.

BACKGROUND OF THE INVENTION

Vesicular stomatitis virus (VSV) is a member of the Rhabdoviridae family of enveloped viruses that contain a single-stranded, nonsegmented, negative-sense RNA genome. The VSV genome is composed of 5 genes arranged sequentially 3'-N—P-M-G-L-5', which each encode a polypeptide found in mature virions (Rose et al. 2001. Rhabdoviridae: the viruses and their replication, p. 1221-1244. In D. M. Knipe and P. M. Howley (ed.), Fields Virology, vol. 1. Lippincott, Williams and Wilkins, Philadelphia). The virus naturally infects livestock, but is known to infect humans producing mild illness or no symptoms of infection (Clarke et al. 2006. Springer seminars in immunopathology 28:239-253 and Letchworth et al. 1999. Vet J 157:239-260).

VSV is an important technology platform. It is a promising human vaccine vector candidate for a variety of reasons, notably, i) as mentioned above, it does not cause serious disease in humans; ii) genetic systems have been developed for producing recombinant viruses (Conzelmann. 2004. Curr Top Microbiol Immunol 283:1-41); iii) it can be modified to express foreign proteins; iv) it expresses foreign proteins abundantly; v) it elicits immune responses in infected humans (Reif et al. 1987. Am J Trop Med Hyg 36:177-182); and vi) it has been safely tested as a vaccine vector in many animal models including nonhuman primates (Clarke et al. 2006. Springer seminars in immunopathology 28:239-253).

There remains a need to express immunogens in recombinant vaccines. To do so, it is advantageous to have a vector that is genetically stable, easily modified, and efficiently propagated.

Citation or identification of any document in this application is not an admission that such document is available as prior art to the present application.

SUMMARY OF THE INVENTION

The invention stems, in part, from Applicants wishing to design a vector with a clearly defined and documented lineage that was specifically modified without altering amino acid coding or the function of cis-acting sequences to facilitate subsequent VSV vector construction. It was also important and practical to start with a VSV isolate adapted for propagation in primate epithelial cell lines (rather than commonly-used BHK fibroblastic cells) to promote greater genetic stability during VSV vector production in Vero cells used for vaccine manufacturing. Because Applicants' vaccine development plans included construction of highly modified VSV vectors that Applicants anticipated to be difficult to rescue, Applicants designed a cloning plasmid that included strategic modifications to increase the productivity of Applicants' recombinant virus rescue system.

The present invention relates to a vesicular stomatitis virus (VSV) genomic clone which may comprise: (a) a VSV genome encoding and expressing a nucleocapsid, phosphoprotein, matrix, glycoprotein and large protein, wherein the VSV genome may comprise nucleotide substitutions and amino acid coding changes to improve replicative fitness and genetic stability, (b) a cloning vector, (c) an extended T7 promoter, (d) a hammerhead ribozyme, (e) a hepatitis delta virus ribozyme and T7 terminator, (f) unique restriction endonuclease cleavage sites in a VSV genomic sequence and/or (g) a leader and a trailer that are cis-acting sequences controlling mRNA synthesis and replication.

In one embodiment, the cloning vector may be pSP72 (Genbank X65332.2). In another embodiment, the extended T7 promoter may be PT7-g10 (Lopez et al. 1997. Journal of molecular biology 269:41-51, the disclosure of which is incorporated by reference). RNA polymerase T7 functions first as a DNA binding protein that recognizes a specific DNA sequence and subsequently transitions its activity into an elongating RNA polymerase. The nature of the nucleotide sequence of the region initially transcribed by the polymerase plays a role in the transition from DNA binding protein to an elongating polymerase complex. The transcribed region in the PT7-g10 promoter may include nucleotide sequences that promote more efficient transition from DNA binding protein to elongating RNA polymerase. (Temiakov D, Mentesana P E, Ma K, Mustaev A, Borukhov S, McAllister W T. The specificity loop of T7 RNA polymerase interacts first with the promoter and then with the elongating transcript, suggesting a mechanism for promoter clearance. Proc Natl Acad Sci USA. 2000 Dec. 19; 97 (26): 14109-14, the disclosure of which is incorporated by reference).

In another embodiment, the unique restriction endonuclease cleavage sites may be 1367 NheI, 2194 SpeI, 2194 BstBI, 4687 PacI, 7532 AvaI, 10190 SalI and 11164 AflII. In yet another embodiment, the VSV genomic clones may be depicted in FIG. 1. In another embodiment, SphI and XhoI may be added for cloning into position 1 between the leader and N gene junction of the VSV genomic clones depicted in FIG. 1.

The nucleotide substitutions in the VSV genome may be selected from the group consisting of: 1371 CA>GC (NheI), after 2195 insert TAG (SpeI) (all genome numbers subsequent to this insertion have been adjusted to include +3 bp), 3036 G>T improves match to consensus transcription stop signal, 3853 X>A (an ambiguity in Genbank file EF197793.1), 4691 T>A to generate PacI, 7546 C>A silent change in L coding sequence eliminates a BstBI site. Additionally, amino acids substitutions may be introduced to increase match with a VSV consensus using nucleotide substitutions selected from 1960 TAC>TCC to change Y>S, 3247 GTA>ATA to change V>I, 3729 AAG>GAG to change K>E, 4191 GTA>GAA to change V>E, 4386 GGT>GAT to change G>D, 4491 ACC>ATC to change T>I, 5339 ATT>CTT to change I>L, 5834 ACT>GCT to change T>A and/or 10959 AGA>AAA to change R>K, wherein the nucleotide position is according to GenBank Accession Number EF197793. The nucleotide substitutions in the VSV genome (wherein the nucleotide position is according to GenBank Accession Number EF197793) may be selected from the group consisting of:

The present invention also relates to method for rescuing VSV, which may comprise combining a T7 RNA polymerase promoter and a hammerhead ribozyme sequence to increase the efficiency of synthesis and processing of full-length VSV genomic RNA in transfected cells.

In one embodiment, the T7 RNA polymerase promoter may be a minimal functional sequence designed to initiate transcription very close to or precisely at the 5' terminus of the genomic clone. Advantageously, the T7 promoter may be a T7 promoter sequence that enhances formation of stable initiation and elongation complexes and a hammerhead ribozyme sequence at the 5' terminus that catalyzes removal of extra nucleotides restoring the authentic 5' terminus of the genomic transcript.

In another embodiment, the plasmids used to support virus rescue encoding VSV nucleocapsid, phosphoprotein, matrix, glycoprotein and large protein may be optimized to improve expression of the trans-acting proteins to initiate virus rescue. Advantageously, the optimization is codon optimization. In one embodiment, the gene optimization

| | Nucleotide position in EF197793 | Nucleotide position in rEF197793 | Nucleotide Change | Purpose |
|---|---|---|---|---|
| 1 | Substitution 1371-2 | Substitution 1371-2 | CA > GC | Creates a unique NheI cleavage site between N and P gens |
| 2 | Substitution 1960-2 | Substitution 1960-2 | TAC > TCC | Y > S substitution in P protein amino acid sequence to agree with consensus. |
| 3 | Insert after 2195 | 3 base insert after 2195 | Insert TAG | Creates a unique SpeI site between P and M genes |
| 4 | Substitution 3039 | Substitution 3042 | G > T | Improves agreement with consensus. Also improves agreement with consensus transcription stop signal |
| 5 | Substitution 3234-6 | Substitution 3237-9 | GTA > ATA | V > I substitution in P protein amino acid sequence to agree with consensus. |
| 6 | Substitution 3729-31 | Substitution 3732-34 | AAG > GAG | K > E substitution in G protein amino acid sequence to agree with consensus. |
| 7 | Substitution 3856 | Substitution 3859 | N > A | Replace unknown base in Genbank file with consensus |
| 8 | Substitution 4191-93 | Substitution 4194-6 | GTA > GAA | V > E substitution in G protein amino acid sequence to agree with consensus. |
| 9 | Substitution 4386-88 | Substitution 4389-92 | GGT > GAT | G > D substitution in G protein amino acid sequence to agree with consensus. |
| 10 | Substitution 4491-93 | Substitution 4494-96 | ACC > ATC | T > I substitution in G protein amino acid sequence to agree with consensus. |
| 11 | Substitution 4694 | Substitution 4697 | T > A | Creates unique PacI cleavage site between G and L genes |
| 12 | Substitution 5339-41 | Substitution 5342-44 | ATT > CTT | I > L substitution in L protein amino acid sequence to agree with consensus. |
| 13 | Substitution 5834-6 | Substitution 5837-40 | ACT > GCT | T > A substitution in L protein amino acid sequence to agree with consensus. |
| 14 | Substitution 10959-61 | Substitution 10962-64 | AGA > AAA | R > K substitution in L protein amino acid sequence to agree with consensus. |
| 15 | Substitution 7546 | Substitution 7549 | C > A | Eliminates a BstBI site in the L gene sequence making the BstBI site between the M and G genes unique. This substitution was silent for amino acid coding. |

The VSV genomic clone may comprise the nucleotide sequences of the VSV genome encoding and expressing a nucleocapsid, phosphoprotein, matrix, glycoprotein and large protein may be selected from the group consisting of FIGS. 2B-2G. The VSV genomic clone may also comprise the nucleotide sequences of the VSV genome encoding and expressing a nucleocapsid, phosphoprotein, matrix, glycoprotein and large protein may be selected from the group consisting of FIGS. 3A-3G.

may comprise replacing a VSV nucleotide sequence with codons used by highly expressed mammalian genes. In another embodiment, the codon optimization may comprise eliminating potential RNA processing signals in the coding sequence that might direct unwanted RNA splicing or cleavage/polyadenylation reaction, wherein the eliminating may comprise: (a) identifying potential splice site signals and remove by introducing synonymous codons and/or (b) scanning an insert for consensus cleavage/polyadenylation signals (AAUAAA) and introducing synonymous codons to disrupt the consensus cleavage/polyadenylation signals. In yet another embodiment, the gene optimization may comprise (a) adding a preferred translational start sequence (the Kozak sequence) and/or (b) adding a preferred translational stop codon. In still another embodiment, the gene optimization may comprise scanning a sequence for homopolymeric stretches of 5 nucleotides or more and interrupting the sequences by introducing synonymous codons. In another embodiment, the gene optimization may comprise scanning a sequence for restriction endonuclease cleavage sites and eliminate any unwanted recognitions signals. In yet another embodiment, the gene optimization may comprise confirming that a modified sequence translates into the expected amino acid sequence.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 2B depicts a sequence of genome fragment VSV-A/G (1489 bp) (SEQ ID NO: 9).

FIG. 2C depicts a sequence of genome fragment B (1645 bp) (SEQ ID NO: 10).

FIG. 2D depicts a sequence of genome fragment C (1689 bp) (SEQ ID NO: 11).

FIG. 2E depicts a sequence of genome fragment D (2851 bp) (SEQ ID NO: 12).

FIG. 2F depicts a sequence of genome fragment E (2664) (SEQ ID NO: 13).

FIG. 2G depicts a sequence of genome fragment F (930) (SEQ ID NO: 14).

Figure 3G:
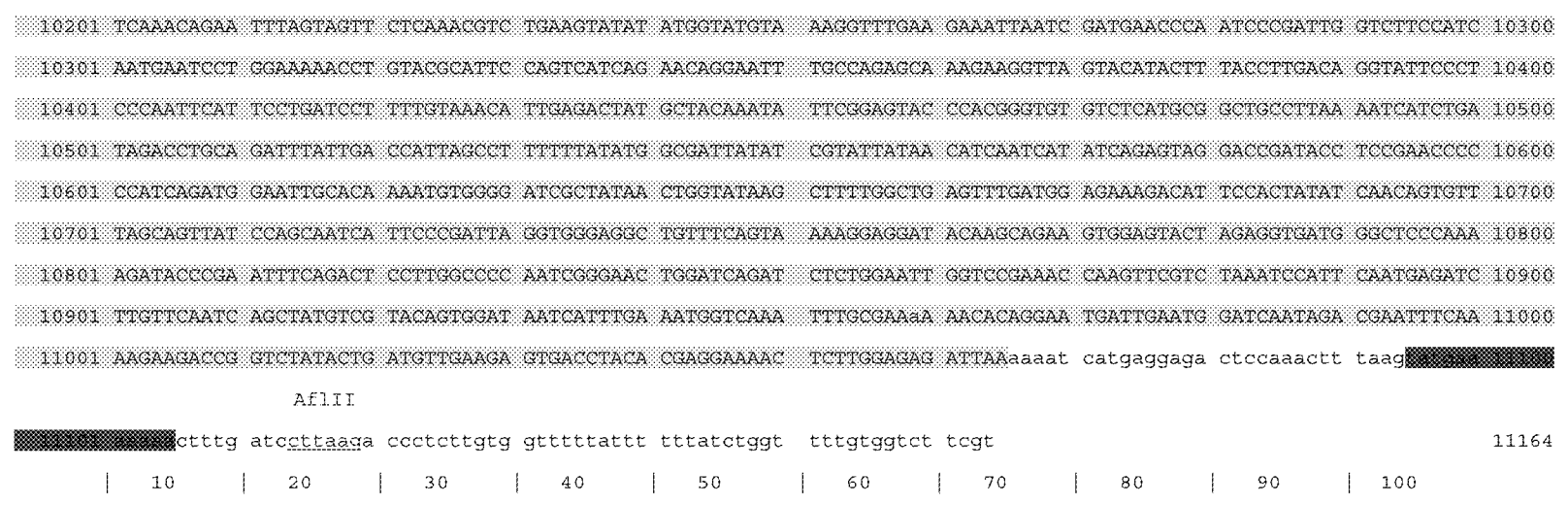

FIG. 3A depicts a schematic VSV annotated rVSV genomic cDNA and mRNA transcriptional control and processing signals. (SEQ ID NOS 15-16, respectively, in order of appearance).

FIGS. 3B-3G depict a sequence of the VSV (SEQ ID NO: 17) of FIG. 3A.

FIG. 5 depicts a method for virus rescue by calcium-phosphate transfection. The flow diagram summarizes the procedure described in detailed in section 2. Elimination of helper-virus, inclusion of plasmids encoding matrix proteins and glycoproteins, heatshock treatment, and the coculture procedure differentiates this technique from traditional methods.

DETAILED DESCRIPTION

Figure 1:
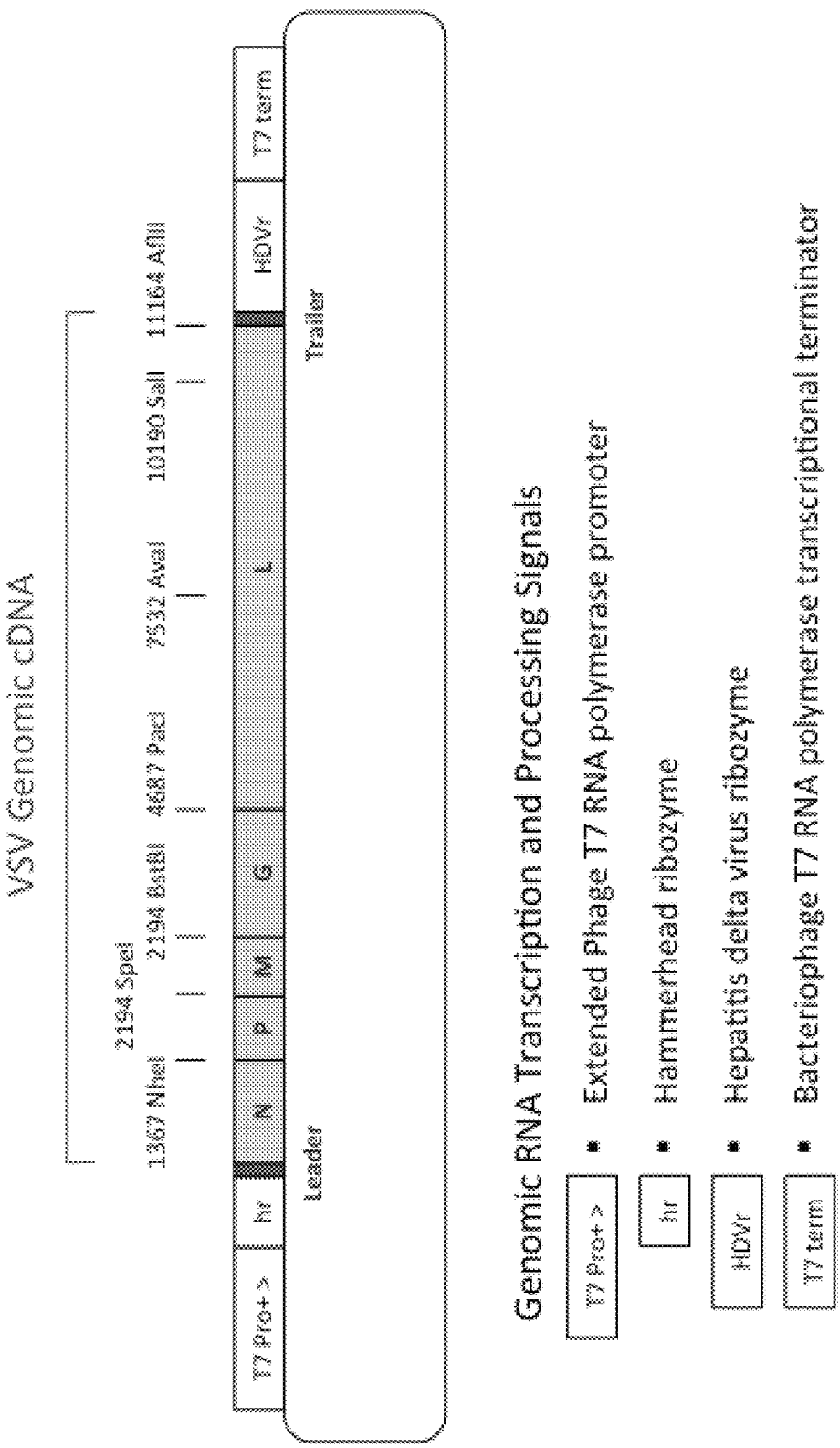
FIG. 1 depicts a schematic structure of a VSV genomic clone of the invention. Features include a cloning vector based on pSP72 (Genbank X65332.2), an extended T7 promoter is PT7-g10 described by Lopez et al. (Lopez et al., 1997. Journal of molecular biology 269:41-51), a hammerhead ribozyme designed following the rules for constructing self-cleaving RNA sequences (Inoue et al. 2003. J Virol Methods 107:229-236 and Ruffner et al. 1990. Biochemistry 29:10695-10702), a hepatitis delta virus ribozyme and T7 terminator as described before for the measles virus rescue system (Radecke et al 1995. The EMBO journal 14.5773-5784, 23 and Sidhu et al. 1995. Virology 208:800-807), unique restriction endonuclease cleavage sites indicated above the VSV genomic sequence (red), leader and trailer as cis-acting sequences in the termini that control mRNA synthesis and replication and N, nucleocapsid; P, phosphoprotein; M, matrix; G, glycoprotein; L, large protein.

Applicants used VSV to develop several types of HIV vaccine candidate including VSV-SIV and VSV-HIV chimeric viruses in which the natural VSV attachment protein (G) is functionally replaced with SIV/HIV Env and EnvG hybrids, vectors designed with Env epitopes grafted into VSV G and vectors designed to display a variety of Env immunogens as transmembrane proteins on the surface of VSV particles and infected cells.

Applicants used VSV to develop technology platforms for antibody-based screening and selection procedures that will allow Applicants to evolve novel Env immunogens. These methods take advantage of the fact that VSV evolves rapidly when selective pressure is applied (Novella. 2003. Curr Opin Microbiol 6:399-405). Methods in development include a procedure that allows Applicants to select for Env mutants that bind most strongly with monoclonal antibodies, a method for rapidly producing mutants that escape neutralizing antibodies that bind HIV Env, and a method for generating live or inactivated VSV particles displaying Env.

All of the recombinant VSVs are based on a genomic DNA clone Applicants designed. Applicants decided to develop Applicants' own VSV vector for several reasons. First, Applicants wanted to begin Applicants' vaccine development program with a vector that has a clearly defined and documented lineage. Second, Applicants planned to introduce a limited number of strategic nucleotide changes into the genome that would facilitate subsequent VSV vector construction without altering amino acid coding or the function of cis-acting sequences. Third, it was important and practical to start with a VSV isolate adapted for propagation in primate epithelial cell lines (rather than commonly-used BHK fibroblastic cells) to promote greater genetic stability during VSV vector production in Vero cells used for vaccine manufacturing. Finally, because Applicants' vaccine development plans included construction of highly modified VSV vectors that Applicants anticipated to be difficult to rescue, Applicants designed a cloning plasmid that included strategic modifications to increase the productivity of Applicants' rescue system.

Applicants could have used the VSV vector background developed in 1995 at Yale University (Lawson et al. 1995. Proceedings of the National Academy of Sciences of the United States of America 92:4477-4481) as Applicants' starting material. Applicants decided against this option because the Yale vector is a hybrid constructed from sequences originating from multiple VSV isolates propagated under diverse laboratory conditions (it was constructed when molecular cloning was considerably more complex and costly), and for Applicants' purposes, the Yale clone also needed further modification to introduce unique restriction enzyme cleavage sites. Thus, Applicants found it simpler to engineer a vector fitting Applicants' needs by assembling synthetic DNA fragments based on a virus genomic sequence described in a manuscript by Remold and colleagues (Remold et al. 2008. Mol Biol Evol 25:1138-1147). In the end, Applicants' vector nucleotide sequence differs from circulating wild-type viruses (VSV Indiana) and the Yale molecular clone by about 1%.

To construct Applicants' VSV genomic clone (FIG. 1), Applicants started with the sequence (Genbank Accession EF197793) of a VSV isolate (Mudd Summers Strain, Indiana Serotype) adapted to growth in human epithelial cell lines (Remold et al. 2008. Mol Biol Evol 25:1138-1147). Applicants modified EF197793 nucleotide sequence to create unique restriction endonuclease cleavage sites (FIG. 1 and Table 1) that would facilitate subsequent genetic modification, and Applicants also introduced a number of nucleotide substitutions and amino acid coding changes that Applicants anticipated would improve the replicative fitness and genetic stability of Applicants' recombinant vector based on analysis of consensus sequences generated by aligning the genomes of lab-adapted and circulating wild-type viruses. The modified version of the EF197793 sequence (rEF197793 in Table 1) was then used as a template to have 6 DNA fragments synthesized, which Applicants subsequently assembled into the recombinant full-length genomic clone (FIGS. 2A-2G). An annotated modified VSV genomic sequence is included in FIGS. 3A-3G.

Applicants also introduced improvements to the plasmid DNA cloning vector that enhanced Applicants' ability to rescue recombinant VSV vectors from transfected cells. Applicants did this because, as mentioned above, Applicants' vaccine development plans included construction of highly modified VSV vectors that Applicants anticipated would be difficult to rescue because Applicants are adding one or more foreign gene inserts and also introducing changes expected to decrease replicative fitness. Negative-strand RNA virus rescue from cloned DNAs is a multistep process that includes: 1) cotransfection of multiple plasmid DNAs including the plasmid DNA containing the VSV genomic cDNA, a plasmid encoding bacteriophage T7 RNA polymerase, and multiple plasmids expressing viral proteins (i.e. VSV N, P, M, G, and L) needed to initiate virus replication in transfected cells; 2) intracellular synthesis of a full-length genomic RNA by bacteriophage T7 RNA polymerase; 3) precise processing of the primary genomic transcript to produce requisite termini for replication; 4) de novo packaging of the genomic RNA by the viral nucleocapsid protein to generate a functional template for RNA replication; 5) and finally, initiation of RNA synthesis by the viral RNA-dependent RNA polymerase (Conzelmann. 2004. Curr Top Microbiol Immunol 283:1-41 and Neumann et al. 2002. J Gen Virol 83:2635-2662). The rescue process is relatively inefficient and at times it restricts the ability to rescue the desired recombinant, although incremental improvements (Ghanem et al. 2011. European Journal of cell biology, Inoue et al. J Virol Methods 107:229-236, Parks et al. 1999. J Virol 73:3560-3566, Witko et al. 2010. J Virol Methods 164:43-50 and Witko et al. 2006. J Virol Methods 135:91-101) in the rescue procedure have made it more efficient since it was first described (Schnell et al. 1994. Embo J 13:4195-4203). As described herein, to improve Applicants' VSV rescue system, Applicants used a novel combination of a more efficient T7 RNA polymerase promoter and a hammerhead ribozyme sequence to increase the efficiency of synthesis and processing of full-length VSV genomic RNA in transfected cells.

The T7 RNA polymerase promoter used in published virus rescue methods is a minimal functional sequence designed to initiate transcription very close to or precisely at the 5' terminus of the genomic clone (Lawson et al. 1995. Proceedings of the National Academy of Sciences of the United States of America 92:4477-4481, Radecke et al. 1995. The EMBO Journal 14:5773-5784 and Schnell et al. 1994. Embo J 13:4195-4203). Although this promoter design is effective for forming the 5' end of the genomic transcript, it is not the most efficient promoter for initiating productive RNA synthesis. Thus, to improve VSV rescue efficiency, Applicants developed a modified plasmid that uses a longer T7 promoter sequence known to enhance formation of stable initiation and elongation complexes (Lopez et al. 1997. Journal of molecular biology 269:41-51). Because the longer T7 promoter includes downstream transcribed bacteriophage sequences, extra nucleotides are added to the primary VSV genomic transcript. To remove these extra nucleotides, Applicants have incorporated a hammerhead ribozyme (Inoue et al. J Virol Methods 107: 229-236 and Ruffner et al. 1990. Biochemistry 29:10695-10702) sequence at the 5' that which catalyzes removal of extra nucleotides restoring the authentic 5' end of the genomic transcript.

Finally, the VSV rescue system Applicants developed uses protocols similar to those described before with modification (Witko et al. 2006. J Virol Methods 135:91-101). The most significant change is that Applicants have 'optimized' (Examples 3 and 4) Applicants' plasmids encoding N, P, M, G, and L and placed the optimized genes under control of the human cytomegalovirus promoter to improve expression of the trans-acting proteins needed to initiate virus rescue. This modification of the rescue system was suggested by results showing that codon optimization significantly enhances expression in transfected cells of plasmid-encoded viral G proteins from respiratory syncytial virus and VSV (Ternette et al. 2007. Virol J 4:51 and Witko et al. 2010. J Virol Methods 164:43-50).

In particular, Witko et al., 2006 describes methods for producing recombinant DNA that includes:

(1) the preparation of a plasmid vector encoding T7 RNAP (pCMV-T7) by cloning the ORF into pCI-neo (Promega) 3' of the hCMV immediate-early promoter/enhancer region. Before insertion of the T7 RNAP ORF, pCI was modified to remove the T7 promoter located 5' of the multiple cloning site, generating vector pCI-neo-Bcl.

(2) The T7 RNAP gene was inserted into pCI-neo-Bcl using EcoRI and XbaI restriction sites incorporated into PCR primers used to amplify the T7 RNAP coding sequence. A Kozak consensus sequence was included 5' of the initiator ATG to provide an optimal sequence context for translation.

(3) Plasmids encoding viral trans-acting polypeptides were prepared by inserting the appropriate ORFs 3' of the T7 bacteriophage promoter and encephalomyocarditis viral internal ribosome entry site (IRES). The inserted coding sequences are flanked at the 3; end by a plasmid-encoded poly-A sequence and a T7 RNAP terminator. Plasmids encoding VSV N, P, L, M, and glycoprotein (G) were derived from the Indiana serotype genomic cDNA clone.

(4) Modified rVSV genomic clones were prepared using standard cloning procedures and the Indiana serotype pXN2 genomic cDNA clone as starting material. Genomic clones lacking the G gene (ΔG) were similar to those described by Roberts et al., 1999. A second type of G gene modification was constructed using the approach of Robinson and Whitt, 2000, in which the G coding sequence was replaced with a modified version that encodes only 18 amino-terminal (N-terminal) residues of the signal sequence fused to the C-terminal 91 amino acids of which approximately 42 residues forms a truncated extracellular domain (Gstem). In other VSV genomic clones, the N gene was translocated to the fourth genomic position by inserting the HIV-1 gag gene in the first position and inserting the N gene downstream between the M and G transcription units. These cDNA clones also contained modified G genes encoding truncated glycoproteins that contained only 1 (CT1) or 9 (CT9) amino acid C-terminal cytoplasmic tail. In some rVSV constructs, the G protein gene was replaced with the equivalent gene from the New Jersey Serotype.

(5) An expression vector encoding VSV G protein controlled by the hCMV promoter/enhancer (pCMV-G) was used to provide the glycoprotein in trans while propagating VSV-ΔG or VSV-Gstem vectors. The G protein coding sequence was cloned into the modified pCI-neo vector described above.

Furthermore, Witko et al., 2006 describes methods for virus rescue including:

(1) Helper-virus-free rescue initiated by calcium-phosphate transfection was performed in six-well plates containing 50-75% confluent monolayers. Vero, 293, or Hep-2 cells were fed 1-3 h prior to transfection with 4.5 ml of Complete DMEM per well and incubated at 32° C. in 3% CO2. DNA calcium-phosphate precipitates were formed in a 5 ml polypropylene tube by first preparing DNA mixtures composed of 2-5 µg of full-length genomic cDNA, 400 ng pT7-N (or NP), 300 ng pT7-P, 100 ng pT7-L, 10 µg of pCMV-T7 and nuclease-free sterile water to adjust the final volume to 225 µL. In many cases, 100-250 ng of supplementary support plasmids were included encoding M protein and viral glycoproteins, or additional trans-acting viral polypeptides such as the RSV M2 protein. The DNA solution was combined with 25 µL of 2.5M CaCl2, and subsequently, 250 µL of 2×BBS (280 mM NaCl, 50 mM BES, 1.5 mM sodium phosphate) was added dropwise while gently vortexing the tube. The mixture was incubated at room temperature 15-20 min to allow precipitate formation. The tube contents were then added dropwise to a single culture well after which the plate was rocked gently several times to evenly distribute the precipitate. Plates were incubated 3 h at 32° C. in 3% CO2, before being subjected to heat shock for 3 h in an incubator set to 43° C. and 3% CO2. Alternatively, if a 43° C. incubator was unavailable, plates were placed in a waterproof ziplock bag and submerged in a water bath for 3 h at 43° C. After heat shock was complete, plates were incubated overnight at 32° C. (3% CO2) at which time the cells were washed twice with herpes-buffered saline (20 mM herpes pH 7.0-7.4, 150 mM NaCl, 1 mM MgCl2) before adding 4 ml of Complete DMEM. The transfected cultures were incubated at 32° C. or 37° C. (5% CO2) for 48-72 h before the cells from each well were harvested with a cell scraper and transferred onto a 50% confluent monolayer of Vero cells (T25 or T75 flask) to establish a coculture that was incubated for 3-6 before replacing the medium. Incubation at 32° C. or 37° C. in 5% CO2 was continued until viral cytopathic effect (CPE) was evident. If the duration of coculture was extended, the medium was periodically replaced. Once CPE was abundant, virus in the cell supernatants was used to infect fresh monolayers from which seed stocks of recombinant virus were prepared. Amplified virus was used to infect monolayers that were subjected to histochemical staining to confirm virus identity.

(2) Virus rescue also was initiated after introduction of plasmid DNA into Vero cells by electroporation. Optimal conditions for electroporation were determined empirically beginning from conditions recommended for Vero cells by David Pasco in online Protocol 0368 (BTX Molecular Delivery Systems). For a single electroporation, Vero cells from a near-confluent monolayer (T150 flask) were detached in 4 ml of trypsin-EDTA (0.05% porcine trypsin, 0.02% EDTA; Invitrogen) and transferred to 30 ml of Medium I (DMEM containing 10% FBS, 220 µM tissue culture-grade 2-mercaptoethanol, 1% nonessential amino acids and 1% sodium pyruvate; components from Invitrogen) supplemented with 100 µg/ml of soybean trypsin inhibitor (Sigma) The cells were collected from the suspension by centrifugation at 300×g after which the pellet was resuspended in 10 m Medium II (Iscove's Modified Dulbecco's Medium containing 220_M 2-mercaptoethanol, 1% nonessential amino acids an 1% sodium pyruvate, 1% tissue-culture-grade DMSO; component from Invitrogen), which contains DMSO as recommended by Melkonyan et al. (Melkonyan et al., 1996), and 100 µg/ml of soybean trypsin inhibitor. The cells were washed a second time and resuspended in a final volume of 0.70 ml of Medium II (without trypsin inhibitor) equilibrated to room temperature. A 50 µL DNA solution prepared in nuclease-free water containing 50 µg pCMV-T7, 10-12 µg full-length viral cDNA, 8 µg pT7-N, 4 µg pT7-P, 1 µg pT7-L, and 1 µg each of applicable supplemental plasmids (i.e. matrix and glycoproteins) was added to the cell suspension before the mixture was transferred to an electroporation cuvette (4 mm gap; VWR or BTX). A BTX Square-Wav Electroporator (BTX ECM 820 or 830; BTX Molecular Deliver Systems) was used to pulse the cells (four times, 140-145V 70 ms) after which they were incubated at room temperature for approximately 5 min before 1 ml of Medium I was added and the cuvette contents were transferred to a sterile centrifuge tube containing 10 ml of Medium I. Electroporated cells were collected by centrifugation at 300×g for 5 min at room temperature and resuspended in 10 ml of Medium I before transfer to a T150 flask containing 25 ml of Medium I. The flask was incubated at 37° C. (5% CO2) for 3 h and then subjected to heat shock at 43° C. (3% or 5% CO2) for 3 h before the culture was incubated overnight (37° C. or 32° C., 5% CO2). The following day, the medium was replaced with 30 ml of Medium I supplemented with 50 µg/ml of gentamicin. For most rVSV rescues, incubation was continued with periodic medium changes until CPE was evident. For some attenuated rVSVs, rRSV-A and B, rMV, rMuV, rCDV, rhPIV3 or rbPIV3, a coculture step usually was required before CPE was evident. Coculture was initiated 48-72 h after electroporation by aspirating all but 10 ml of medium from the flask after which the cells were detached by scraping. The detached cells were pipetted multiple times to minimize the size of the cell aggregates and transferred to a flask containing an established 50%-confluent monolayer of Vero cells. Incubation was continued for 3-7 d with periodic medium changes until CPE was evident. To confirm virus rescue, supernatant from cultures exhibiting CPE was used to infect Vero cell monolayers in six-well plates. When CPE was evident, the cells were fixed with 4% formaldehyde prepared in PBS and subsequently permeabilized by treatment with 0.2% Triton X-100 (Sigma). Viral-specific antigens were detected by immunohistochemical staining with monoclonal or polyclonal antibodies. A modified coculture method was used for rescue of propagation-defective rVSV lacking a functional G protein. The coculture monolayer was prepared by first electroporating Vero cells with 50 µg pCMV-G expression vector, as described above, and allowing 24 h for expression of VSVG protein. The medium was replaced with 20 ml of Medium I containing 50 µg/ml of gentamicin before establishing the coculture.

To develop the VSV rescue system of Witko et al., 2006, a plasmid was constructed in which the T7 RNAP coding sequence was placed under the control of the hCMV transcriptional enhancer and promoter (pCMV-T7) and transfection optimization experiments were conducted with pCMV-T7 and a plasmid encoding luciferase under control of a T7 promoter and an IRES element. Calcium-phosphate transfection conditions that were found to maximize luciferase expression included heat shock treatment.

To promote efficient expression of the viral trans-acting polypeptides after transfection, a T7 promoter and an IRES element were used to control expression in the cell cytoplasm. Two factors were influential in the decision to use a cytoplasmic expression approach to supply the trans-acting proteins. One was simply that this strategy had been used successfully in earlier versions of the rescue procedure. The second was that this avoided the potential for unintended RNA processing that might occur in the nucleus during synthesis of mRNA by RNA polymerase II. Using an IRES element was important because RNA capping and methylation catalyzed by the vaccinia virus-encoded capping complex would not occur perhaps diminishing the efficiency of translation of protein coding transcripts synthesized by T7 RNA polymerase. The IRES was expected to compensate for the lack of a cap structure on transcripts synthesized by plasmid-encoded T7 RNAP.

The effect produced by expression of viral matrix protein and glycoproteins during rescue was examined. This was studied initially by conducting rMV rescue using HEp-2 cells and the established rescue system in which MVA-T7 provided T7 RNAP. Transfections were performed by the calcium-phosphate procedure and rescue efficiency was estimated by quantifying recombinant virus produced in the presence or absence of plasmids encoding MV M, F, and H proteins. In all but one experiment greater virus titers were achieved from transfected cells in which the M, F, and H plasmids were included. Significant enhancement in virus recovery resulted from expression of MV M, F, and H proteins leading to inclusion of analogous plasmids encoding viral matrix and glycoproteins in most subsequent rescue procedures.

The ultimate goal remained recovery of rVSV from Vero cells, because they are a more desirable substrate for vaccine production but achieved poor transfection efficiency. This led to consideration of electroporation as an alternative.

Electroporation conditions were optimized using pCMV-T7 and a reporter plasmid containing the luciferase gene linked to the T7 promoter and an IRES sequence. Once DNA uptake and expression was maximized, additional variables were examined that specifically influence rescue efficiency such as the ratio and quantities of expression plasmids encoding N, P, and L proteins, the effect of adding plasmids encoding VSVM and G proteins, and the potential benefit of heat shock. Using the electroporation/heat shock procedure, rVSV was recovered from Vero cells. The positive results obtained with rVSV were investigated further by attempting rescue with a variety of paramyxoviruses revealing that all those tested could be recovered from Vero cells.

The relatively rapid cytopathology produced by helper-virus might overwhelm the initial rescue and subsequent propagation of slow growing viruses such as those designed with multiple attenuating mutations or those that encode foreign proteins that hinder replication. To determine whether the helper-virus-free method facilitated rescue of growth-restricted viruses, recovery of several highly attenuated rVSV vectors encoding HIV gag was attempted. These vectors contained multiple attenuating modifications including: (1) gag gene insertion in the first position of the genome, which decreases expression of downstream cistrons; (2) truncation of the cytoplasmic domain of G protein; and (3) translocation of the N gene to genomic position 4. Rescue results revealed that these rVSV vectors were recovered efficiently and reproducibly from Vero cells with the helper-virus-free electroporation method. This indicated that viruses that were impaired significantly in their replicative capacity could be rescued effectively with this methodology.

The Vero cell electroporation method was modified further to allow recovery of propagation-defective rVSV. VSV recombinants that do not encode a functional glycoprotein, due either to truncation of the extracellular region (Gstem) or complete gene deletion (ΔG), are unable to propagate because they fail to express an attachment protein. VSV G protein was provided in trans during rescue (pT7-G) and coculture (pCMV-G) promoting rescue of rVSV-Luc4-ΔG and rVSV-Gstem from Vero cells.

The present invention also encompasses methods of producing or eliciting an immune response that may comprise administering to an animal, advantageously a mammal, any one of the herein disclosed recombinant VSV vectors.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, $F(ab')_2$, Fv and scFv which are capable of binding the epitope determinant. These antibody fragments retain some ability to selectively bind with its antigen or receptor and include, for example:

(i) Fab, the fragment which contains a monovalent antigen-binding fragment of an antibody molecule may be produced by digestion of whole antibody with the enzyme papain to yield an intact light chain and a portion of one heavy chain;

(ii) Fab', the fragment of an antibody molecule may be obtained by treating whole antibody with pepsin, followed by reduction, to yield an intact light chain and a portion of the heavy chain; two Fab' fragments are obtained per antibody molecule;

(iii) $F(ab')_2$, the fragment of the antibody that may be obtained by treating whole antibody with the enzyme pepsin without subsequent reduction; F(ab')2 is a dimer of two Fab' fragments held together by two disulfide bonds;

(iv) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid may be single-stranded, or partially or completely double-stranded (duplex). Duplex nucleic acids may be homoduplex or heteroduplex.

As used herein the term "transgene" may used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and IN sequences of the invention may be altered in these ways.

As regards codon optimization, the nucleic acid molecules of the invention have a nucleotide sequence that encodes the antigens of the invention and may be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens may be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention may readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87:2264-2268, modified as in Karlin & Altschul, Proc. Natl. Acad. Sci. USA 1993; 90:5873-5877.

Another example of a mathematical algorithm used for comparison of sequences is the algorithm of Myers & Miller, CABIOS 1988; 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 may be used. Yet another useful algorithm for identifying regions of local sequence similarity and alignment is the FASTA algorithm as described in Pearson & Lipman, Proc. Natl. Acad. Sci. USA 1988; 85:2444-2448.

Advantageous for use according to the present invention is the WU-BLAST (Washington University BLAST) version 2.0 software. WU-BLAST version 2.0 executable programs for several UNIX platforms may be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266:460-480; Altschul et al., Journal of Molecular Biology 1990; 215:403-410; Gish & States, 1993; Nature Genetics 3:266-272; Karlin & Altschul, 1993; Proc. Natl. Acad. Sci. USA 90:5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" may be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention may be under the control of a constitutive promoter or of an inducible promoter, which initiates transcription only when exposed to some particular external stimulus, such as, without limitation, antibiotics such as tetracycline, hormones such as ecdysone, or heavy metals. The promoter may also be specific to a particular cell-type, tissue or organ. Many suitable promoters and enhancers are known in the art, and any such suitable promoter or enhancer may be used for expression of the transgenes of the invention. For example, suitable promoters and/or enhancers may be selected from the Eukaryotic Promoter Database (EPDB).

The present invention relates to a recombinant vesicular stomatitis virus (VSV) vector expressing a foreign epitope. Advantageously, the epitope is an HIV epitope. Any HIV epitope may be expressed in a VSV vector. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707 5,698,178; 5,688,914; 5,686,078; 5,681,831; 5,679,784; 5,674,984; 5,672,472; 5,667,964; 5,667,783; 5,665,536; 5,665,355;

5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610; 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

Advantageously, the HIV epitope may be an Env precursor or gp160 epitope. The Env precursor or gp160 epitope may be recognized by antibodies PG9, PG16, 2G12, b12, 2F5, 4E10, Z13, or other broad potent neutralizing antibodies.

In another embodiment, HN, or immunogenic fragments thereof, may be utilized as the HIV epitope. For example, the HN nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the antigens and/or antibodies of the invention may be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector may be used depending on the application. For example, plasmids, viral vectors, bacterial vectors, protozoan vectors, insect vectors, baculovirus expression vectors, yeast vectors, mammalian cell vectors, and the like, may be used. Suitable vectors may be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses may be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and may be used as gene delivery vectors.

The present invention relates to recombinant vesicular stomatitis (VSV) vectors, however, other vectors may be contemplated in other embodiments of the invention such as, but not limited to, prime boost administration which may comprise administration of a recombinant VSV vector in combination with another recombinant vector expressing one or more HIV epitopes.

VSV is a very practical, safe, and immunogenic vector for conducting animal studies, and an attractive candidate for developing vaccines for use in humans. VSV is a member of the Rhabdoviridae family of enveloped viruses containing a nonsegmented, negative-sense RNA genome. The genome is composed of 5 genes arranged sequentially 3'-N—P-M-G-L-5', each encoding a polypeptide found in mature virions. Notably, the surface glycoprotein G is a transmembrane polypeptide that is present in the viral envelope as a homotrimer, and like Env, it mediates cell attachment and infection.

The VSVs of U.S. Pat. Nos. 7,468,274; 7,419,829; 7,419,674; 7,344,838; 7,332,316; 7,329,807; 7,323,337; 7,259,015; 7,244,818; 7,226,786; 7,211,247; 7,202,079; 7,198,793; 7,198,784; 7,153,510; 7,070,994; 6,969,598; 6,958,226; RE38,824; PP15,957; 6,890,735; 6,887,377; 6,867,326; 6,867,036; 6,858,205; 6,835,568; 6,830,892; 6,818,209; 5 6,790,641; 6,787,520; 6,743,620; 6,740,764; 6,740,635; 6,740,320; 6,682,907; 6,673,784; 6,673,572; 6,669,936; 6,653,103; 6,607,912; 6,558,923; 6,555,107; 6,533,855; 6,531,123; 6,506,604; 6,500,623; 6,497,873; 6,489,142; 6,410,316; 6,410,313; 6,365,713; 6,348,312; 6,326,487; 6,312,682; 6,303,331; 6,277,633; 6,207,455; 6,200,811; 6,190,650; 6,171,862; 6,143,290; 6,133,027; 6,121,434; 6,103,462; 6,069,134; 6,054,127; 6,034,073; 5,969,211; 10 5,935,822; 5,888,727; 5,883,081; 5,876,727; 5,858,740; 5,843,723; 5,834,256; 5,817,491; 5,792,604; 5,789,229; 5,773,003; 5,763,406; 5,760,184; 5,750,396; 5,739,018; 5,698,446; 5,686,279; 5,670,354; 5,540,923; 5,512,421; 5,090,194; 4,939,176; 4,738,846; 4,622,292; 4,556,556 and 4,396,628 may be contemplated by the present invention.

The nucleotide sequences and vectors of the invention may be delivered to cells, for example if the aim is to express HIV-1 antigens in cells in order to produce and isolate the expressed proteins, such as from cells grown in culture. For expressing the antibodies and/or antigens in cells any suitable transfection, transformation, or gene delivery methods may be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens may be carried out in any suitable type of host cells, such as bacterial cells, yeast, insect cells, and mammalian cells. The antibodies and/or antigens of the invention may also be expressed including using in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition which may comprise the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition may also be formulated in the form of an oil-in-water emulsion. The oil-in-water emulsion may be based, for example, on light liquid paraffin oil (European Pharmacopeia type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers may be non-ionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant may be a mixture of emulsifier(s), micelle-forming agent, and oil such as that which is commercially available under the name Provax® (IDEC Pharmaceuticals, San Diego, CA).

The immunogenic compositions of the invention may contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., AlK(SO$_4$)$_2$, AlNa(SO$_4$)$_2$, AlNH(SO$_4$)$_2$, silica, alum, Al(OH)$_3$, Ca3(PO$_4$)$_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71 (3): 538-44; Ahmad-Nejad, P. et al (2002) Eur. J. Immunol. 32 (7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20 (29-30): 3498-508), Juva Vax™ (U.S. Pat. No. 6,693,086), certain natural substances (e.g., wax D from *Mycobacterium tuberculosis*, substances found in *Corynebacterium parvum, Bordetella pertussis*, or members of the genus *Brucella*), flagellin (Toll-like receptor 5 ligand; see McSorley, S. J. et al (2002) J. Immunol. 169 (7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22 (13-14): 1791-8), and the CCR5 inhibitor CMPD167 (see Veazey, R. S. et al (2003) J. Exp. Med. 198:1551-1562).

Aluminum hydroxide or phosphate (alum) are commonly used at 0.05 to 0.1% solution in phosphate buffered saline. Other adjuvants that may be used, especially with DNA vaccines, are cholera toxin, especially CTA1-DD/ISCOMs (see Mowat, A. M. et al (2001) J. Immunol. 167 (6): 3398-405), polyphosphazenes (Allcock, H. R. (1998) App. Organometallic Chem. 12 (10-11): 659-666; Payne, L. G. et al (1995) Pharm. Biotechnol. 6:473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77 (3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which may be administered either as proteins or in the form of DNA, on the same expression vectors as those encoding the antigens of the invention or on separate expression vectors.

In an advantageous embodiment, the adjuvants may be lecithin is combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions may be designed to introduce the nucleic acids or expression vectors to a desired site of action and release it at an appropriate and controllable rate. Methods of preparing controlled-release formulations are known in the art. For example, controlled release preparations may be produced by the use of polymers to complex or absorb the immunogen and/or immunogenic composition. A controlled-release formulation may be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention may be readily determined by those of skill in the art. For example, the dosage of the immunogens may vary depending on the route of administration and the size of the subject. Suitable doses may be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions may serve to provide protective immunity of a subject against HIV-1 infection or to prevent or attenuate the progression of AIDS in a subject already infected with HIV-1. When provided therapeutically, the immunogenic compositions may serve to ameliorate and treat AIDS symptoms and are advantageously used as soon after infection as possible, preferably before appearance of any symptoms of AIDS but may also be used at (or after) the onset of the disease symptoms.

The immunogenic compositions may be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12:1529-1533; Xiang et al., (1994) Virology 199:132-140; Webster et al., (1994) Vaccine 12:1495-1498; Davis et al., (1994) Vaccine 12:1503-1509; and Davis et al., (1993) Hum. Mol. Gen. 2:1847-1851), or intradermal injection of DNA using "gene gun" technology (Johnston et al., (1994) Meth. Cell Biol. 43:353-365). Alternatively, delivery routes may be oral, intranasal or by any other suitable route. Delivery may also be accomplished via a mucosal surface such as the anal, vaginal or oral mucosa. Immunization schedules (or regimens) are well known for animals (including humans) and may be readily determined for the particular subject and immunogenic composition. Hence, the immunogens may be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response may also include administration of an adjuvant with the immunogens. In some instances, annual, biannual or other long interval (5-10 years) booster immunization may supplement the initial immunization protocol.

The present methods also include a variety of prime-boost regimens, for example DNA prime-VSV boost regimens. In these methods, one or more priming immunizations are followed by one or more boosting immunizations. The actual immunogenic composition may be the same or different for each immunization and the type of immunogenic composition (e.g., containing protein or expression vector), the route, and formulation of the immunogens may also be varied. For example, if an expression vector is used for the priming and boosting steps, it may either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

The prime-boost regimen may also include VSV vectors that derive their G protein or G/Stem protein from different serotype vesicular stomatitis viruses (Rose N F, Roberts A, Buonocore L, Rose J K. Glycoprotein exchange vectors based on vesicular stomatitis virus allow effective boosting and generation of neutralizing antibodies to a primary isolate of human immunodeficiency virus type 1. J Virol. 2000 December; 74 (23): 10903-10). The VSV vectors used in these examples contain a G or G/Stem protein derived from the Indiana serotype of VSV. Vectors may also be constructed to express G or G/Stem molecules derived from other VSV serotypes (i.e. vesicular stomatitis New Jersey virus or vesicular stomatitis Alagoas virus) or other vesiculoviruses (i.e. Chandipura virus, Cocal virus, Isfahan virus). Thus a prime may be delivered in the context of a G or G/Stem molecule that is from the Indiana serotype and the immune system may be boosted with a vector that expresses epitopes in the context of second serotype like New Jersey. This circumvents anti-G immunity elicited by the prime, and helps focus the boost response against the foreign epitope.

A specific embodiment of the invention provides methods of inducing an immune response against HIV in a subject by administering an immunogenic composition of the invention, preferably which may comprise an VSV vector containing RNA encoding one or more of the epitopes of the invention, one or more times to a subject wherein the epitopes are expressed at a level sufficient to induce a specific immune response in the subject. Such immunizations may be repeated multiple times at time intervals of at least 2, 4 or 6 weeks (or more) in accordance with a desired immunization regime.

The immunogenic compositions of the invention may be administered alone, or may be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages may be determined taking into consideration such factors as the age, sex, weight, species and condition of the particular subject, and the route of administration.

When used in combination, the other HIV immunogens may be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which may be administered as a protein, on a plasmid (e.g., pTHr.HIVA) or in a viral vector (e.g., MVA.HIVA). Another such HIV immunogen is RENTA (described in PCT/US2004/037699), which may also be administered as a protein, on a plasmid (e.g., pTHr.RENTA) or in a viral vector (e.g., MVA.RENTA).

For example, one method of inducing an immune response against HIV in a human subject may comprise administering at least one priming dose of an HIV immunogen and at least one boosting dose of an HIV immunogen, wherein the immunogen in each dose may be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response may include an HIV-specific T-cell immune response or an HIV-specific B-cell immune response. Such immunizations may be done at intervals, preferably of at least 2-6 or more weeks.

It is to be understood and expected that variations in the principles of invention as described above may be made by one skilled in the art and it is intended that such modifications, changes, and substitutions are to be included within the scope of the present invention.

The invention will now be further described by way of the following non-limiting examples.

EXAMPLES

Example 1: Recombinant VSV Vector Construction

Structure of the IA VI VSV genomic clone as depicted in FIG. 1.
Features include:
1. The cloning vector is based on pSP72 (Genbank X65332 2).
2. The extended T7 promoter is PT7-g10 described by Lopez et al. (Lopez et al., 1997. Journal of molecular biology 269:41-51)
3. The hammerhead ribozyme was designed following the rules for constructing self-cleaving RNA sequences (Inoue et al. 2003. J Virol Methods 107:229-236 and Ruffner et al. 1990. Biochemistry 29:10695-10702).
4. The hepatitis delta virus ribozyme and T7 RNA polymerase terminator were used as described before for the measles virus rescue system (Radecke et al. 1995. The EMBO journal 14:5773-5784, 23 and Sidhu et al. 1995. Virology 208:800-807)
5. Unique restriction endonuclease cleavage sites in the recombinant VSV genome (red) are indicated above the genome map.
6. The Leader and Trailer are cis-acting sequences in the termini that control mRNA synthesis and replication.
7. The viral proteins N, nucleocapsid; P. phosphoprotein; M, matrix; G, glycoprotein; L, large protein.

Recombinant VSV Vector Construction
Indiana Serotype
Based on Genbank EF197793-modified as described below:
Nucleotide substitutions introduced to generate unique restriction sites or bring sequence closer to consensus
  1371 CA>GC (NheI)
  After 2195 insert TAG (SpeI) (all genome numbers below adjusted to include +3 bp introduced by this insertion)
  3036 G>T improves match to consensus transcription stop signal
  3853 X>A (X was an ambiguity in Genbank file)
  4691 T>A to generate PacI
  7546 C>A silent change in L coding sequence eliminates a BstBI site
  1960 TAC>TCC to change Y>S
  3247 GTA>ATA to change V>I
  3729 AAG>GAG to change K>E
  4191 GTA>GAA to change V>E
  4386 GGT>GAT to change G>D
  4491 ACC>ATC to change T>I
  5339 ATT>CTT to change I>L
  5834 ACT>GCT to change T>A
  10959 AGA>AAA to change R>K A VSV genome and cloning fragments are depicted in FIGS. 2A-G.

TABLE 1

Modifications introduced into the VSV genomic sequence (Genbank accession EF197793) are listed. Note that Line 3 includes a 3 base insertion, which shifts numbering in the recombinant genomic clone (rEF197793). If nucleotide substitutions were introduced to change amino acid coding, the base change in the codon is indicated in red.

| | Nucleotide position in EF197793 | Nucleotide position in rEF197793 | Nucleotide Change | Purpose |
|---|---|---|---|---|
| 1 | Substitution 1371-2 | Substitution 1371-2 | CA > GC | Creates a unique NheI cleavage site between N and P gens |
| 2 | Substitution 1960-2 | Substitution 1960-2 | TAC > TCC | Y > S substitution in P protein amino acid sequence to agree with consensus. |
| 3 | Insert after 2195 | 3 base insert after 2195 | Insert TAG | Creates a unique SpeI site between P and M genes |
| 4 | Substitution 3039 | Substitution 3042 | G > T | Improves agreement with consensus. Also improves agreement with consensus transcription stop signal |
| 5 | Substitution 3234-6 | Substitution 3237-9 | GTA > ATA | V > I substitution in P protein amino acid sequence to agree with consensus. |
| 6 | Substitution 3729-31 | Substitution 3732-34 | AAG > GAG | K > E substitution in G protein amino acid sequence to agree with consensus. |

TABLE 1-continued

Modifications introduced into the VSV genomic sequence (Genbank accession EF197793) are listed. Note that Line 3 includes a 3 base insertion, which shifts numbering in the recombinant genomic clone (rEF197793). If nucleotide substitutions were introduced to change amino acid coding, the base change in the codon is indicated in red.

| | Nucleotide position in EF197793 | Nucleotide position in rEF197793 | Nucleotide Change | Purpose |
|---|---|---|---|---|
| 7 | Substitution 3856 | Substitution 3859 | N > A | Replace unknown base in Genbank file with consensus |
| 8 | Substitution 4191-93 | Substitution 4194-6 | GTA > GAA | V > E substitution in G protein amino acid sequence to agree with consensus. |
| 9 | Substitution 4386-88 | Substitution 4389-92 | GGT > GAT | G > D substitution in G protein amino acid sequence to agree with consensus. |
| 10 | Substitution 4491-93 | Substitution 4494-96 | ACC > ATC | T > I substitution in G protein amino acid sequence to agree with consensus. |
| 11 | Substitution 4694 | Substitution 4697 | T > A | Creates unique PacI cleavage site between G and L genes |
| 12 | Substitution 5339-41 | Substitution 5342-44 | ATT > CTT | I > L substitution in L protein amino acid sequence to agree with consensus. |
| 13 | Substitution 5834-6 | Substitution 5837-40 | ACT > GCT | T > A substitution in L protein amino acid sequence to agree with consensus. |
| 14 | Substitution 10959-61 | Substitution 10962-64 | AGA > AAA | R > K substitution in L protein amino acid sequence to agree with consensus. |
| 15 | Substitution 7546 | Substitution 7549 | C > A | Eliminates a BstBI site in the L gene sequence making the BstBI site between the M and G genes unique. This substitution was silent for amino acid coding. |

```
Genbank X65332.2: Cloning vector pSP72
LOCUS       X65332             2462 bp    DNA       circular SYN 25-JAN-
2000
DEFINITION  Cloning vector pSP72.
ACCESSION   X65332
VERSION     X65332.2 GI:6759494
KEYWORDS    beta-lactamase; bla gene; cloning vector; multiple cloning site;
            promoter.
SOURCE      Cloning vector pSP72
  ORGANISM  Cloning vector pSP72
            other sequences; artificial sequences; vectors.
REFERENCE   1
  AUTHORS   Technical,Services.
  TITLE     Direct Submission
  JOURNAL   Submitted (23-MAR-1992) Technical Services, Promega Corporation,
            2800 Woods Hollow Road, Madison, Wi 53711-5399, USA
  REMARK    revised by [2]
REFERENCE   2
  AUTHORS   Technical,Services.
  TITLE     Direct Submission
  JOURNAL   Submitted (28-MAY-1993) Technical Services, Promega Corporation,
            2800 Woods Hollow Road, Madison, Wi 53711-5399, USA
  REMARK    revised by [3]
REFERENCE   3 (bases 1 to 2462)
  AUTHORS   Technical,Services.
  TITLE     Direct Submission
  JOURNAL   Submitted (12-JAN-2000) Technical Services, Promega Corporation,
            2800 Woods Hollow Road, Madison, Wi 53711-5399, USA
COMMENT     On Jan 26, 2000 this sequence version replaced gi:58239.
            See X65300-X65335 for related vector sequences
            This vector can be obtained from Promega Corporation, Madison, WI
            Call one of the following numbers for order or technical
            information:
            Order or Technical 800-356-9526
            In Wisconsin       800-356-9526
            Outside U.S.       608-274-4330.
```

```
FEATURES             Location/Qualifiers
     source          1..2462
                     /organism="Cloning vector pSP72"
                     /mol_type="other DNA"
                     /db_xref="taxon:90137"
     promoter        join(2446..2462,1..3)
                     /note="SP6 promoter"
     misc_feature    1
                     /note="SP6 transcription initiation site"
     misc_feature    4..90
                     /note="multiple cloning sites"
     promoter        99..118
                     /note="T7 promoter"
     misc_feature    101
                     /note="T7 transcription initiation site"
     gene            complement(1135..1995)
                     /gene="bla"
     CDS             complement(1135..1995)
                     /gene="bla"
                     /codon_start=1
                     /transl_table=11
                     /product="Beta-lactamase"
                     /protein_id="CAA46432.1"
                     /db_xref="GI:58240"
/translation="MSIQHFRVALIPFFAAFCLPVFAHPETLVKVKDAEDQLGARVGY
IELDLNSGKILESFRPEERFPMMSTFKVLLCGAVLSRIDAGQEQLGRRIHYSQNDLVE
YSPVTEKHLTDGMTVRELCSAAITMSDNTAANLLLTTIGGPKELTAFLHNMGDHVTRL
DRWEPELNEAIPNDERDTTMPVAMATTLRKLLTGELLTLASRQQLIDWMEADKVAGPL
LRSALPAGWFIADKSGAGERGSRGIIAALGPDGKPSRIVVIYTTGSQATMDERNRQIA
EIGASLIKHW" (SEQ ID NO: 1)

ORIGIN
        1 gaactcgagc agctgaagct tgcatgcctg caggtcgact ctagaggatc cccgggtacc
       61 gagctcgaat tcatcgatga tatcagatct gccggtctcc ctatagtgag tcgtattaat
      121 ttcgataagc caggttaacc tgcattaatg aatcggccaa cgcgcgggga gaggcggttt
      181 gcgtattggg cgctcttccg cttcctcgct cactgactcg ctgcgctcgg tcgttcggct
      241 gcggcgagcg gtatcagctc actcaaaggc ggtaatacgg ttatccacag aatcagggga
      301 taacgcagga aagaacatgt gagcaaaagg ccagcaaaag gccaggaacc gtaaaaaggc
      361 cgcgttgctg gcgtttttcc ataggctccg cccccctgac gagcatcaca aaaatcgacg
      421 ctcaagtcag aggtggcgaa acccgacagg actataaaga taccaggcgt ttccccctgg
      481 aagctccctc gtgcgctctc ctgttccgac cctgccgctt accggatacc tgtccgcctt
      541 tctcccttcg ggaagcgtgg cgctttctca tagctcacgc tgtaggtatc tcagttcggt
      601 gtaggtcgtt cgctccaagc tgggctgtgt gcacgaaccc cccgttcagc ccgaccgctg
      661 cgccttatcc ggtaactatc gtcttgagtc aacccggta agacacgact tatcgccact
      721 ggcagcagcc actggtaaca ggattagcag agcgaggtat gtaggcggtg ctacagagtt
      781 cttgaagtgg tggcctaact acggctacac tagaagaaca gtatttggta tctgcgctct
      841 gctgaagcca gttaccttcg gaaaaagagt tggtagctct tgatccggca aacaaaccac
      901 cgctggtagc ggtggttttt tgtttgcaa gcagcagatt acgcgcagaa aaaaggatc
      961 tcaagaagat cctttgatct tttctacggg gtctgacgct cagtggaacg aaaactcacg
     1021 ttaagggatt ttggtcatga gattatcaaa aaggatcttc acctagatcc ttttaaatta
     1081 aaaatgaagt tttaaatcaa tctaaagtat atatgagtaa acttggtctg acagttacca
     1141 atgcttaatc agtgaggcac ctatctcagc gatctgtcta tttcgttcat ccatagttgc
     1201 ctgactcccc gtcgtgtaga taactacgat acgggagggc ttaccatctg gccccagtgc
     1261 tgcaatgata ccgcgagacc cacgctcacc ggctccagat ttatcagcaa taaaccagcc
     1321 agccggaagg gccgagcgca gaagtggtcc tgcaacttta tccgcctcca tccagtctat
     1381 taattgttgc cgggaagcta gagtaagtag ttcgccagtt aatagtttgc gcaacgttgt
     1441 tgccattgct acaggcatcg tggtgtcacg ctcgtcgttt ggtatggctt cattcagctc
```

-continued

```
1501    cggttcccaa cgatcaaggc gagttacatg atcccccatg ttgtgcaaaa aagcggttag 1561    ctccttcggt cctccgatcg ttgtcagaag taagttggcc gcagtgttat cactcatggt 1621    tatggcagca ctgcataatt ctcttactgt catgccatcc gtaagatgct tttctgtgac 1681    tggtgagtac tcaaccaagt cattctgaga atagtgtatg cggcgaccga gttgctcttg 1741    cccggcgtca atacgggata ataccgcgcc acatagcaga actttaaaag tgctcatcat 1801    tggaaaacgt tcttcggggc gaaaactctc aaggatctta ccgctgttga gatccagttc 1861    gatgtaaccc actcgtgcac ccaactgatc ttcagcatct tttactttca ccagcgtttc 1921    tgggtgagca aaacaggaa ggcaaaatgc cgcaaaaaag gaataaggg cgacacggaa 1981    atgttgaata ctcatactct tcctttttca atattattga agcatttatc agggttattg 2041    tctcatgagc ggatacatat ttgaatgtat ttagaaaaat aaacaaatag gggttccgcg 2101    cacatttccc cgaaaagtgc cacctgacgt ctaagaaacc attattatca tgacattaac 2161    ctataaaaat aggcgtatca cgaggccctt tcgtctcgcg cgtttcggtg atgacggtga 2221    aaacctctga cacatgcagc tcccggagac ggtcacagct tgtctgtaag cggatgccgg 2281    gagcagacaa gcccgtcagg gcgcgtcagc gggtgttggc gggtgtcggg gctggcttaa 2341    ctatgcggca tcagagcaga ttgtactgag agtgcaccat atggacatat tgtcgttaga 2401    acgcggctac aattaataca taaccttatg tatcatacac atacgattta ggtgacacta 2461    ta// (SEQ ID NO: 2)
```

```
Genbank EF197793: Vesicular stomatitis Indiana virus, complete genome
LOCUS       EF197793               11161 bp    cRNA    linear   VRL 15-APR-
2007
DEFINITION  Vesicular stomatitis Indiana virus, complete genome.
ACCESSION   EF197793
VERSION     EF197793.1 GI:144678900
SOURCE      Vesicular stomatitis Indiana virus
ORGANISM    Vesicular stomatitis Indiana virus
            Viruses; ssRNA negative-strand viruses; Mononegavirales;
            Rhabdoviridae; Dimarhabdovirus supergroup; Vesiculovirus.
REFERENCE   1 (bases 1 to 11161)
  AUTHORS   Remold,S.K., Rambaut,A. and Turner,P.T.
  TITLE     Evolutionary genomics of host adaptation in Vesicular stomatitis
            virus
  JOURNAL   Unpublished
REFERENCE   2 (bases 1 to 11161)
  AUTHORS   Remold,S.K.
  TITLE     Direct Submission
  JOURNAL   Submitted (22-DEC-2006) Biology, University of Louisville, 139
Life Sciences Building, Louisville, KY 40292, USA
FEATURES             Location/Qualifiers
     source          1..11161
                     /organism="Vesicular stomatitis Indiana virus"
                     /mol_type="viral cRNA"
                     /isolate="MARMC from S.F. Elena Lab, 2001"
                     /db_xref="taxon:11277"
                     /country="USA"
     gene            51..1376
                     /gene="N"
     CDS             64..1332
                     /gene="N"
                     /codon_start=1
                     /product="nucleoprotein"
                     /protein_id="ABP01780.1"
                     /db_xref="GI:144678901"
/translation="MSVIVKRIIDNIVIVPKLPANEDPVEYPADYFRKSKEIPLYINT
TKSLSDLRGYVYQGLKSGNVSIIHVNSYLYGALKDIRGKLDKDWSSEGINIGKAGDTI
GIFDLVSLKALDGVLPDGVSDASRTSADDKWLPLYLLGLYRVGRTQMPEYRKRLMDGL
TNQCKMINEQFEPLVPEGRDIFDVWGNDSNYTKIVAAVDMFEHMFKKHECASFRYGTI
VSRFKDCAALATFGHLCKITGMSTEDVTTWILNREVADEMVQMMLPGQEIDKADSYMP
YLIDFGLSSKSPYSSVKNPAFHFWGQLTALLLRSTRARNARQPDDIEYTSLTTAGLLY
AYAVGSSADLAQQFCVGDSKYTPDDSTGGLTTNAPPQGRDVVEWLGWFEDQNRKPTPD
MMQYAKRAVMSLQGLREKTIGKYAKSEFDK" (SEQ ID NO: 3)
```

-continued

```
     gene            1386..2199
                     /gene="P"
     CDS             1396..2193
                     /gene="P"
                     /codon_start=1
                     /product="phosphoprotein"
                     /protein_id="ABP01781.1"
                     /db_xref="GI:144678902"
/translation="MDNLTKVREYLKSYSRLDQAVGEIDEIEAQRAEKSNYELFQEDG
VEEHTRPSYFQAADDSDTESEPEIEDNQGLYVPDPEAEQVEGFIQGPLDDYADEDVDV
VFTSDWKQPELESDEHGKTLRLTLPEGLSGEQKSQWLLTIKAVVQSAKHWNLAECTFE
ASGEGVIIKKRQITPDVYKVTPVMNTHPYQSEAVSDVWSLSKTSMTFQPKKASLQPLT
ISLDELFSSRGEFISVGGNGRMSHKEAILLGLRYKKLYNQARVKYSL" (SEQ ID NO: 4)
     gene            2209..3039
                     /gene="M"
     CDS             2250..2939
                     /gene="M"
                     /codon_start=1
                     /product="matrix"
                     /protein_id="ABP01782.1"
                     /db_xref="GI:144678903"
/translation="MSSLKKILGLKGKGKKSKKLGIAPPPYEEDTNMEYAPSAPIDKS
YFGVDEMDTHDPNQLRYEKFFFTVKMTVRSNRPFRTYSDVAAAVSHWDHMYIGMAGKR
PFYKILAFLGSSNLKATPAVLADQGQPEYHAHCEGRAYLPHRMGKTPPMLNVPEHFRR
PFNIGLYKGTIELTMTIYDDESLEAAPMIWDHENSSKFSDFREKALMFGLIVEKKASG
AWVLDSVSHFK" (SEQ ID NO: 5)
     gene            3049..4713
                     /gene="G"
     CDS             3078..4613
                     /gene="G"
                     /codon_start=1
                     /product="glycoprotein"
                     /protein_id="ABP01783.1"
                     /db_xref="GI:144678904"
/translation="MKCLLYLAFLFIGVNCKFTIVEPHNQKGNWKNVPSNYHYCPSSS
DLNWHNDLVGTALQVKMPKSHKAIQADGWMCHASKWVTTCDFRWYGPKYITHSIRSFT
PSVEQCKESIEQTKQGTWLNPGFPPQSCGYATVTDAEAAIVQVTPHHVLVDEYTGEWV
DSQFINGKCSNDICPTVHNSTTWHSDYKVKGLCDSNLISMDITFFSEDGELSSLGKKG
TGFRSNYFAYETGDKACKMQYCKHWGVRLPSGVWFEMADKXLFAAARFPECPEGSSIS
APSQTSVDVSLIQDVERILDYSLCQETWSKIRAGLPISPVDLSYLAPKNPGTGPVFTI
INGTLKYFETRYIRVDIAAPILSRMVGMISGTTTERVLWDDWAPYEDVEIGPNGVLRT
SSGYKFPLYMIGHGMLDSDLHLSSKAQVFEHPHIQDAASQLPDGETLFFGDTGLSKNP
IEFVEGWFSSWKSSIASFFFTIGLIIGLFLVRVGIYLCIKLKHTKKRQIYTDIEMNR
LGK" (SEQ ID NO: 6)
     gene            4723..11095
                     /gene="L"
     CDS             4733..11062
                     /gene="L"
                     /codon_start=1
                     /product="large protein"
                     /protein_id="ABP01784.1"
                     /db_xref="GI:144678905"
/translation="MEVHDFETDEFNDFNEDDYATREFLNPDERMTYLNHADYNLNSP
LISDDIDNLIRKFNSLPIPSMWDSKNWDGVLEMLISCQANPISTSQMHKWMGSWLMSD
NHDASQGYSFLHEVDKEAEITFDVVETFIRGWGNKPIEYIKKERWIDSFKILAYLCQK
FLDLHKLTILNAVSEVELLNLARTFKGKVRRSSHGTNICRIRVPSLGPTFISEGWAY
FKKLDILMDRNFLLMVKDVIIGRMQTVLSMVCRIDNLFSEQDIFSLLNIYRIGDKIVE
RQGNFSYDLIKMVEPICNLKLMKLARESRPLVPQFPHFENHIKTSVDEGAKIDRGIRF
LHDQIMSVKIVDLTLVIYGSFRHWGHPFIDYYTGLEKLHSQVIMKKDIDVSYAKALAS
DLARIVLFQQFNDHKKWFVNGDLLPHDHPFKSHVKENTWPTAAQVQDFGDKWHELPLI
KCFEIPDLLDPSIIYSDKSHSMNRSEVLKHVRMNPNIPIPSKKVLQTMLDTKATNWKE
FLKEIDEKGLDDDDLIIGLKGKERELKLAGRFFSLMSWKLREYFVITEYLIKTHFVPM
FKGLIMADDLTAVIKKMLDSSSGQGLKSYEAICIANHIDYEKWNNHQRKLSNGPVERV
MGQFLGYPSLIERTHEFFEKSLIYNGRPDLMRVHNNTLINSTSQRVCWQGQEGGLEG
LRQKGWSILNLLVIQREAKIRNTAVKVLAQGDNQVICTQYKIKKSRNVVELQGALNQM
VSNNEKIMTAIKIGIGKLGLLINDDETMQSADYLNYGKIPIFRGVIRGLETKRWSRVT
CVINDQIPTCANIMSSVSTNALTVAHFAENPINAMIQYNYFGTFARLLLMMHDPALRQ
SLYEVQDKIPGLHSSTFKYAMLYLDPSIGGVSGMSLSRFLIRAFPDPVTESLSFWRFI
HVHARSEHLKEMSAVFGNPEIAKFRITHIDKLVEDPISLNIAMGMSPANLLKTEVKKC
LIESRQTIRNQVIKDATIYLYHEEDRLRSFLWSINPLFPRFLSEFKSGTFLGVADGLI
SLFQNSRTIRNSFKKKYHRELDDLIVRSEVSSLTHLGKLHLRRGSCKMWTCSATHADT
LRYKSWGRIVIGTIVPHPLEMLGPQHRKETPCAPCNTSGFNYVSVHCPDGIHDVFSSR
GPLPAYLGSKTSESTSILQPWERESKVPLIKRATRLRDAISWFVEPDSKLAMTILSNI
HSLTGEEWTKRQHGFKRTGSALHRFSTSRMSHGGFASQSTAALTRLMATTDTMRDLGD
QNFDFLFQATLLYAQITTIVARDGWITSCIDHYHIACKSCLRPIEEITLDSSMDYIPP
DVSHVLKTWRNGEGSWGQEIKQIYPLEGNWKNLAPAEQSYQVGRCIGFLYGDLAYRKS
THAEDSSLFPLSIQGRIRGRGFLKGLLDGLMRASCCQVIHRRSLAHLKRPANAVYGGL
IYLIDKLSVSPPFLSLIRSGPIRDELETIPHKIPTSYPTSNRDMGVIVRNYFKYQCRL
IEKGKYRSHYSQLWLFSDVLSIDFIGPFSISTILLQILYKPFLSGKDKNELRELANLS
SLLRSGEGWEDIHVKFFIKDILLCPEEIRHACKFGIAKDNNKDMSYPPWGRESRGTIT
TIPVYYTTIPYPKMLEMPPRIQNPLLSGIRLGQLPTAHYKIRSILHGMGIHYRDFLS
```

-continued
```
CGDGSGGMTAALLRENVHSRGIFNSLLELSGSVMRGASPEPPSALETLGGDKSRCVNG
ETCWEYPSDLCDPRTWDYFLRLKAGLGLQIDLIVMDMEVRDSSTSLKIETNVRNYVHR
ILDEQGVLIYKTYGTYICESEKNAVTILGPMFKIVDLVQTEFSSSQTSEVYMVCKGLK
KLIDEPNPDWSSINESWKNLYAFQSSEQEFARAKKVSTYFTLIGIPSQFIPDPFVNIE
TMLQIFGVPIGVSHAAALKSSDRPADLLTISLFYMAIISYYNINHIRVGPIPPNPPSD
GIAQNVGIAITGISFWLSLMEKDIPLYQQCLAVIQQSFPIRWEAVSVKGGYKQKWSTR
GDGLPKDTRISDSLAPIGNWIRSLELVRNQVRLNPFNEILFNQLCRIVDNHLKWSNLR
RNTGMIEWINRRISKEDRSILMLKSDLHEENSWRD" (SEQ ID NO: 7)
```

ORIGIN
```
        1 acgaagacaa acaaaccatt attatcatta aaaggctcag gagaaacttt aacagtaatc
       61 aaaatgtctg ttacagtcaa gagaatcatt gacaacacag tcatagttcc aaaacttcct
      121 gcaaatgagg atccagtgga atacccggca gattacttca gaaaatcaaa ggagattcct
      181 ctttacatca atactacaaa aagtttgtca gatctaagag atatgtcta ccaaggcctc
      241 aaatccggaa atgtatcaat catacatgtc aacagctact tgtatggagc attgaaggac
      301 atccggggta agttggataa agattggtca agtttcggaa taaacatcgg gaaggcaggg
      361 gatacaatcg gaatatttga ccttgtatcc ttgaaagccc tggacggtgt acttccagat
      421 ggagtatcgg atgcttccag aaccagcgca gatgacaaat ggttgccttt gtatctactt
      481 ggcttataca gagtgggcag aacacaaatg cctgaataca gaaaaaggct catggatggg
      541 ctgacaaatc aatgcaaaat gatcaatgaa cagtttgaac ctcttgtgcc agaaggtcgt
      601 gacattttg atgtgtgggg aaatgacagt aattacacaa aaattgtcgc tgcagtggac
      661 atgttcttcc acatgttcaa aaaacatgaa tgtgcctcgt tcagatacgg aactattgtt
      721 tccagattca aagattgtgc tgcattggca acatttggac acctctgcaa ataaccgga
      781 atgtctacag aagatgtgac gacctggatc ttgaaccgag aagttgcaga tgagatggtc
      841 caaatgatgc ttccaggcca agaaattgac aaggctgatt catacatgcc ttatttgatc
      901 gactttggat tgtcttctaa gtctccatat tcttccgtca aaaaccctgc cttccacttc
      961 tgggggcaat tgacagctct tctgctcaga tccaccagag caaggaatgc ccgacagcct
     1021 gatgacattg agtatacatc tcttactaca gcaggtttgt tgtacgctta tgcagtagga
     1081 tcctctgctg acttggcaca acagttttgt gttggagata gcaaatacac tccagatgat
     1141 agtaccggag gattgacgac taatgcaccg ccacaaggca gagatgtggt cgaatggctc
     1201 ggatggtttg aagatcaaaa cagaaaaccg actcctgata tgatgcagta tgcgaaacga
     1261 gcagtcatgt cactgcaagg cctaagagag aagacaattg caagtatgc taagtcagag
     1321 tttgacaaat gacccctataa ttctcagatc acctattata tattatgcta catatgaaaa
     1381 aaactaacag atatcatgga taatctcaca aaagttcgtg agtatctcaa gtcctattct
     1441 cgtctagatc aggcggtagg agagatagat gagatcgaag cacaacgagc tgaaaagtcc
     1501 aattatgagt tgttccaaga ggacggagtg gaagagcata ctaggccctc ttattttcag
     1561 gcagcagatg attctgacac agaatctgaa ccagaaattg aagacaatca aggcttgtat
     1621 gtaccagatc cggaagctga gcaagttgaa ggctttatac aggggccttt agatgactat
     1681 gcagatgagg acgtggatgt tgtattcact tcggactgga acagcctga gcttgaatcc
     1741 gacgagcatg aaagaccttt acggttgaca ttgccagagg gtttaagtgg agagcagaaa
     1801 tcccagtggc ttttgacgat taaagcagtc gttcaaagtg ccaaacactg gaatctggca
     1861 gagtgcacat tgaagcatc gggagaaggg gtcatcataa aaaagcgcca gataactccg
     1921 gatgtatata aggtcactcc agtgatgaac acacatccgt accaatcaga agccgtatca
     1981 gatgtttggt ctctctcaaa gacatccatg actttccaac ccagaaagc aagtcttcag
     2041 cctctcacca tatccttgga tgaattgttc tcatctagag gagaattcat ctctgtcgga
     2101 ggtaacggac gaatgtctca taaagaggcc atcctgctcg gtctgaggta caaaaagttg
```

```
2161  tacaatcagg cgagagtcaa atattctctg tagactatga aaaaaagtaa cagatatcac
2221  aatctaagtg ttatcccaat ccattcatca tgagttcctt aaagaagatt ctcggtctga
2281  aggggaaagg taagaaatct aagaaattag ggatcgcacc accccttat gaagaggaca
2341  ctaacatgga gtatgctccg agcgctccaa ttgacaaatc ctattttgga gttgacgaga
2401  tggacactca tgatccgaat caattaagat atgagaaatt cttctttaca gtgaaaatga
2461  cggttagatc taatcgtccg ttcagaacat actcagatgt ggcagccgct gtatcccatt
2521  gggatcacat gtacatcgga atggcaggga acgtccctt ctacaagatc ttggcttttt
2581  tggttcttc taatctaaag gccactccag cggtattggc agatcaaggt caaccagagt
2641  atcatgctca ctgtgaaggc agggcttatt tgccacacag aatggggaag acccctccca
2701  tgctcaatgt accagagcac ttcagaagac cattcaatat aggtctttac aagggaacga
2761  ttgagctcac aatgaccatc tacgatgatg agtcactgga agcagctcct atgatctggg
2821  atcatttcaa ttcttccaaa ttttctgatt tcagagagaa ggccttaatg tttggcctga
2881  ttgtcgagaa aaaggcatct ggagcttggg tcctggattc tgtcagccac ttcaaatgag
2941  ctagtctagc ttccagcttc tgaacaatcc ccggtttact cagtctctcc taattccagc
3001  ctttcgaaca actaatatcc tgtcttctct atcccgatga aaaaaactaa cagagatcga
3061  tctgtttcct tgacaccatg aagtgccttt tgtacttagc tttttattc atcggggtga
3121  attgcaagtt caccatagtt tttccacaca accaaaaagg aaactggaaa aatgttcctt
3181  ccaattacca ttattgcccg tcaagctcag atttaaattg gcataatgac ttagtaggca
3241  cagccttaca agtcaaaatg cccaagagtc acaaggctat tcaagcagac ggttggatgt
3301  gtcatgcttc caaatgggtc actacttgtg atttccgctg tacggaccg aagtatataa
3361  cacattccat ccgatccttc actccatctg tagaacaatg caaggaaagc attgaacaaa
3421  cgaaacaagg aacttggctg aatccaggct ccctcctca agttgtgga tatgcaactg
3481  tgacggatgc tgaagcagcg attgtccagg tgactcctca ccatgtgctt gttgatgaat
3541  acacaggaga atgggttgat tcacagttca tcaacggaaa atgcagcaat gacatatgcc
3601  ccactgtcca taactccaca acctggcatt ccgactataa ggtcaaaggg ctatgtgatt
3661  ctaacctcat ttccatggac atcaccttct ctcagagga cggagagcta tcatccctag
3721  gaaagaaggg cacagggttc agaagtaact actttgctta tgaaactgga gacaaggcct
3781  gcaaaatgca gtactgcaag cattggggag tcagactccc atcaggtgtc tggttcgaga
3841  tggctgataa ggmtctcttt gctgcagcca gattccctga atgcccagaa gggtcaagta
3901  tctctgctcc atctcagacc tcagtggatg taagtctcat tcaggacgtt gagaggatct
3961  tggattattc cctctgccaa gaaacctgga gcaaaatcag agcgggtctt cccatctctc
4021  cagtggatct cagctatctt gctcctaaaa acccaggaac cggtcctgtc tttaccataa
4081  tcaatggtac cctaaaatac tttgagacca gatacatcag agtcgatatt gctgctccaa
4141  tcctctcaag aatggtcgga atgatcagtg aactaccac agaaagggta ctgtgggatg
4201  actgggctcc atatgaagac gtggaaattg gacccaatgg agttctgagg accagttcag
4261  gatataagtt tccttatat atgattggac atggtatgtt ggactccgat cttcatctta
4321  gctcaaaggc tcaggtgttt gaacatcctc acattcaaga cgctgcttcg cagcttcctg
4381  atggtgagac tttattttt ggtgatactg ggctatccaa aaatccaatc gagtttgtag
4441  aaggttggtt cagtagttgg aagagctcta ttgcctcttt tttctttacc atagggttaa
4501  tcattggact attcttggtt ctccgagttg gtatttatct ttgcattaaa ttaaagcaca
```

-continued

```
4561   ccaagaaaag acagatttat acagacatag agatgaaccg acttggaaag taactcaaat
4621   cctgcacaac agattcttca tgtttgaacc aaatcaactt gtgatatcat gctcaaagag
4681   gccttaatta tattttaatt tttaatttt atgaaaaaaa ctaacagcaa tcatggaagt
4741   ccacgatttt gagaccgacg agttcaatga tttcaatgaa gatgactatg ccacaagaga
4801   attcctgaat cccgatgagc gcatgacgta cttgaatcat gctgattaca atttgaattc
4861   tcctctaatt agtgatgata ttgacaattt gatcaggaaa ttcaattctc ttccgattcc
4921   ctcgatgtgg gatagtaaga actgggatgg agttcttgag atgttaacat catgtcaagc
4981   caatcccatc tcaacatctc agatgcataa atggatggga agttggttaa tgtctgataa
5041   tcatgatgcc agtcaagggt atagtttttt acatgaagtg acaaagagg cagaaataac
5101   atttgacgtg gtggagacct tcatccgcgg ctggggcaac aaaccaattg aatacatcaa
5161   aaaggaaaga tggactgact cattcaaaat tctcgcttat ttgtgtcaaa agttttgga
5221   cttacacaag ttgacattaa tcttaaatgc tgtctctgag gtggaattgc tcaacttggc
5281   gaggactttc aaaggcaaag tcagaagaag ttctcatgga acgaacatat gcaggattag
5341   ggttcccagc ttgggtccta cttttatttc agaaggatgg gcttacttca agaaacttga
5401   tattctaatg gaccgaaact ttctgttaat ggtcaaagat gtgattatag ggaggatgca
5461   aacggtgcta tccatggtat gtagaataga caacctgttc tcagagcaag acatcttctc
5521   ccttctaaat atctacagaa ttggagataa aattgtggag aggcagggaa attttctta
5581   tgacttgatt aaaatggtgg aaccgatatg caacttgaag ctgatgaaat tagcaagaga
5641   atcaaggcct ttagtcccac aattccctca ttttgaaaat catatcaaga cttctgttga
5701   tgaagggca aaaattgacc gaggtataag attcctccat gatcagataa tgagtgtgaa
5761   aacagtggat ctcacactgg tgatttatgg atcgttcaga cattggggtc atccttttat
5821   agattattac actggactag aaaaattaca ttcccaagta accatgaaga aagatattga
5881   tgtgtcatat gcaaaagcac ttgcaagtga tttagctcgg attgttctat ttcaacagtt
5941   caatgatcat aaaaagtggt tcgtgaatgg agacttgctc cctcatgatc atccctttaa
6001   aagtcatgtt aaagaaaata catggcctac agctgctcaa gttcaagatt ttggagataa
6061   atggcatgaa cttccgctga ttaaatgttt tgaaataccc gacttactag acccatcgat
6121   aatatactct gacaaaagtc attcaatgaa taggtcagag gtgttgaaac atgtccgaat
6181   gaatccgaac actcctatcc ctagtaaaaa ggtgttgcag actatgttgg acacaaaggc
6241   taccaattgg aaagaatttc ttaaagagat tgatgagaag ggcttagatg atgatgatct
6301   aattattggt cttaaaggaa aggagaggga actgaagttg gcaggtagat ttttctccct
6361   aatgtcttgg aaattgcgag aatactttgt aattaccgaa tatttgataa agactcattt
6421   cgtccctatg tttaaaggcc tgacaatggc ggacgatcta actgcagtca ttaaaaagat
6481   gttagattcc tcatccggcc aaggattgaa gtcatatgag gcaatttgca tagccaatca
6541   cattgattac gaaaaatgga ataaccacca aggaagtta tcaaacggcc cagtgttccg
6601   agttatgggc cagttcttag ttatccatc cttaatcgag agaactcatg aattttttga
6661   gaaaagtctt atatactaca atggaagacc agacttgatg cgtgttcaca caacacact
6721   gatcaattca acctcccaac gagtttgttg gcaaggacaa gagggtggac tggaaggtct
6781   acggcaaaaa ggatggagta tcctcaatct actggttatt caaagagagg ctaaaatcag
6841   aaacactgct gtcaaagtct tggcacaagg tgataatcaa gttatttgca cacagtataa
6901   aacgaagaaa tcgagaaacg ttgtagaatt acagggtgct ctcaatcaaa tggtttctaa
6961   taatgagaaa attatgactg caatcaaaat agggacaggg aagttaggac ttttgataaa
```

```
7021  tgacgatgag actatgcaat ctgcagatta cttgaattat ggaaaaatac cgattttccg
7081  tggagtgatt agagggttag agaccaagag atggtcacga gtgacttgtg tcaccaatga
7141  ccaaataccc acttgtgcta atataatgag ctcagtttcc acaaatgctc tcaccgtagc
7201  tcattttgct gagaacccaa tcaatgccat gatacagtac aattattttg ggacatttgc
7261  tagactcttg ttgatgatgc atgatcctgc tcttcgtcaa tcattgtatg aagttcaaga
7321  taagataccg ggcttgcaca gttctacttt caaatacgcc atgttgtatt tggacccttc
7381  cattggagga gtgtcgggca tgtctttgtc caggttttg attagagcct tcccagatcc
7441  cgtaacagaa agtctctcat tctggagatt catccatgta catgctcgaa gtgagcatct
7501  gaaggagatg agtgcagtat ttggaaaccc cgagatagcc aagtttcgaa taactcacat
7561  agacaagcta gtagaagatc caacctctct gaacatcgct atgggaatga gtccagcgaa
7621  cttgttaaag actgaggtta aaaaatgctt aatcgaatca agacaaacca tcaggaacca
7681  ggtgattaag gatgcaacca tatatttgta tcatgaagag atcggctca gaagtttctt
7741  atggtcaata aatcctctgt tccctagatt tttaagtgaa ttcaaatcag gcactttttt
7801  gggagtcgca gacgggctca tcagtctatt tcaaaattct cgtactattc ggaactcctt
7861  taagaaaaag tatcataggg aattggatga tttgattgtg aggagtgagg tatcctcttt
7921  gacacattta gggaaacttc atttgagaag gggatcatgt aaaatgtgga catgttcagc
7981  tactcatgct gacacattaa gatacaaatc ctggggccgt acagttattg ggacaactgt
8041  accccatcca ttagaaatgt tgggtccaca acatcgaaaa gagactcctt gtgcaccatg
8101  taacacatca gggttcaatt atgtttctgt gcattgtcca gacgggatcc atgacgtctt
8161  tagttcacgg ggaccattgc ctgcttatct agggtctaaa acatctgaat ctacatctat
8221  tttgcagcct tgggaaaggg aaagcaaagt cccactgatt aaaagagcta cacgtcttag
8281  agatgctatc tcttggtttg ttgaacccga ctctaaacta gcaatgacta tactttctaa
8341  catccactct ttaacaggcg aagaatggac caaaaggcag catgggttca aaagaacagg
8401  gtctgcccct cataggttt cgacatctcg gatgagccat ggtgggttcg catctcagag
8461  cactgcagca ttgaccaggt tgatggcaac tacagacacc atgagggatc tgggagatca
8521  gaatttcgac ttttttattcc aagcaacgtt gctctatgct caaattacca ccactgttgc
8581  aagagacgga tggatcacca gttgtacaga tcattatcat attgcctgta agtcctgttt
8641  gagacccata aagagagatca ccctggactc aagtatggac tacacgcccc cagatgtatc
8701  ccatgtgctg aagacatgga ggaatgggga aggttcgtgg ggacaagaga taaaacagat
8761  ctatcccttta gaagggaatt ggaagaattt agcacctgct gagcaatcct atcaagtcgg
8821  cagatgtata ggttttctat atggagactt ggcgtataga aaatctactc atgccgagga
8881  cagttctcta tttcctctat ctatacaagg tcgtattaga ggtcgaggtt tcttaaaagg
8941  gttgctagac ggattaatga gagcaagttg ctgccaagta atacaccgga gaagtctggc
9001  tcatttgaag aggccggcca acgcagtgta cggaggtttg atttacttga ttgataaatt
9061  gagtgtatca cctccattcc tttctcttac tagatcagga cctattagag acgaattaga
9121  aacgattccc cacaagatcc caacctccta tccgacaagc aaccgtgata tgggggtgat
9181  tgtcagaaat tacttcaaat accaatgccg tctaattgaa agggaaaat acagatcaca
9241  ttattcacaa ttatggttat tctcagatgt cttatccata gacttcattg gaccattctc
9301  tatttccacc accctcttgc aaatcctata caagccattt ttatctggga agataagaa
9361  tgagttgaga gagctggcaa atctttcttc attgctaaga tcaggagagg ggtgggaaga
```

```
-continued
 9421   catacatgtg aaattcttca ccaaggacat attattgtgt ccagaggaaa tcagacatgc 9481   ttgcaagttc gggattgcta aggataataa taaagacatg agctatcccc cttggggaag 9541   ggaatccaga gggacaatta caacaatccc tgtttattat acgaccaccc cttacccaaa 9601   gatgctagag atgcctccaa gaatccaaaa tcccctgctg tccggaatca ggtttgggcca 9661   attaccaact ggcgctcatt ataaaattcg gagtatatta catggaatgg gaatccatta 9721   cagggacttc ttgagttgtg gagacggctc cggagggatg actgctgcat tactacgaga 9781   aaatgtgcat agcagaggaa tattcaatag tctgttagaa ttatcagggt cagtcatgcg 9841   aggcgcctct cctgagcccc ccagtgccct agaaacttta ggaggagata aatcgagatg 9901   tgtaaatggt gaaacatgtt gggaatatcc atctgactta tgtgacccaa ggacttggga 9961   ctatttcctc cgactcaaag caggcttggg gcttcaaatt gatttaattg taatggatat 10021   ggaagttcgg gattcttcta ctagcctgaa aattgagacg aatgttagaa attatgtgca 10081   ccggattttg gatgagcaag gagtttttaat ctacaagact tatggaacat atatttgtga 10141   gagcgaaaag aatgcagtaa caatccttgg tcccatgttc aagacggtcg acttagttca 10201   aacagaattt agtagttctc aaacgtctga agtatatatg gtatgtaaag gtttgaagaa 10261   attaatcgat gaacccaatc ccgattggtc ttccatcaat gaatcctgga aaaacctgta 10321   cgcattccag tcatcagaac aggaatttgc cagagcaaag aaggttagta catactttac 10381   cttgacaggt attccctccc aattcattcc tgatccttt gtaaacattg agactatgct 10441   acaaatattc ggagtaccca cgggtgtgtc tcatgcggct gccttaaaat catctgatag 10501   acctgcagat ttattgacca ttagcctttt ttatatgcg attatatcgt attataacat 10561   caatcatatc agagtaggac cgatacctcc gaaccccca tcagatggaa ttgcacaaaa 10621   tgtggggatc gctataactg gtataagctt ttggctgagt ttgatggaga aagacattcc 10681   actatatcaa cagtgtttag cagttatcca gcaatcattc ccgattaggt gggaggctgt 10741   ttcagtaaaa ggaggataca agcagaagtg gagtactaga ggtgatgggc tcccaaaaga 10801   tacccgaatt tcagactcct tggcccaat cgggaactgg atcagatctc tggaattggt 10861   ccgaaaccaa gttcgtctaa atccattcaa tgagatcttg ttcaatcagc tatgtcgtac 10921   agtggataat catttgaaat ggtcaaattt gcgaagaaac acaggaatga ttgaatggat 10981   caatagacga atttcaaaag aagaccggtc tatactgatg ttgaagagtg acctacacga 11041   ggaaaactct tggagagatt aaaaaatcat gaggagactc caaactttaa gtatgaaaaa 11101   aactttgatc cttaagaccc tcttgtggtt tttattttt atctggtttt gtggtcttcg 11161   t// (SEQ ID NO: 8)
```

Example 2: VSV Genome and Cloning Fragments

Figure 2A:
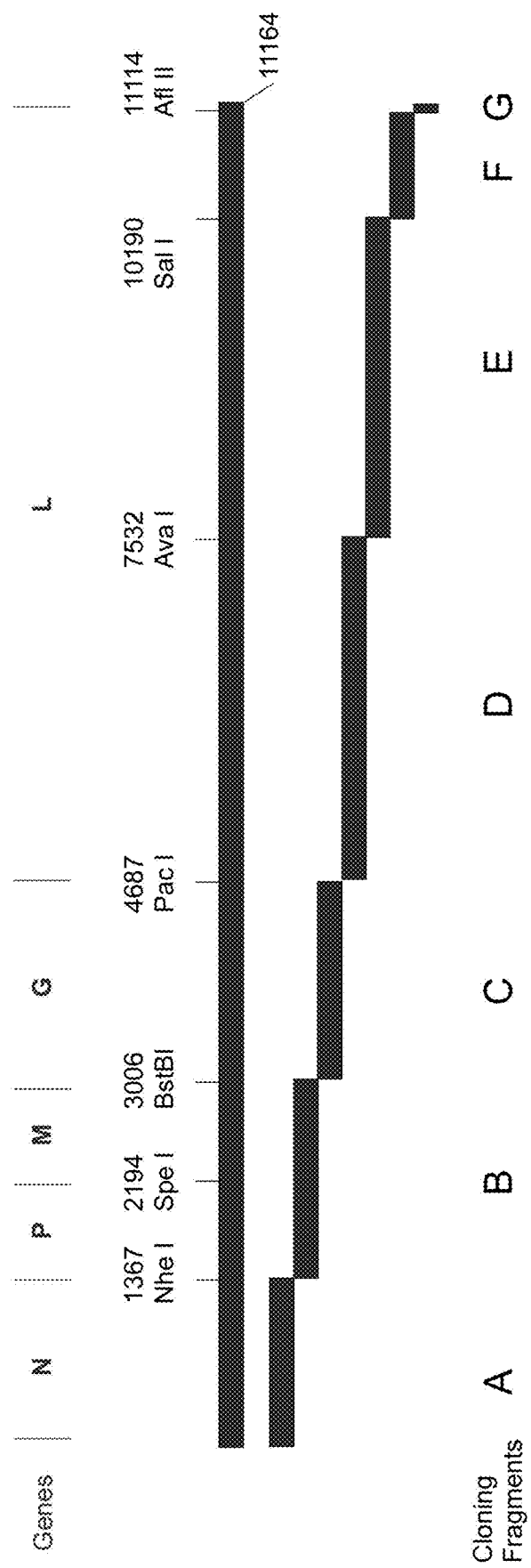
FIG. 2A depicts a schematic VSV genome and cloning fragments where fragments A and G are combined to produce fragment VSV-AG. The AG fragment may be cloned first. There are BsmBI sites added to the termini of AG fragment, which may be used to add ribozyme sequences to the termini without addition of nucleotides introduced by the restriction enzyme cleavage site. There may be a polylinker added between the combined A-G fragments (NheI-BstBI-PacI-AvaI-SalI-AflII). After cloning the VSV-AG fragment into the Dual Ribozyme vector, B through F may be inserted in subsequent cloning steps.
Figure 4:
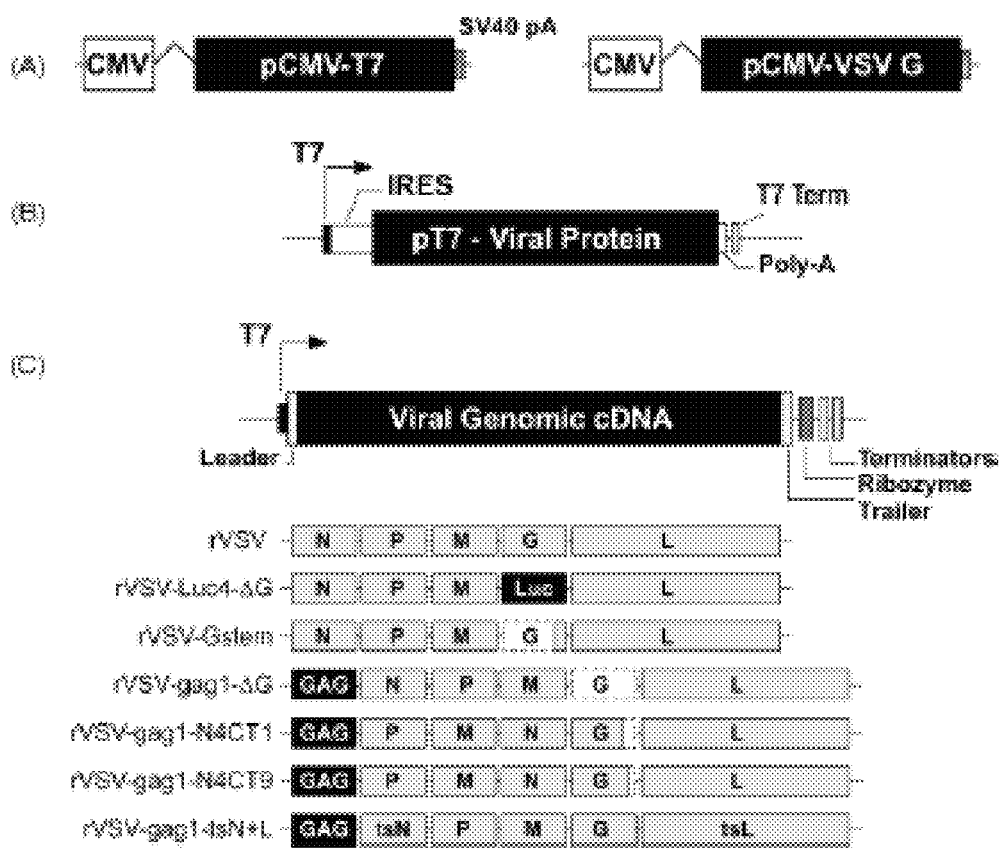
FIG. 4 depicts plasmid vectors used for recombinant virus rescue. (A) Diagram illustrating the two RNA polymerse II-dependent vectors used, both controlled by the CMV promoter and enhancer. Plasmid pCMV-T7 encodes the bacteriophage T7 RNAP and pCMV-G encodes the VSV membrane glycoprotein. (B) The general structure of plasmids encoding viral trans-acting proteins. These expression plasmids (Moss et al., 1990; Radecke et al., 1995) encode the polypeptides required for RNP assembly, transcription, and replication including N protein (or NP), P protein, and L protein. In most rescue experiments, similar vectors were included that encoded the matrix protein and viral glycoproteins. These plasmids contain an IRES element preceding the coding sequences to promote translation, and a template-encoded poly-A sequence at the 3_end to mimic an authentic mRNA poly-A tail. (C) A generic map illustrating the structure of full-length viral genomic cDNA clones is shown at the top. The T7 RNAP promoter at the 5_end directs synthesis of a positive-sense genomic transcript before transcription is terminated by two phage T7 terminator sequences. The hepatitis delta virus ribozyme cleaves the primary transcript to generate the correct 3_end. Structures of specific rVSV clones are illustrated below the generic map. A propagation-defective vector lacking the G gene (Roberts et al., 1999) was constructed by replacing the G protein coding sequence with the luciferase ORF to produce rVSV-G-Luc4. rVSV-Gstem encodes a truncated G protein that lacks most of the extracellular domain (Robison and Whitt, 2000) and is propagation-defective as well. Three vectors encoded HIV gag from the first genomic position. Vector rVSVgag1-G lacks a G protein coding sequence. rVSVgag1-N4CT1 and rVSVgag1-N4CT9 both were constructed with the N gene translocated (Ball et al., 1999; Wertz et al., 1998) to the fourth genomic position and modified G protein coding sequences. The G proteins encoded by these viruses have truncated cytoplasmic tails of one (CT1) or nine (CT9) amino acids (Roberts et al., 1999). Vector rVSVgag1-tsN+L contained genes encoding temperature-sensitive (ts) N and L proteins derived from biologically-derived VSV mutants tsG41 and tsG11 (Pringle, 1970).
Figure 6:
FIG. 6 depicts a method for virus rescue by electroporation. The flow diagram in Part A outlines the electroporation procedure. For some rVSV strains that replicate rapidly once rescue has been achieved, the coculture step was omitted. Part B illustrates the supplemental process used to generate Vero cells expressing VSV G protein to complement propagation-defective vectors that do not encode a functional attachment protein.

FIG. 2A depicts a schematic of a VSV genome and cloning fragments.

In the sequences provided in FIGS. 2B-2G, terminal fragments A and G are combined to produce fragment VSV-AG.

- The DNA fragments are designed for cloning into pSP72 or other similar cloning vectors. Before adding VSV cDNA sequences, the cloning plasmid is modified by insertion of the hammerhead and hepatitis delta virus ribozyme sequences. A BsmBI restriction enzyme cleavage site is placed between the ribozyme sequences (5'-hammerhead ribozyme-BsmBI-hepatitis delta virus ribozyme-3') for the purpose of inserting the VSV-AG fragment.
- The AG fragment was designed with BsmBI sites at the 5' and 3' termini (lower case nucleotides) for insertion between the ribozyme sequences introduced in the step above. Because BsmBI cleaves distal to its recognition sequence (see bullet below), this enzyme may be used to join the AG fragment directly to the ribozymes while also eliminating the non-VSV nucleotides added to create the enzyme cleavage signal. (Ball L A, Pringle C R, Flanagan B, Perepelitsa V P, Wertz G W. Phenotypic consequences of rearranging the P, M, and G genes of vesicular stomatitis virus. J Virol. 1999 June; 73 (6): 4705-12, the disclosure of which is incorporated by reference).
- Like other restriction endonucleases of this type (BspMI, EarI, PleI, SfaNI and others), BsmBI cleaves distal to its recognition sequence:

5'-CGTCTC/N-3'  (SEQ ID NO: 18)

3'-GCAGAGNNNNN/N-5'

N is any nucleotide and/indicates cleavage site.

The VSV-ΔG fragment also is designed to facilitate subsequent cloning. Between the fused A and G fragments there is a polylinker sequence (noted in red nucleotides) that contains restriction endonuclease cleavage sites needed for sequential cloning of Fragments B-F to assemble a full-length clone. The polylinker contains 5'-NheI-BstBI-PacI-AvaI-SalI-AflII-3' restriction endonuclease cleavage sites. Polylinker nucleotides are replaced by VSV genomic sequence as the full-length clone is assembled.

Example 3: Virus Rescue Support Plasmid Insert Optimization

Strategy for optimizing gene inserts encoding VSV N, P, M, G, and L for construction of plasmid DNAs encoding trans-acting proteins needed to initiate virus rescue. Gene inserts were optimized using steps in Example 4 then synthesized by a contract lab and subsequently cloned into a plasmid under the control of the hCMV promoter and enhancer.

Example 4: Coding Sequence Optimization and Gene Design

Step 1. Replace VSV sequence with codons used by highly expressed mammalian genes. Use the Codon-Juggle program found in the GeneDesign Webtool (Richardson et al. 2010. Nucleic Acids Res 38:2603-2606 and Richardson et al. 2006. Genome Res 16:550-556).

Step 2. Eliminate potential RNA processing signals in the coding sequence that might direct unwanted RNA splicing or cleavage/polyadenylation reaction.
  a) Identify potential splice site signals and remove by introducing synonymous codons. Splice site predictions were made with the webtool at the Berkeley *Drosophila* Genome Project website (Reese et al. 1997. J Comput Biol 4:311-323).
  b) Scan the insert for consensus cleavage/polyadenylation signals (AAUAAA) (Zhao et al. 1999. MMBR 63:405-445). Disrupt by introducing synonymous codons.

Step 3
  a) Add a preferred translational start sequence (the Kozak sequence) (Kochetov et al. 1998. FEBS letters 440:351-355, Kozak. 1999. Gene 234:187-208, Kozak. 1991. J Biol Chem 266:19867-19870 and Zhang. 1998. Human molecular genetics 7:919-932).
  b) Add a preferred translational stop codon at the 3' end (Kochetov et al. 1998. FEBS letters 440:351-355, Sun et al. 2005. J Mol Evol 61:437-444 and Zhang. 1998. Human molecular genetics 7:919-932)

Step 4. Scan the sequence for homopolymeric stretches of 5 nucleotides or more. Interrupt these sequences by introducing synonymous codons.

Step 5. Scan the sequence for restriction endonuclease cleavage sites and eliminate any unwanted recognitions signals.

Step 6. Confirm that the modified sequence translates into the expected amino acid sequence.

The invention is further described by the following numbered paragraphs:

1. A vesicular stomatitis virus (VSV) genomic clone comprising:
   (a) a VSV genome encoding and expressing a nucleocapsid, phosphoprotein, matrix, glycoprotein and large protein, wherein the VSV genome comprises nucleotide substitutions and amino acid coding changes to improve replicative fitness and genetic stability,
   (b) a cloning vector,
   (c) an extended T7 promoter,
   (d) a hammerhead ribozyme,
   (e) a hepatitis delta virus ribozyme and T7 terminator
   (f) unique restriction endonuclease cleavage sites in a VSV genomic sequence
   (g) a leader and a trailer that are cis-acting sequences controlling mRNA synthesis and replication 2. The VSV genomic clone of paragraph 1, wherein the cloning vector is pSP72 (Genbank X65332.2)

3. The VSV genomic clone of paragraph 1 or 2, wherein the extended T7 promoter is PT7-g10.

4. The VSV genomic clone of any one of paragraphs 1 to 3, wherein the unique restriction endonuclease cleavage sites are 1367 NheI, 2194 SpeI, 2194 BstBI, 4687 PacI, 7532 AvaI, 10190 SalI and 11164 AflII.

5. The VSV genomic clone of any one of paragraphs 1 to 4, wherein the VSV genomic clone is depicted in FIG. 1.

6. The VSV genomic clone of any one of paragraphs 1 to 5, wherein the nucleotide position is according to GenBank Accession Number EF197793 and wherein the nucleotide substitutions are selected from the group consisting of 1371 CA>GC (NheI)

After 2195 insert TAG (SpeI) (all genome numbers below adjusted to include +3 bp)

3036 G>T improves match to consensus transcription stop signal

3853 X>A (was an ambiguity in Genbank file)

4691 T>A to generate PacI

7546 C>A silent change in L coding sequence eliminates a BstBI site

1960 TAC>TCC to change Y>S

3247 GTA>ATA to change V>I

3729 AAG>GAG to change K>E

4191 GTA>GAA to change V>E

4386 GGT>GAT to change G>D

4491 ACC>ATC to change T>I

5339 ATT>CTT to change I>L

5834 ACT>GCT to change T>A and

10959 AGA>AAA to change R>K.

7. The VSV genomic clone of any one of paragraphs 1 to 6, wherein the nucleotide position is according to GenBank Accession Number EF197793 and wherein the nucleotide substitutions are selected from the group consisting of:

| | Nucleotide position in EF197793 | Nucleotide position in rEF197793 | Nucleotide Change | Purpose |
|---|---|---|---|---|
| 1 | Substitution 1371-2 | Substitution 1371-2 | CA > GC | Creates a unique NheI cleavage site between N and P gens |
| 2 | Substitution 1960-2 | Substitution 1960-2 | TAC > TCC | Y > S substitution in P protein amino acid sequence to agree with consensus. |
| 3 | Insert after 2195 | 3 base insert after 2195 | Insert TAG | Creates a unique SpeI site between P and M genes |
| 4 | Substitution 3039 | Substitution 3042 | G > T | Improves agreement with consensus. Also improves agreement with consensus transcription stop signal |
| 5 | Substitution 3234-6 | Substitution 3237-9 | GTA > ATA | V > I substitution in P protein amino acid sequence to agree with consensus. |
| 6 | Substitution 3729-31 | Substitution 3732-34 | AAG > GAG | K > E substitution in G protein amino acid sequence to agree with consensus. |
| 7 | Substitution 3856 | Substitution 3859 | N > A | Replace unknown base in Genbank file with consensus |
| 8 | Substitution 4191-93 | Substitution 4194-6 | GTA > GAA | V > E substitution in G protein amino acid sequence to agree with consensus. |
| 9 | Substitution 4386-88 | Substitution 4389-92 | GGT > GAT | G > D substitution in G protein amino acid sequence to agree with consensus. |
| 10 | Substitution 4491-93 | Substitution 4494-96 | ACC > ATC | T > I substitution in G protein amino acid sequence to agree with consensus. |
| 11 | Substitution 4694 | Substitution 4697 | T > A | Creates unique PacI cleavage site between G and L genes |
| 12 | Substitution 5339-41 | Substitution 5342-44 | ATT > CTT | I > L substitution in L protein amino acid sequence to agree with consensus. |
| 13 | Substitution 5834-6 | Substitution 5837-40 | ACT >GCT | T > A substitution in L protein amino acid sequence to agree with consensus. |
| 14 | Substitution 10959-61 | Substitution 10962-64 | AGA > AAA | R > K substitution in L protein amino acid sequence to agree with consensus. |
| 15 | Substitution 7546 | Substitution 7549 | C > A | Eliminates a BstBI site in the L gene sequence making the BstBI site between the M and G genes unique. This substitution was silent for amino acid coding. |

8. The VSV genomic clone of any one of paragraphs 1 to 7, wherein the nucleotide sequences of the VSV genome encoding and expressing a nucleocapsid, phosphoprotein, matrix, glycoprotein and large protein are selected from the group consisting of FIGS. 2B-2G.
9. The VSV genomic clone of any one of paragraphs 1 to 7, wherein the nucleotide sequences of the VSV genome encoding and expressing a nucleocapsid, phosphoprotein, matrix, glycoprotein and large protein are selected from the group consisting of FIGS. 3A-3G,
10. A method for rescuing VSV comprising combining a T7 RNA polymerase promoter and a hammerhead ribozyme sequence to increase the efficiency of synthesis and processing of full-length VSV genomic RNA in transfected cells.
11. The method of paragraph 10, wherein the T7 RNA polymerase promoter is a minimal functional sequence designed to initiate transcription very close to or precisely at the 5' terminus of the genomic clone.
12. The method of paragraph 11, wherein the T7 promoter is a T7 promoter sequence that enhances formation of stable initiation and elongation complexes and a hammerhead ribozyme sequence at the 5' terminus that catalyzes removal of extra nucleotides restoring the authentic 5' terminus of the genomic transcript.
13. The method of any one of paragraphs 10 to 12, wherein the plasmids encoding VSV nucleocapsid, phosphoprotein, matrix, glycoprotein and large protein are optimized to improve expression of the trans-acting proteins to initiate virus rescue.
14. The method of paragraph 13, where the optimization is codon optimization.
15. The method of paragraph 14, wherein the codon optimization comprises replacing a VSV nucleotide sequence with codons used by highly expressed mammalian genes.
16. The method of paragraph 14 or 15, wherein the codon optimization comprises eliminating potential RNA processing signals in the coding sequence that might direct unwanted RNA splicing or cleavage/polyadenylation reaction, wherein the eliminating comprises:
    (a) identifying potential splice site signals and remove by introducing synonymous codons and/or
    (b) scanning an insert for consensus cleavage/polyadenylation signals (AAUAAA) and introducing synonymous codons to disrupt the consensus cleavage/polyadenylation signals.
17. The method of any one of paragraphs 14 to 16, wherein the codon optimization comprises
    (a) adding a preferred translational start sequence (the Kozak sequence) and/or
    (b) adding a preferred translational stop codon.
18. The method of any one of paragraphs 14 to 17, wherein the codon optimization comprises scanning a sequence for homopolymeric stretches of 5 nucleotides or more and interrupting the sequences by introducing synonymous codons.

19. The method of any one of paragraphs 14 to 18, wherein the codon optimization comprises scanning a sequence for restriction endonuclease cleavage sites and eliminate any unwanted recognitions signals.

20. The method of any one of paragraphs 14 to 19, wherein the codon optimization comprises confirming that a modified sequence translates into an expected amino acid sequence.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for rescuing Vesicular Stomatitis Virus (VSV) comprising combining in a single polynucleotide:
   (a) a mammalian cytomegalovirus (CMV) promoter;
   (b) a hammerhead ribozyme sequence;
   (c) a VSV genome sequence comprising restriction endonuclease cleavage sites for genetic modification and leader and trailer sequences that control mRNA synthesis and replication;
      wherein the VSV genome sequence comprises one or more substitutions at nucleotide positions 1371, 2195, 3039, 7546, and 10959 when aligned with SEQ ID NO: 8; and
   (d) a T7 promoter;
   wherein the CMV promoter, T7 promoter, and the hammerhead ribozyme sequence are operably linked to the 5' end of the VSV genome sequence in that order to increase the efficiency of synthesis and processing of full-length VSV genomic RNA in transfected or electroporated cells,
   wherein the hammerhead ribozyme sequence catalyzes removal of extra nucleotides to restore an authentic 5' terminus of the genomic transcript, and
   wherein the VSV genome sequence further comprises, at its 3' end, a hepatitis delta virus ribozyme and a T7 terminator.

2. The method of claim 1, wherein a plasmid comprising VSV genomic cDNA, a plasmid encoding bacteriophage T7 RNA polymerase, and/or plasmids expressing viral trans-acting polypeptides are transfected or electroporated into Vero cells and the VSV virus is rescued therefrom.

3. The method of claim 2 further comprising the steps of:
   (i) preparing the plasmid encoding bacteriophage T7 RNA polymerase by inserting the T7 RNA polymerase (RNAP) gene into a vector 3' of the CMV promoter,
   (ii) preparing the plasmids encoding VSV viral trans-acting polypeptides by inserting the genes encoding the VSV viral trans-acting polypeptides into a vector 3' of the CMV promoter, wherein the VSV viral trans-acting polypeptides comprise VSV nucleocapsid (N), phosphoprotein (P), matrix (M), glycoprotein (G), and large (L) protein derived from the Indiana serotype genomic DNA clone, and
   (iii) preparing the plasmid encoding a modified VSV genomic clone by inserting the VSV genomic clone into a vector comprising the CMV promoter, an extended T7 promoter (PT7-g10), a hammerhead ribozyme, a hepatitis delta virus ribozyme, a T7 RNA polymerase terminator, and unique restriction endonuclease cleavage sites.

4. The method of claim 3, wherein the plasmids encoding the T7 RNAP, VSV viral trans-acting polypeptides, and VSV genomic clone further comprises a Kozak consensus sequence is included 5' of the initiator ATG of, to provide optimal sequence context for translation.

5. The method of claim 3, wherein the plasmids encoding the T7 RNAP, VSV viral trans-acting polypeptides, and VSV genomic clone further comprises an internal ribosome entry site (IRES).

6. The method of claim 3, wherein the vector comprises a pCI-Neo expression vector.

7. The method of claim 3 further comprising transfecting Vero cells with the plasmids encoding the T7 RNAP, VSV viral trans-acting polypeptides, and VSV genomic clone, the method comprising:
   (i) feeding a Vero cell monolayer cultured in 6-well plates and incubating for 1-3 hours at 32° C. with 3% CO2,
   (ii) preparing calcium-phosphate DNA precipitates of the plasmid encoding the T7 RNA polymerase, the plasmids encoding the VSV viral trans-acting polypeptides, and the plasmid encoding the VSV genomic clone and distributing onto cells,
   (iii) incubating for 3 hours at 32° C. with 3% CO2,
   (iv) heat shocking cells for 3 hours at 43° C. with 3% CO2,
   (v) returning cells to 32° C. with 3% CO2 incubator and incubating overnight,
   (vi) washing monolayers, feeding cells with fresh medium, and incubating for 2-3 days at 32-37° C. with 5% CO2,
   (vii) transferring cells onto a fresh cell monolayer to initiate coculture, and
   (viii) replacing medium and incubating every 3-5 days until viral cytopathic effect (CPE) is evident.

8. The method of claim 3 further comprising electroporating Vero cells with the plasmids encoding the T7 RNAP, VSV viral trans-acting polypeptides, and VSV genomic clone, the method comprising:
   (i) harvesting Vero cells from a T175 flask and electroporating with the plasmids encoding VSV genomic clone, the T7 RNA polymerase, and viral trans-acting polypeptides,
   (ii) washing electroporated cells, culturing cells in T175 flask, and incubating at 37° C. for 4 hours,
   (iii) heat shocking cells for 2 hours at 43° C.,
   (iv) incubate cells at 37° C. overnight, and
   (vi) monitor cells for protein expression and CPE 48-72 hours post electroporation.

9. The method of claim 2, wherein the plasmids encoding the viral trans-acting polypeptides encode VSV N, P, M, G, and L and are optimized to improve expression of the trans-acting polypeptides to initiate virus rescue.

10. The method of claim 9, wherein the optimization is codon optimization.

11. The method of claim 10, wherein the codon optimization comprises replacing a VSV nucleotide sequence with codons used by highly expressed mammalian genes.

12. The method of claim 10, wherein the codon optimization comprises eliminating potential RNA processing signals in the coding sequence that might direct unwanted RNA splicing or cleavage/polyadenylation reaction, wherein the eliminating comprises:
   (a) identifying potential splice site signals and remove by introducing synonymous codons and/or
   (b) scanning an insert for consensus cleavage/polyadenylation signals (AAUAAA) and introducing synonymous codons to disrupt to consensus cleavage/polyadenylation signals.

13. The method of claim 10, wherein the codon optimization comprises
   (a) adding a preferred translational start sequence (the Kozak sequence) and/or
   (b) adding a preferred translational stop codon.

14. The method of claim 10, wherein the codon optimization comprises scanning a sequence for homopolymeric stretches of 5 nucleotides or more and interrupting the sequences by introducing synonymous codons.

15. The method of claim 10, wherein the codon optimization comprises scanning a sequence for restriction endonuclease cleavage sites and eliminate any unwanted recognition signals.

16. The method of claim 10, wherein the codon optimization comprises confirming that a modified sequence translates into an expected amino acid sequence.

17. The method of claim 1, wherein the substitutions comprise one or more substitutions selected from:
   (i) 1371 CA>GC,
   (ii) 2195 insert TAG,
   (iii) 3039 G>T,
   (iv) 7546 C>A, and
   (v) 10959 AGA>AAA.

18. The method of claim 1, wherein the plasmids expressing VSV trans-acting polypeptides are optimized by:
   (a) replacing VSV sequences with codons used by highly expressed mammalian genes;
   (b) eliminating potential RNA processing signals by:
      (i) removing splice site signals through introduction of synonymous codons, and
      (ii) disrupting consensus cleavage/polyadenylation signals (AAUAAA) through introduction of synonymous codons;
   (c) adding a preferred translational start sequence (Kozak sequence) and a preferred translational stop codon;
   (d) interrupting homopolymeric stretches of 5 or more nucleotides by introducing synonymous codons; and
   (e) eliminating unwanted restriction endonuclease recognition signals; wherein the optimization improves expression of the trans-acting polypeptides and increases virus rescue efficiency.

* * * * *

SEQUENCE LISTING

```
Sequence total quantity: 18
SEQ ID NO: 1            moltype = AA   length = 286
FEATURE                 Location/Qualifiers
REGION                  1..286
                        note = Description of Artificial Sequence: Synthetic
                        polypeptide
source                  1..286
                        mol_type = protein
                        organism = synthetic construct
SEQUENCE: 1
MSIQHFRVAL IPFFAAFCLP VFAHPETLVK VKDAEDQLGA RVGYIELDLN SGKILESFRP   60
EERFPMMSTF KVLLCGAVLS RIDAGQEQLG RRIHYSQNDL VEYSPVTEKH LTDGMTVREL  120
CSAAITMSDN TAANLLLTTI GGPKELTAFL HNMGDHVTRL DRWEPELNEA IPNDERDTTM  180
PVAMATTLRK LLTGELLTLA SRQQLIDWME ADKVAGPLLR SALPAGWFIA DKSGAGERGS  240
RGIIAALGPD GKPSRIVVIY TTGSQATMDE RNRQIAEIGA SLIKHW               286

SEQ ID NO: 2            moltype = DNA   length = 2462
FEATURE                 Location/Qualifiers
misc_feature            1..2462
                        note = Description of Artificial Sequence: Synthetic
                        polynucleotide
source                  1..2462
                        mol_type = other DNA
                        organism = synthetic construct
SEQUENCE: 2
gaactcgagc agctgaagct tgcatgcctg caggtcgact ctagaggatc cccgggtacc    60
gagctcgaat tcatcgatga tatcagatct gccggtctcc ctatagtgag tcgtattaat   120
ttcgataagc caggttaacc tgcattaatg aatcggccaa cgcgcgggga gaggcggttt   180
gcgtattggg cgctcttccg cttcctcgct cactgactcg ctgcgctcgg tcgttcggct   240
gcggcgagcg gtatcagctc actcaaaggc ggtaatacgg ttatccacag aatcagggga   300
taacgcagga aagaacatgt gagcaaaagg ccagcaaaag gccaggaacc gtaaaaaggc   360
cgcgttgctg gcgtttttcc ataggctccg ccccccctga gcatcaca aaaatcgacg     420
ctcaagtcag aggtggcgaa acccgacagg actataaaga taccaggcgt ttccccctgg   480
aagctccctc gtgcgctctc ctgttccgac cctgccgctt accggatacc tgtccgcctt   540
tctcccttcg ggaagcgtgg cgctttctca tagctcacgc tgtaggtatc tcagttcggt   600
gtaggtcgtt cgctccaagc tgggctgtgt gcacgaaccc cccgttcagc ccgaccgctg   660
cgccttatcc ggtaactatc gtcttgagtc caacccggta agacacgact tatcgccact   720
ggcagcagcc actggtaaca ggattagcag agcgaggtat gtaggcggtg ctacagagtt   780
cttgaagtgg tggcctaact acggctacac tagaagaaca gtatttggta tctgcgctct   840
gctgaagcca gttaccttcg gaaaaagagt tggtagctct tgatccggca aacaaaccac   900
cgctggtagc ggtggttttt ttgtttgcaa gcagcagatt acgcgcagaa aaaaaggatc   960
tcaagaagat cctttgatct tttctacggg gtctgacgct cagtggaacg aaaactcacg  1020
ttaagggatt ttggtcatga gattatcaaa aaggatcttc acctagatcc ttttaaatta  1080
aaaatgaagt tttaaatcaa tctaaagtat atatgagtaa acttggtctg acagttacca  1140
atgcttaatc agtgaggcac ctatctcagc gatctgtcta tttcgttcat ccatagttgc  1200
ctgactcccc gtcgtgtaga taactacgat acgggagggc ttaccatctg gccccagtgc  1260
tgcaatgata ccgcgagacc cacgctcacc ggctccagat ttatcagcaa taaaccagcc  1320
agccggaagg gccgagcgca gaagtggtcc tgcaacttta tccgcctcca tccagtctat  1380
taattgttgc cgggaagcta gagtaagtag ttcgccagtt aatagtttgc gcaacgttgt  1440
tgccattgct acaggcatcg tggtgtcacg ctcgtcgttt ggtatggctt cattcagctc  1500
cggttcccaa cgatcaaggc gagttacatg atccccccatg ttgtgcaaaa aagcggttag  1560
ctccttcggt cctccgatcg ttgtcagaag taagttggcc gcagtgttat cactcatggt  1620
tatggcagca ctgcataatt ctcttactgt catgccatcc gtaagatgct tttctgtgac  1680
tggtgagtac tcaaccaagt cattctgaga atagtgtatg cggcgaccga gttgctcttg  1740
cccggcgtca atacgggata ataccgcgcc acatagcaga actttaaaag tgctcatcat  1800
tggaaaacgt tcttcggggc gaaaactctc aaggatctta ccgctgttga tccagttc    1860
gatgtaaccc actcgtgcac ccaactgatc ttcagcatct tttactttca ccagcgtttc  1920
tgggtgagca aaaacaggaa ggcaaaatgc cgcaaaaaag ggaataaggg cgacacgaa    1980
atgttgaata ctcatactct tcctttttca atattattga agcattttatc agggttattg  2040
tctcatgagc ggatacatat ttgaatgtat ttagaaaaat aaacaaatag gggttccgcg  2100
cacatttccc cgaaaagtgc cacctgacgt ctaagaaacc attattatca tgacattaac  2160
ctataaaaat aggcgtatca cgaggccctt tcgtctcgcg cgtttcggtg atgacggtga  2220
aaacctctga cacatgcagc tcccggagac ggtcacagct tgtctgtaag cggatgccgg  2280
gagcagacaa gcccgtcagg gcgcgtcagc gggtgttggc gggtgtcggg gctggcttaa  2340
ctatgcggca tcagagcaga ttgtactgag agtgcaccat atggacatat tgtcgttaga  2400
acgcggctac aattaataca taaccttatg tatcatacac atacgattta ggtgacacta  2460
```

```
ta                                                              2462

SEQ ID NO: 3              moltype = AA   length = 422
FEATURE                   Location/Qualifiers
source                    1..422
                          mol_type = protein
                          note = Vesicular stomatitis Indiana virus
                          organism = unidentified
SEQUENCE: 3
MSVTVKRIID NTVIVPKLPA NEDPVEYPAD YFRKSKEIPL YINTTKSLSD LRGYVYQGLK    60
SGNVSIIHVN SYLYGALKDI RGKLDKDWSS FGINIGKAGD TIGIFDLVSL KALDGVLPDG   120
VSDASRTSAD DKWLPLYLLG LYRVGRTQMP EYRKRLMDGL TNQCKMINEQ FEPLVPEGRD   180
IFDVWGNDSN YTKIVAAVDM FFHMFKKHEC ASFRYGTIVS RFKDCAALAT FGHLCKITGM   240
STEDVTTWIL NREVADEMVQ MMLPGQEIDK ADSYMPYLID FGLSSKSPYS SVKNPAFHFW   300
GQLTALLLRS TRARNARQPD DIEYTSLTTA GLLYAYAVGS SADLAQQFCV GDSKYTPDDS   360
TGGLTTNAPP QGRDVVEWLG WFEDQNRKPT PDMMQYAKRA VMSLQGLREK TIGKYAKSEF   420
DK                                                                  422

SEQ ID NO: 4              moltype = AA   length = 265
FEATURE                   Location/Qualifiers
source                    1..265
                          mol_type = protein
                          note = Vesicular stomatitis Indiana virus
                          organism = unidentified
SEQUENCE: 4
MDNLTKVREY LKSYSRLDQA VGEIDEIEAQ RAEKSNYELF QEDGVEEHTR PSYFQAADDS    60
DTESEPEIED NQGLYVPDPE AEQVEGFIQG PLDDYADEDV DVVFTSDWKQ PELESDEHGK   120
TLRLTLPEGL SGEQKSQWLL TIKAVVQSAK HWNLAECTFE ASGEGVIIKK RQITPDVYKV   180
TPVMNTHPYQ SEAVSDVWSL SKTSMTFQPK KASLQPLTIS LDELFSSRGE FISVGGNGRM   240
SHKEAILLGL RYKKLYNQAR VKYSL                                         265

SEQ ID NO: 5              moltype = AA   length = 229
FEATURE                   Location/Qualifiers
source                    1..229
                          mol_type = protein
                          note = Vesicular stomatitis Indiana virus
                          organism = unidentified
SEQUENCE: 5
MSSLKKILGL KGKGKKSKKL GIAPPPYEED TNMEYAPSAP IDKSYFGVDE MDTHDPNQLR    60
YEKFFFTVKM TVRSNRPFRT YSDVAAAVSH WDHMYIGMAG KRPFYKILAF LGSSNLKATP   120
AVLADQGQPE YHAHCEGRAY LPHRMGKTPP MLNVPEHFRR PFNIGLYKGT IELTMTIYDD   180
ESLEAAPMIW DHFNSSKFSD FREKALMFGL IVEKKASGAW VLDSVSHFK              229

SEQ ID NO: 6              moltype = AA   length = 511
FEATURE                   Location/Qualifiers
source                    1..511
                          mol_type = protein
                          note = Vesicular stomatitis Indiana virus
                          organism = unidentified
VARIANT                   259
                          note = X can be any Amino Acid
SEQUENCE: 6
MKCLLYLAFL FIGVNCKFTI VFPHNQKGNW KNVPSNYHYC PSSSDLNWHN DLVGTALQVK    60
MPKSHKAIQA DGWMCHASKW VTTCDFRWYG PKYITHSIRS FTPSVEQCKE SIEQTKQGTW   120
LNPGFPPQSC GYATVTDAEA AIVQVTPHHV LVDEYTGEWV DSQFINGKCS NDICPTVHNS   180
TTWHSDYKVK GLCDSNLISM DITFFSEDGE LSSLGKKGTG FRSNYFAYET GDKACKMQYC   240
KHWGVRLPSG VWFEMADKXL FAAARFPECP EGSSISAPSQ TSVDVSLIQD VERILDYSLC   300
QETWSKIRAG LPISPVDLSY LAPKNPGTGP VFTIINGTLK YFETRYIRVD IAAPILSRMV   360
GMISGTTTER VLWDDWAPYE DVEIGPNGVL RTSSGYKFPL YMIGHGMLDS DLHLSSKAQV   420
FEHPHIQDAA SQLPDGETLF FGDTGLSKNP IEFVEGWFSS WKSSIASFFF TIGLIIGLFL   480
VLRVGIYLCI KLKHTKKRQI YTDIEMNRLG K                                  511

SEQ ID NO: 7              moltype = AA   length = 2109
FEATURE                   Location/Qualifiers
source                    1..2109
                          mol_type = protein
                          note = Vesicular stomatitis Indiana virus
                          organism = unidentified
SEQUENCE: 7
MEVHDFETDE FNDFNEDDYA TREFLNPDER MTYLNHADYN LNSPLISDDI DNLIRKFNSL    60
PIPSMWDSKN WDGVLEMLTS CQANPISTSQ MHKWMGSWLM SDNHDASQGY SFLHEVDKEA   120
EITFDVVETF IRGWGNKPIE YIKKERWTDS FKILAYLCQK FLDLHKLTLI LNAVSEVELL   180
NLARTFKGKV RRSSHGTNIC RIRVPSLGPT FISEGWAYFK KLDILMDRNF LLMVKDVIIG   240
RMQTVLSMVC RIDNLFSEQD IFSLLNIYRI GDKIVERQGN FSYDLIKMVE PICNLKLMKL   300
ARESRPLVPQ FPHFENHIKT SVDEGAKIDR GIRFLHDQIM SVKTVDLTLV IYGSFRHWGH   360
PFIDYYTGLE KLHSQVTMKK DIDVSYAKAL ASDLARIVLF QQFNDHKKWF VNGDLLPHDH   420
PFKSHVKENT WPTAAQVQDF GDKWHELPLI KCFEIPDLLD PSIIYSDKSH SMNRSEVLKH   480
VRMNPNTPIP SKKVLQTMLD TKATNWKEFL KEIDEKGLDD DDLIIGLKGK ERELKLAGRF   540
FSLMSWKLRE YFVITEYLIK THFVPMFKGL TMADDLTAVI KKMLDSSSGQ GLKSYEAICI   600
```

```
ANHIDYEKWN NHQRKLSNGP VFRVMGQFLG YPSLIERTHE FFEKSLIYYN GRPDLMRVHN   660
NTLINSTSQR VCWQGQEGGL EGLRQKGWSI LNLLVIQREA KIRNTAVKVL AQGDNQVICT   720
QYKTKKSRNV VELQGALNQM VSNNEKIMTA IKIGTGKLGL LINDDETMQS ADYLNYGKIP   780
IFRGVIRGLE TKRWSRVTCV TNDQIPTCAN IMSSVSTNAL TVAHFAENPI NAMIQYNYFG   840
TFARLLLMMH DPALRQSLYE VQDKIPGLHS STFKYAMLYL DPSIGGVSGM SLSRFLIRAF   900
PDPVTESLSF WRFIHVHARS EHLKEMSAVF GNPEIAKFRI THIDKLVEDP TSLNIAMGMS   960
PANLLKTEVK KCLIESRQTI RNQVIKDATI YLYHEEDRLR SFLWSINPLF PRFLSEFKSG  1020
TFLGVADGLI SLFQNSRTIR NSFKKKYHRE LDDLIVRSEV SSLTHLGKLH LRRGSCKMWT  1080
CSATHADTLR YKSWGRTVIG TTVPHPLEML GPQHRKETPC APCNTSGFNY VSVHCPDGIH  1140
DVFSSRGPLP AYLGSKTSES TSILQPWERE SKVPLIKRAT RLRDAISWFV EPDSKLAMTI  1200
LSNIHSLTGE EWTKRQHGFK RTGSALHRFS TSRMSHGGFA SQSTAALTRL MATTDTMRDL  1260
GDQNFDFLFQ ATLLYAQITT TVARDGWITS CTDHYHIACK SCLRPIEEIT LDSSMDYTPP  1320
DVSHVLKTWR NGEGSWGQEI KQIYPLEGNW KNLAPAEQSY QVGRCIGFLY GDLAYRKSTH  1380
AEDSSLFPLS IQGRIRGRGF LKGLLDGLMR ASCCQVIHRR SLAHLKRPAN AVYGGLIYLI  1440
DKLSVSPPFL SLTRSGPIRD ELETIPHKIP TSYPTSNRDM GVIVRNYFKY QCRLIEKGKY  1500
RSHYSQLWLF SDVLSIDFIG PFSISTTLLQ ILYKPFLSGK DKNELRELAN LSSLLRSGEG  1560
WEDIHVKFFT KDILLCPEEI RHACKFGIAK DNNKDMSYPP WGRESRGTIT TIPVYYTTTP  1620
YPKMLEMPPR IQNPLLSGIR LGQLPTGAHY KIRSILHGMG IHYRDFLSCG DGSGGMTAAL  1680
LRENVHSRGI FNSLLELSGS VMRGASPEPP SALETLGGDK SRCVNGETCW EYPSDLCDPR  1740
TWDYFLRLKA GLGLQIDLIV MDMEVRDSST SLKIETNVRN YVHRILDEQG VLIYKTYGTY  1800
ICESEKNAVT ILGPMFKTVD LVQTEFSSSQ TSEVYMVCKG LKKLIDEPNP DWSSINESWK  1860
NLYAFQSSEQ EFARAKKVST YFTLTGIPSQ FIPDPFVNIE TMLQIFGVPT GVSHAAALKS  1920
SDRPADLLTI SLFYMAIISY YNINHIRVGP IPPNPPSDGI AQNVGIAITG ISFWLSLMEK  1980
DIPLYQQCLA VIQQSFPIRW EAVSVKGGYK QKWSTRGDGL PKDTRISDSL APIGNWIRSL  2040
ELVRNQVRLN PFNEILFNQL CRTVDNHLKW SNLRRNTGMI EWINRRISKE DRSILMLKSD  2100
LHEENSWRD                                                         2109

SEQ ID NO: 8            moltype = DNA   length = 11161
FEATURE                 Location/Qualifiers
source                  1..11161
                        mol_type = other DNA
                        note = Vesicular stomatitis Indiana virus
                        organism = unidentified
SEQUENCE: 8
acgaagacaa acaaaccatt attatcatta aaaggctcag gagaaacttt aacagtaatc   60
aaaatgtctg ttacagtcaa gagaatcatt gacaacacag tcatagttcc aaaacttcct  120
gcaaatgagg atccagtgga atacccggca gattacttca gaaaatcaaa ggagattcct  180
ctttacatca atactacaaa aagtttgtca gatctaagag atatgtcta ccaaggcctc  240
aaatcagaa atgtatcaat catacatgtc aacagctact tgtatggagc attgaaggac  300
atccggggta agttggataa agattggtca agtttcggaa taaacatcgg gaaggcaggg  360
gatacaatcg gaatatttga ccttgtatcc ttgaaagccc tggacggtgt acttccagat  420
ggagtatcgg atgcttccag aaccagcgca gatgacaaat ggttgccttt gtatctactt  480
ggcttataca gagtgggcag aacacaaatg cctgaataca tggatgatggg  540
ctgacaaatc aatgcaaaat gatcaatgaa cagtttgaac ctcttgtgcc agaaggtcgt  600
gacatttttg atgtgtgggg aaatgacagt aattacacaa aaattgtcgc tgcagtggac  660
atgttcttcc acatgttcaa aaaacatgaa tgtgcctcgt tcagatacgg aactattgtt  720
tccagattca aagattgtgc tgcattggca acatttgaac acctctgcaa aataaccgga  780
atgtctacag aagatgtgac gacctggatc ttgaaccgag aagttgcaga tgagatggtc  840
caaatgatgc ttccaggcca agaaattgac aaggctgatt catacatgcc ttatttgatc  900
gactttggat tgtcttctaa gtctccatat tcttccgtca aaaaccctgc cttccacttc  960
tggggcaat tgacagctct tctgctcaga tccaccaagg caaggaatgc ccgacagcct 1020
gatgacattg agtatacatc tcttactaca gcaggtttgt tgtacgctta tgcagtagga 1080
tcctctgctg acttggcaca acagttttgt gttggagata gcaaatacac tccagatgat 1140
agtaccggag gattgacgac taatgcaccg ccacaaggca gagatgtggt cgaatggctc 1200
ggatggtttg aagatcaaaa cagaaaaccg actcctgata tgtcagtga tgcgaaacga 1260
gcagtcatgt cactgcaagg cctaagagag aagacaattg caagtatgc taagtcagag 1320
tttgacaaat gacccataa ttctcagatc acctattata tattatgcta catatgaaaa 1380
aaactaacag atatcatgga taatctcaca aaagttcgtg agtatctcaa gtcctattct 1440
cgtctagatc aggcggtagg agagatagat gagatcgaag cacaacgagc tgaaaagtcc 1500
aattatgagt tgttccaaga ggacggagtg gaagagcata ctaggccctc ttatttttcag 1560
gcagcagatg attctgacac agaatctgaa ccagaaattg aagacaatca aggcttgtat 1620
gtaccagatc cggaagctga gcaagttgaa ggctttatac aggggccttt agatgactat 1680
gcagatgagg acgtggatgt tgtattcact tcggactgga acagcctga gcttgaatcc 1740
gacgagcatg gaaagacctt acggttgaca ttgccagagg gttaagtgg agacgagaaa 1800
tcccagtggc ttttgacgat taaagcagtc gttcaaagtg ccaaactg gaatctggca 1860
gagtgcacat tgaagcatc gggagaaggg gtcatcataa aaagcgcca gataactccg 1920
gatgtatata aggtcactcc agtgatgaac acacatccgt accaatcaga agccgtatca 1980
gatgtttggt ctctctcaaa gacatccatg actttccaag ccaagaaagc aagtcttcag 2040
cctctcacca tatccttgga tgaattgttc tcatctagag gagaattcat ctctgtcgga 2100
ggtaacggac gaatgtctca taagaggcc atcctgctcg gtctgaggta caaaaagttg 2160
tacaatcagg cgagagtcaa atattctctg tagactatga aaaaagtaa cagatatcac 2220
aatctaagtg ttatcccaat ccattcatca tgagttcctt aaagaagatt ctcggtctga 2280
aggggaaagg taagaaatct aagaaattag ggatcgcacc accccttat gaagaggaca 2340
ctaacatgga gtatgtccg agcgctccaa ttgacaatc ctattttgag ttgacgaga 2400
tggacactca tgatccgaat caattaagat atgagaaatt cttctttaca gtgaaaatga 2460
cggttagatc taatcgtccg ttcagaacat actcagatgt ggcagccgct gtatcccatt 2520
gggatcacat gtacatcgga atggcaggga acgtccctt ctacaagatc ttggctttt 2580
tgggttcttc taatctaaag gccactccag cggtattggc agatcaaggt caaccagagt 2640
atcatgctca ctgtgaaggc agggcttatt tgccacacag aatggggaag accccctcca 2700
```

```
tgctcaatgt accagagcac ttcagaagac cattcaatat aggtctttac aagggaacga  2760
ttgagctcac aatgaccatc tacgatgatg agtcactgga agcagctcct atgatctggg  2820
atcatttcaa ttcttccaaa ttttctgatt tcagagagaa ggccttaatg tttggcctga  2880
ttgtcgagaa aaaggcatct ggagcttggg tcctggattc tgtcagccac ttcaaatgag  2940
ctagtctagc ttccagcttc tgaacaatcc ccggtttact cagtctctcc taattccaga  3000
ctttcgaaca actaatatcc tgtcttctct atcccgatga aaaaaactaa cagagatcga  3060
tctgttcct tgacaccatg aagtgccttt tgtacttagc ttttttattc atcggggtga  3120
attgcaagtt caccatagtt tttccacaca accaaaaagg aaactggaaa aatgttcctt  3180
ccaattacca ttattgcccg tcaagctcag atttaaattg gcataatgac ttagtaggca  3240
cagccttaca agtcaaaatg cccaagagtc acaaggctat tcaagcagac ggttggatgt  3300
gtcatgcttc caaatgggtc actacttgtg atttccgctg gtacggaccg aagtatataa  3360
cacattccat ccgatccttc actccatctg tagaacaatg caaggaaagc attgaacaaa  3420
cgaaacaagg aacttggctg aatccaggct tccctcctca aagttgtgga tatgcaactg  3480
tgacggatgc tgaagcagcg attgtccagg tgactcctca ccatgtgctt gttgatgaat  3540
acacaggaga atgggttgat tcacagttca tcaacgaaa atgcagcaat gacatatgcc  3600
ccactgtcca taactccaca acctggcatt ccgactataa ggtcaaaggg ctatgtgatt  3660
ctaacctcat ttccatggac atcaccttct tctcagagga cggagagcta tcatccctag  3720
gaaagaaggg cacagggttc agaagtaact actttgctta tgaaactgga gacaaggcct  3780
gcaaaatgca gtactgcaag cattgggag tcagactccc atcaggtgtc tggttcgaga  3840
tggctgataa ggmtctcttt gctgcagcca gattccctga atgcccagaa gggtcaagta  3900
tctctgctcc atctcagacc tcagtggatg taagtctcat tcaggacgtt gagaggatct  3960
tggattattc cctctgccaa gaaacctgga gcaaaatcag agcgggtctt cccatctctc  4020
cagtggatct cagctatctt gctcctaaaa acccaggaac cggtcctgtc tttaccataa  4080
tcaatggtac cctaaaatac tttgagacca gatacatcag agtcgatatt gctgctccaa  4140
tcctctcaag aatggtcgga atgatcagtg gaactaccac agaaagggta ctgtgggatg  4200
actgggctcc atatgaagac gtggaaattg gacccaatgg agttctgagg accagttcag  4260
gatataagtt tccttatat atgattggac atggtatgtt ggactccgat cttcatctta  4320
gctcaaaggc tcaggtgttt gaacatcctc acattcaaga cgctgcttcg cagcttcctg  4380
atggtgagac tttatttttt ggtgatactg ggctatccaa aaatccaatc gagtttgtag  4440
aaggttggtt cagtagttgg aagagctcta ttgcctcttt tttctttacc ataggggttaa  4500
tcattggact attcttggtt ctccgagttg gtatttatct ttgcattaaa ttaaagcaca  4560
ccaagaaaag acagatttat acagacatag agatgaaccg acttggaaag taactcaaat  4620
cctgcacaac agattcttca tgtttgaacc aaatcaactt gtgatatcat gctcaaagag  4680
gccttaatta tattttaatt tttaattttt atgaaaaaaa ctaacagcaa tcatggaagt  4740
ccacgatttt gagaccgacg agttcaatga tttcaatgaa gatgactatg ccacaagaga  4800
attcctgaat cccgatgagc gcatgacgta cttgaatcat gctgattaca atttgaattc  4860
tcctctaatt agtgatgata ttgacaattt gatcaggaaa ttcaattctc ttccgattcc  4920
ctcgatgtgg gatagtaaga actgggatgg agttcttgag atgttaacat catgtcaagc  4980
caatcccatc tcaacatctc agatgcataa atggatggga agttggttaa tgtctgataa  5040
tcatgatgcc agtcaagggt atagttttt acatgaagtg gacaaagagg cagaaataac  5100
atttgacgtg gtggagacct tcatccgcgg ctggggcaac aaaccaattg aatacatcaa  5160
aaaggaaaga tggactgact cattcaaaat tctcgcttat ttgtgtcaaa agttttttgga  5220
cttacacaag ttgacattaa tcttaaatgc tgtctctgga gtggaattgc tcaacttggc  5280
gaggactttc aaaggcaaag tcagaagaag ttctcatgga acgaacatat gcaggattga  5340
ggttccagc ttgggtccta cttttatttc agaaggatgg gcttacttca agaaacttga  5400
tattctaatg gaccgaaact ttctgttaat ggtcaaagat gtgattatag ggaggatgca  5460
aacggtgcta tccatggtat gtagaataga caacctgttc tcagagcaag acatcttctc  5520
ccttctaaat atctcacagaa ttggagataa aattgtggaa aggcagggaa attttttctta  5580
tgacttgatt aaaatggtgg aaccgatatg caacttgaag ctgatgaaat tagcaagaga  5640
atcaaggcct ttagtcccac aattccctca ttttgaaaat catatcaaga cttctgttga  5700
tgaaggggca aaaattgacc gaggtataag attcctccat gatcagataa tgagtgataa  5760
aacagtggat ctcacactgg tgatttatgt atcgttcaga cattgggtc atcctttat  5820
agattattac actggactag aaaaattaca ttcccaagta accatgaaga aagatattga  5880
tgtgtcatat gcaaaagcac ttgcaagtga tttagctcgg attgttctat ttcaacagtt  5940
caatgatcat aaaaagtggt tcgtgaatgg agacttgctc cctcatgatc atcccttta  6000
aagtcatgtt aaagaaaata catggcctac agctgctcaa gttcaagatt ttggagataa  6060
atggcatgaa cttccgctga ttaaatgttt tgaaatacc gacttactag acccatcgat  6120
aatatactct gacaaaagtc attcaatgaa taggtcagag gtgttgaaac atgtccgaat  6180
gaatccgaac actcctatcc ctagtaaaaa ggtgttgcag actatgttgg acacaaaggc  6240
taccaattgg aaagaatttc ttaaagagat tgatgagaag ggctagatg atgatgatct  6300
aattattggt cttaaggaa aggagaggga actgaagttg gcaggtagat tttcttccct  6360
aatgtcttga aaattgcgag aatactttgt aattaccgaa tatttgataa agactcattt  6420
cgtccctatg tttaaaggcc tgacaatggc ggacgatcta actgcagtca ttaaaaagat  6480
gttagattcc tcatccggcc aaggattgaa gttcaatgca gcaatttgca tagccaatca  6540
cattgattac gaaaatgga ataaccacca aaggaagtta tcaaacggcc cagtgttccg  6600
agttatgggc cagttcttag gttatccatc cttaatcgag agaactcatg aattttttga  6660
gaaagtctct atatactaca atggaagacc agacttgatg cgtgttcaca caacacact  6720
gatcaattca acctcccaac gagtttgttg gcaaggacaa gagggtggag tggaaggtct  6780
acggcaaaaa ggatggagta tcctcaatct actggttatt caagagagg ctaaaatcag  6840
aaacactgct gtcaaagtct ggcacaagg tgataatcaa gttatttgca cacagtataa  6900
aacgaagaaa tcgagaaacg ttgtagaatt acagggtgct ctcaatcaaa tggtttctaa  6960
taatgagaaa attatgactg caatcaaaat agggacaggg aagttaggac ttttgataaa  7020
tgacgatgag actatgcaat ctgcagatta cttgaattat ggaaaaatac cgatttttcg  7080
tggagtgatt agaggggttag agaccaagag tgtcacga gtgacttgtg tcaccaatga  7140
ccaaatacccc acttgtgcta atataatgag ctcagttccc acaaatgctc tcaccgtagc  7200
tcattttgct gagaacccaa tcaatgccat gatacagtac aattattttg gacatttgc  7260
tagactcttg ttgatgatgc atgatcctgc tcttcgtcaa tcattgtatg aagttcaaga  7320
taagataccg ggcttgcaca gttctacttt caaatacgcc atgttgtatt tggacccttc  7380
cattggagga gtgtcgggca tgtctttgtc caggtttttg attagagcct tcccagatcc  7440
```

```
cgtaacagaa agtctctcat tctggagatt catccatgta catgctcgaa gtgagcatct      7500
gaaggagatg agtgcagtat ttggaaaccc cgagatagcc aagtttcgaa taactcacat      7560
agacaagcta gtagaagatc caacctctct gaacatcgct atgggaatga gtccagcgaa      7620
cttgttaaag actgaggtta aaaaatgctt aatcgaatca agacaaacca tcaggaacca      7680
ggtgattaag gatgcaacca tatatttgta tcatgaagga gatcggctca gaagtttctt      7740
atggtcaata aatcctctgt tccctagatt tttaagtgaa ttcaaatcag gcactttttt      7800
gggagtcgca gacgggctca tcagtctatt tcaaaattct cgtactattc ggaactcctt      7860
taagaaaaag tatcataggg aattggatga tttgattgtg aggagtgagg tatcctcttt      7920
gacacattta gggaaacttc atttgagaag gggatcatgt aaaatgtgga catgttcagc      7980
tactcatgct gacacattaa gatacaaatc ctggggccgt acagttattg ggacaactgt      8040
accccatcca ttagaaatgt tgggtccaca acatcgaaaa gagactcctt gtgcaccatg      8100
taacacatca gggttcaatt atgtttctgt gcattgtcca gacgggatcc atgacgtctt      8160
tagttcacgg ggaccattgc ctgcttatct agggtctaaa acatctgaat ctacatctat      8220
tttgcagcct tgggaaaggg aaagcaaagt cccactgatt aaaagagcta cacgtcttag      8280
agatgctatc tcttggtttg ttgaacccga ctctaaacta gcaatgacta ctttctaa       8340
catccactct ttaacaggcg aagaatggac caaaaggcag catgggttca aaagaacagg      8400
gtctgccctt cataggtttt cgacatctcg gatgagccat ggtgggttcg catctcagag      8460
cactgcagca ttgaccaggt tgatggcaac tacagacacc atgagggatc tgggagatca      8520
gaatttcgac tttttattcc aagcaacgtt gctctatgct caaattacca ccactgttgc      8580
aagagacgga tggatcacca gttgtacaga tcattatcat attgcctgta agtcctgttt      8640
gagacccata aagagagatca ccctggactc aagtatggac tacacgcccc cagatgtatc      8700
ccatgtgctg aagacatgga ggaatgggga aggttcgtgg ggacaagaga taaaacagat      8760
ctatcctta gaagggaatt ggaagaattt agcacctgct gagcaatcct atcaagtcgg      8820
cagatgtata ggttttctat atggagactt ggcgtataga aaatctactc atgccgagga      8880
cagttctcta tttcctctat ctatacaagg tcgtattaga ggtcgaggtt cttaaaagg      8940
gttgctagac ggattaatga gagcaagttg ctgccaagta ataccggga gaagtctgc      9000
tcatttgaag aggccggcca acgcagtgta cggaggtttg atttacttga ttgataaatt      9060
gagtgtatca cctccattcc tttctcttac tagatcagga cctattagag acgaattaga      9120
aacgattccc cacaagatcc caacctccta tccgacaagc aaccgtgata tggggtgat      9180
tgtcagaaat tacttcaaat accaatgccg tctaattgaa aagggaaaat acagatcaca      9240
ttattcacaa ttatggttat tctcagatgt cttatccata gacttcattg gaccattctc      9300
tatttccacc accctcttgc aaatcctata caagccatt ttatctggga aagataagaa      9360
tgagttgaga gagctggcaa atctttcttc attgctaaga tcaggagagg ggtgggaaga      9420
catacatgtg aaattcttca ccaaggacat attattgtgt tcagaggaaa tcagacatgc      9480
ttgcaagttc gggattgcta aggataataa taaagacatg agctatcccc cttggggaag      9540
ggaatccaga gggacaatta caacaatccc tgtttattat acgaccaccc cttacccaaa      9600
gatgctagag atgcctccaa gaatccaaaa tccctgctg tccggaatca ggttgggcca      9660
attaccaact ggcgctcatt ataaaattcg gagtatatta catggaatgg gaatccatta      9720
cagggacttc ttgagttgtg gagacggctc cggagggatg actgctgcat tactacgaga      9780
aaatgtgcat agcagaggaa tattcaatag tctgttagaa ttatcagggt cagtcatgcg      9840
aggcgcctct cctgagcccc ccagtgccct agaaacttta ggaggagata aatcgagatg      9900
tgtaaatggt gaaacatgtt gggaatatcc atctgactta tgtgacccaa ggcacttggga      9960
ctatttcctc cgactcaaag caggcttggg gcttcaaatt gatttaattg taatggatat     10020
ggaagttcgg gattcttcta ctagcctgaa aattgagacg aatgttagaa attatgtcca     10080
ccggatttg gatgagcaag gagttttaat ctacaagact tatgaacat atatttgtga     10140
gagcgaaaag aatcagtaa caatccttgg tcccatgttc aagacggtcg acttagttca     10200
aacagaattt agtagttctc aacgtctga agtatatatg gtatgtaagg ttttgaagaa     10260
attaatcgat gaacccaatc ccgattggtc ttccatcaat gaatcctgga aaaacctgta     10320
cgcattccag tcatcagaac aggaatttgc cagagcaaag aaggttagta catactttac     10380
cttgacaggt attccctccc aattcattcc tgatccttt gtaaacattg agactatgct     10440
acaaatattc ggagtaccca cgggtgtgtc tcatgcggtc gccttaaaat catctgatag     10500
acctgcagat ttattgacca ttagccttt ttatatggcg attatatcgt attataacat     10560
caatcatatc agagtaggac cgataacccc gaaccccca tcagatgaa ttgcacaaaa     10620
tgtggggatc gctataactg gtataagctt ttggctgagt tgatggaga agacattcc     10680
actatatcaa cagtgtttag cagttatcca gcaatcattc ccgattaggt gggaggctgt     10740
ttcagtaaaa ggaggataca agcagaagtg gagtactaga ggtgatgggc tcccaaaaga     10800
tacccgaatt tcagactcct tggccccaat cgggaactgg atcagatctc tggaattggt     10860
ccgaaaccaa gttcgtctaa atccattcaa tgagatcttg ttcaatcagc tatgtcgtac     10920
agtggataat cattttgaaat ggtcaaattt gcgaagaaac acaggaatga ttgaatggat     10980
caatagacga atttcaaaag aagaccggtc tatactgatg ttgaagagtg acctacacga     11040
ggaaaactct tggagagatt aaaaaatcat gaggagactc caaacttaa gtatgaaaaa     11100
aactttgatc cttaagaccc tcttgtggtt ttattttttt atctggtttt gtggtcttcg     11160
t                                                                     11161

SEQ ID NO: 9            moltype = DNA   length = 1489
FEATURE                 Location/Qualifiers
source                  1..1489
                        mol_type = other DNA
                        note = Vesicular stomatitis indiana virus
                        organism = unidentified
SEQUENCE: 9
atagtcgaga cgacgaagac aaacaaacca ttattatcat taaaaggctc aggagaaact       60
ttaacagtaa tcaaaatgtc tgttacagtc aagagaatca ttgacaacac agtcatagtt      120
ccaaaacttc ctgcaaatga ggatccagtg gaatacccag cagattactt cagaaaatca      180
aaggagattc tctttacat caatactaca aaaagtttgt cagatctaag aggatatatc      240
taccaaggcc tcaaatccgg aaatgtatca atcatacatg tcaacagcta cttgtatgga      300
gcattgaagg acatccgggg taagttggat aaagattggt caagtttcgg aataaacatc      360
gggaaggcag gggatacaat cggaatattt gaccttgtat ccttgaaagc cctggacggt      420
gtacttccag atgagtatc ggatgcttcc agaaccagcc cagatgacaa atggttgcct      480
```

```
ttgtatctac ttggcttata cagagtgggc agaacacaaa tgcctgaata cagaaaaagg    540
ctcatggatg ggctgacaaa tcaatgcaaa atgatcaatg aacagtttga acctcttgtg    600
ccagaaggtc gtgacatttt tgatgtgtgg ggaaatgaca gtaattacac aaaaattgtc    660
gctgcagtgg acatgttctt ccacatgttc aaaaaacatg aatgtgcctc gttcagatac    720
ggaactattg tttccagatt caaagattgt gctgcattgg caacatttgg acacctctgc    780
aaaataaccg gaatgtctac agaagatgtg acgacctgga tcttgaaccg agaagttgca    840
gatgagatgt ccaaatgat gcttccaggc caagaaattg acaaggctga ttcatacatg    900
ccttatttga tcgactttgg attgtcttct aagtctccat attcttccgt caaaaaccct    960
gccttccact tctggggca attgacagct tttctgctca gatccaccag agcaaggaat   1020
gcccgacagc ctgatgacat tgagtataca tctcttacta cagcaggttt gttgtacgct   1080
tatgcagtag gatcctctgc tgacttggca caacagtttt gtgttggaga tagcaaatac   1140
actccagatg atagtaccgg aggattacga actaatgcac cgccacaagg cagagatgtg   1200
gtcgaatggc tcggatggtt tgaagatcaa aacagaaaac cgactcctga tatgatgcag   1260
tatgcgaaac gagcagtcat gtcactgcaa ggcctaagag agaagacaat tggcaagtat   1320
gctaagtcag agtttgacaa atgacccat aattctcaga tcacctatta tatattatgc   1380
tagcttgttc gaactcttaa ttaacgcccc gagtatgtcg acgtacttaa gacctctttg   1440
tggttttat tttttatctg gttttgtggt cttcgtcgtc tccggccgg                1489

SEQ ID NO: 10          moltype = DNA   length = 1645
FEATURE                Location/Qualifiers
source                 1..1645
                       mol_type = other DNA
                       note = Vesicular stomatitis indiana virus
                       organism = unidentified
SEQUENCE: 10
gctagctatg aaaaaaacta acagatatca tggataatct cacaaaagtt cgtgagtatc     60
tcaagtccta ttctcgtcta gatcaggcgg taggagagat agatgagatc gaagcacaac    120
gagctgaaaa gtccaattat gagttgttcc aagaggacgg agtggaagag catactaggc    180
cctcttattt tcaggcagca gatgattctg acacagaatc tgaaccagaa attgaagaca    240
atcaaggctt gtatgtacca gatccggaag ctgagcaagt tgaaggcttt atacaggggc    300
ctttagatga ctatgcagat gaggacgtgg atgttgtatt cacttcggac tggaaacagc    360
ctgagcttga atccgacgag catggaaaga ccttacggtt gacattgcca gagggtttaa    420
gtggagagca gaaatcccag tggcttttga cgattaaagc agtcgttcaa agtgccaaac    480
actggaatct ggcagagtgc acatttgaag catcggaga aggggtcatc ataaaaaagc    540
gccagataac tccggatgta tataaggtca ctccagtgat gaacacacat ccgtcccaat    600
cagaagccgt atcagatgtt tggtctctct caaagacatc catgactttc aacccaaga    660
aagcaagtct tcagcctctc accatatcct tggatgaatt gttctcatct agaggagaat    720
tcatctctgt cggaggtaac ggacgaatgt ctcataaaga ggccatcctg ctcggtctga    780
ggtacaaaaa gttgtacaat caggcgagag tcaaatattc tctgtagact agtatgaaaa    840
aaagtaacag atatcacaat ctaagtgtta tcccaatcca ttcatcatga gttccttaaa    900
gaagattctc ggtctgaagg ggaaaggtaa gaaatctaag aaattaggga tcgcaccacc    960
cccttatgaa gaggacacta acatggagta tgctccgagc gctccaattg acaaatccta   1020
ttttggagtt gacgagatgg acactcatga tccgaatcaa ttaagatatg agaaattctt   1080
ctttacagtg aaaatgacgg ttagatctaa tcgtccgttc agaacatact cagatgtggc   1140
agccgctgta tcccattggg atcacatgta catcggaatg gcagggaaac gtcccttcta   1200
caagatcttg gcttttttgg gttcttcta tctaaaggcc actccagcgg tattggcaga   1260
tcaaggtcaa ccagatgtatc atgctcactg tgaaggcagg gcttatttgc cacacagaat   1320
ggggaagacc cctcccatgc tcaatgtacc agagcactc agaagaccat tcaatatagg   1380
tctttacaag ggaacgattg agctcacaat gaccatctac gatgatgagt cactggaagc   1440
agctcctatg atctgggatc atttcaattc ttccaaattt tctgatttca gagagaaggc   1500
cttaatgttt ggcctgattg tcgagaaaaa ggcatctgga gcttgggtcc tggattctgt   1560
cagccacttc aaatgagcta gtctagcttc cagcttctga acaatcccg gtttactcag   1620
tctctcctaa ttccagcctt tcgaa                                         1645

SEQ ID NO: 11          moltype = DNA   length = 1645
FEATURE                Location/Qualifiers
source                 1..1645
                       mol_type = other DNA
                       note = Vesicular stomatitis indiana virus
                       organism = unidentified
SEQUENCE: 11
gctagctatg aaaaaaacta acagatatca tggataatct cacaaaagtt cgtgagtatc     60
tcaagtccta ttctcgtcta gatcaggcgg taggagagat agatgagatc gaagcacaac    120
gagctgaaaa gtccaattat gagttgttcc aagaggacgg agtggaagag catactaggc    180
cctcttattt tcaggcagca gatgattctg acacagaatc tgaaccagaa attgaagaca    240
atcaaggctt gtatgtacca gatccggaag ctgagcaagt tgaaggcttt atacaggggc    300
ctttagatga ctatgcagat gaggacgtgg atgttgtatt cacttcggac tggaaacagc    360
ctgagcttga atccgacgag catggaaaga ccttacggtt gacattgcca gagggtttaa    420
gtggagagca gaaatcccag tggcttttga cgattaaagc agtcgttcaa agtgccaaac    480
actggaatct ggcagagtgc acatttgaag catcggaga aggggtcatc ataaaaaagc    540
gccagataac tccggatgta tataaggtca ctccagtgat gaacacacat ccgtcccaat    600
cagaagccgt atcagatgtt tggtctctct caaagacatc catgactttc aacccaaga    660
aagcaagtct tcagcctctc accatatcct tggatgaatt gttctcatct agaggagaat    720
tcatctctgt cggaggtaac ggacgaatgt ctcataaaga ggccatcctg ctcggtctga    780
ggtacaaaaa gttgtacaat caggcgagag tcaaatattc tctgtagact agtatgaaaa    840
aaagtaacag atatcacaat ctaagtgtta tcccaatcca ttcatcatga gttccttaaa    900
gaagattctc ggtctgaagg ggaaaggtaa gaaatctaag aaattaggga tcgcaccacc    960
cccttatgaa gaggacacta acatggagta tgctccgagc gctccaattg acaaatccta   1020
ttttggagtt gacgagatgg acactcatga tccgaatcaa ttaagatatg agaaattctt   1080
```

```
ctttacagtg aaaatgacgg ttagatctaa tcgtccgttc agaacatact cagatgtggc   1140
agccgctgta tcccattggg atcacatgta catcggaatg gcaggaaaac gtccttcta    1200
caagatcttg gctttttgg gttcttctaa tctaaaggcc actccagcgg tattggcaga    1260
tcaaggtcaa ccagagtatc atgctcactg tgaaggcagg gcttatttgc cacacagaat   1320
ggggaagacc cctcccatgc tcaatgtacc agagcacttc agaagaccat tcaatataqg   1380
tctttacaag ggaacgattg agctcacaat gaccatctac gatgatgagt cactggaagc   1440
agctcctatg atctgggatc atttcaattc ttccaaattt tctgatttca gagagaaggc   1500
cttaatgttt ggcctgattg tcgagaaaaa ggcatctgga gcttgggtcc tggattctgt   1560
cagccacttc aaatgagcta gtctagcttc cagcttctga acaatcccg gtttactcag    1620
tctctcctaa ttccagcctt tcgaa                                         1645

SEQ ID NO: 12         moltype = DNA   length = 2851
FEATURE               Location/Qualifiers
source                1..2851
                      mol_type = other DNA
                      note = Vesicular stomatitis indiana virus
                      organism = unidentified
SEQUENCE: 12
ttaattaaat tttaatttt aattttatg aaaaaaacta acagcaatca tggaagtcca     60
cgattttgag accgacgagt tcaatgattt caatgaagat gactatgcca aagagaatt    120
cctgaatccc gatgagcgca tgacgtactt gaatcatgct gattacaatt tgaattctcc   180
tctaattagt gatgatattg acaatttgat caggaaattc aattctcttc cgattccctc   240
gatgtgggat agtaagaact gggatggagt tcttgagatg ttaacatcat gtcaagccaa   300
tcccatctca acatctcaga tgcataaatg gatgggaagt tggttaatgt ctgataatca   360
tgatgccagt caagggtata gttttttaca tgaagtggac aaagaggcag aaataacatt   420
tgacgtggtg gagaccttca tccgcggctg gggcaacaac ccaattgaat acatcaaaaa   480
ggaaagatgg actgactcat tcaaaattc cgcttatttg tgtcaaaagt ttttggactt    540
acacaagttg acattaatct aaatgctgt ctctgaggtg gaattgctca acttggcgag    600
gactttcaaa ggcaaagtca aagaagttc tcatggaacg aacatatgca ggcttagggt    660
tcccagcttg ggtcctactt ttatttcaga aggatggctg tacttcaaga aacttgatat   720
tctaatggac cgaaactttc tgttaatggt caaagatgtg attatagga ggatgcaaac    780
ggtgctatcc atggtatgta gaatagcaaa cctgttctca gagcaagaca tcttctccct   840
tctaaatatc tacagaattg gagataaaat tgtggagagg cagggaaatt tttcttatga   900
cttgattaaa atggtggaac cgatatgcaa cttgaagcg atgaaattga caagagaatc    960
aaggcctta gtcccacaat tccctcattt tgaaatcat atcaagactt ctgttgatga    1020
aggggcaaaa attgaccgag gtataagatt cctccatgat cagataatga gtgtgaaaac   1080
agtggatctc acactggtga tttatggatc gttcagacat tgggqtcatc ctttatata    1140
ttattacgct ggactagaaa aattcattc ccaagtaacc atgaagaaag atattgatgt    1200
gtcatatgca aaagcacttg caagtgattt agctcggatt gttctatttc aacagttcaa   1260
tgatcataaa aagtggttcg tgaatggaga cttgctccct catgatcatc cctttaaaag   1320
tcatgttaaa gaaaatacat ggcctacagc tgctcaagtt caagattttg gagataaatg   1380
gcatgaactt ccgctgatta aatgttttga aatacccgac ttactagacc catcgataat   1440
atactctgac aaaagtcatt caatgaatag gtcaagagtg ttgaaacatg tccgaatgaa   1500
tccgaacact cctatcccta gtaaaaaggt gttgcagact atgttggaca caaaggctac   1560
caattggaaa gaatttctta agagattga tgagaagggc ttagatgatg atgatctaat    1620
tattggtctt aaaggaaagg agagggaact gaagttggca ggtagatttt tctcccctaat   1680
gtcttggaaa ttgcgagaat actttgtaat taccgaatat ttgataaaga ctcattcgt    1740
ccctatgttt aaaggcctga caatggcgga cgatctaact gcagtcatta aaagagtgtt   1800
agattcctca tccggccaag gattgaagtc atatgaggca atttgcatag ccaatcacat   1860
tgattacgaa aaatgaata accaccaaag gaagttatca acggcccag tgttccgagt     1920
tatgggccag ttcttaggtt atccatcctt aatcgagaga actcatgaat tttttggaaa   1980
aagtcttata tactacaatg gaagaccaga cttgatgcgt gttcacaaca acacactgat    2040
caattcaacc tcccaacgag tttgttggca aggacaagag ggtggactgg aagtctacg    2100
gcaaaaagga tggagtatcc tcaatctact ggttattcaa agagaggcta aaatcagaaa   2160
cactgctgtc aaagtcttgg cacaaggtga taatcaagtt atttgcacac agtataaaac   2220
gaagaaatcg agaacgttg tagaattaca gggtgctctc aatcaaatgg tttctaataa    2280
tgagaaaatt atgactgcaa tcaaaatagg gacaggaag ttaggacttt tgataaatga    2340
cgatgagact atgcaatctg cagattactt gaattatgga aaaatacccga ttttccgtgg   2400
agtgattaga gggttagaga ccaagagatg gtcacgagtg gttgtgtca ccaatgacca    2460
aataccccact tgtgctaata taatgagctc agttttccaca aatgctctca ccgtagctca    2520
ttttgctgag aacccaatca atgccatgat acagtacaat tatttggga catttgctag    2580
actcttgttg atgatgcatg atcctgctct tcgtcaatca ttgtatgaag ttcaagataa   2640
gataccgggc ttgcacagtt ctactttcaa atacgccatg ttgtatttgg accttccat    2700
tggaggagtg tcgggcatgt cttttgtccag gttttgatt agagccttcc cagatcccgt    2760
aacagaaagt ctctcattct ggagattcat ccatgtacat gctcgaagtg agcatctgaa   2820
ggagatgagt gcagtatttg gaaacccccga g                                  2851

SEQ ID NO: 13         moltype = DNA   length = 2664
FEATURE               Location/Qualifiers
source                1..2664
                      mol_type = other DNA
                      note = Vesicular stomatitis indiana virus
                      organism = unidentified
SEQUENCE: 13
cccgagatag ccaagttccg aataactcac atagacaagc tagtagaaga tccaacctct     60
ctgaacatcg ctatgggaat gagtccagcg aacttgttaa agactgaggt taaaaaatgc    120
ttaatcgaat caagacaaac catcaggaac caggtgatta aggatgcaac catatatttg    180
tatcatgaag aggatcggct cagaagtttc ttatggtcaa taaatcctct gttccctaga    240
tttttaagtg aattcaaatc aggcactttt ttggagtcg cagacgggct catcagtcta    300
```

```
tttcaaaatt ctcgtactat tcggaactcc tttaagaaaa agtatcatag ggaattggat    360
gatttgattg tgaggagtga ggtatcctct ttgacacatt tagggaaact tcatttgaga    420
aggggatcat gtaaaatgtg gacatgttca gctactcatg ctgacacatt aagatacaaa    480
tcctggggcc gtacagttat tgggacaact gtaccccatc cattagaaat gttgggtcca    540
caacatcgaa aagagactcc ttgtgcacca tgtaacacat cagggttcaa ttatgtttct    600
gtgcattgtc cagacgggat ccatgacgtc tttagttcac ggggaccatt gcctgctat    660
ctagggtcta aaacatctga atctacatct attttgcagc cttgggaaag ggaaagcaaa    720
gtcccactga ttaaaagagc tacacgtctt agagatgcta tctcttggtt tgttgaaccc    780
gactctaaac tagcaatgac tatactttct aacatccact ctttaacagg cgaagaatgg    840
accaaaaggc agcatgggtt caaaagaaca gggtctgccc ttcataggtt ttcgacatct    900
cggatgagcc atggtgggtt cgcatctcag agcactgcag cattgaccag gttgatggca    960
actacagaca ccatgaggga tctgggagat cagaatttcg acttttttatt ccaagcaaca    1020
ttgctctatg ctcaaattac caccactgtt gcaagagacg gatggatcac cagttgtaca    1080
gatcattatc atattgcctg taagtcctgt ttgagaccta tgaagagat cacccgtgac    1140
tcaagtatgg actacacgcc cccagatgta tcccatgtgc tgaagacatg gaggaatggg    1200
gaaggttcgt ggggacaaga gataaaacag atctatcctt tagaagggaa ttggaagaat    1260
ttagcacctg ctgagcaatc ctatcaagtc ggcagatgta taggttttct atatggagac    1320
ttggcgtata gaaaatctac tcatgccgag gacagttctc tatttcctct atctatacaa    1380
ggtcgtatta gaggtcgagg tttcttaaaa gggttgctag acggattaat gagagcaagt    1440
tgctgccaag taatacaccg gagaagtctg gctcatttga agaggccggc caacgcagtg    1500
tacggaggtt tgatttactt gattgataaa ttgagtgtat cacctccatt cctttctctt    1560
actagatcag gacctattag agacgaatta gaaacgattc cccacaagat cccaacctcc    1620
tatccgacaa gcaaccgtga tatggggtg attgtcagaa attacttcaa ataccaatgc    1680
cgtctaattg aaaagggaaa atacagatca cattattcac aattatggtt attctcagat    1740
gtcttatcca tagacttcat tggaccattc tctatttcca ccaccctctt gcaaatccta    1800
tacaagccat ttttatctgg gaaagataag aatgagttga gagagctggc aaatctttct    1860
tcattgctaa gatcaggaga ggggtggaa gacatacatg tgaaattctt caccaaggac    1920
atattattgt gtccagagga aatcagacat gcttgcaagt tcgggattgc taaggataat    1980
aataaagaca tgagctatcc cccttgggga agggaatcca gagggacaat tacaacaatc    2040
cctgttttatt atacgaccac cccttaccca aagatgcctcc aagaatccaa    2100
aatcccctgc tgtccggaat caggttgggc caattaccaa ctggcgctca ttataaaatt    2160
cggagtatat tacatggaat gggaatccat tacagggact tcttgagttg tggagacggc    2220
tccgagggga tgactgctgc attactacga gaaaatgtgc atagcagagg aatattcaat    2280
agtctgttag aattatcagg gtcagtcatg cgaggcgcct ctcctgagcc cccagtgtg    2340
ctagaaactt taggaggaga taaatcgaga tgtgtaaatg gtgaaacatg ttgggaatat    2400
ccatctgact tatgtgaccc aaggacttgg gactatttcc tccgactcaa agcaggcttg    2460
gggcttcaaa ttgatttaat tgtaatggat atggaagttc gggattcttc tactagcctg    2520
aaaattgaga cgaatgttag aaatattgtg caccggattt tggatgagca aggagtttta    2580
atctacaaga cttatggaac atatatttgt gagagcgaaa agaatgcagt aacaatcctt    2640
ggtccatgt tcaagacggt cgac                                          2664

SEQ ID NO: 14            moltype = DNA  length = 930
FEATURE                  Location/Qualifiers
source                   1..930
                         mol_type = other DNA
                         note = Vesicular stomatitis indiana virus
                         organism = unidentified
SEQUENCE: 14
gtcgacttag ttcaaacaga atttagtagt tctcaaacgt ctgaagtata tatggtatgt     60
aaaggtttga agaaattaat cgatgaaccc aatcccgatt ggtcttccat caatgaatcc    120
tggaaaaacc tgtacgcatt ccagtcatca gaacaggaat ttgccagagc aaagaaggtt    180
agtacatact ttaccttgac aggtattccc tcccaattca ttcctgatcc ttttgtaaac    240
attgagacta tgctacaaat attcggagta cccacgggtg tgtctcatgc ggctgcctta    300
aaatcatctg atagacctgc agatttattg accattagcc ttttttatat ggcgattata    360
tcgtattata acatcaatca tatcagagta ggaccgaacc tccgaaccc cccatcagat    420
ggaattgcac aaaatgtggg gatcgctata actggtataa gcttttggct gagtttgatg    480
gagaaagaca ttccactata tcaacagtgt ttagcagtta ccagcaatc attcccgatt    540
aggtgggagg ctgtttcagt aaaaggagga tacaagcaga gtggagtac tagaggtgat    600
gggctcccaa aagatacccg aatttcagac tccttggcc caatcgggaa ctggatcaga    660
tctctggaat tggtccgaaa ccaagttcgt ctaaatccat tcaatgagat cttgttcaat    720
cagctatgtc gtacagtgga taatcatttg aaatggtcaa atttgcgaaa aacacagga    780
atgattgaat ggatcaatag acgaatttca aagaagacc ggtctatact gatgttgaag    840
agtgacctac acgaggaaaa ctcttggaga gattaaaaaa tcatgaggag actccaaact    900
ttaagtatga aaaaacttt gatccttaag                                     930

SEQ ID NO: 15            moltype = DNA  length = 23
FEATURE                  Location/Qualifiers
source                   1..23
                         mol_type = other DNA
                         note = Vesicular stomatitis indiana virus
                         organism = unidentified
SEQUENCE: 15
tatgaaaaaa actaacagat atc                                            23

SEQ ID NO: 16            moltype = DNA  length = 23
FEATURE                  Location/Qualifiers
source                   1..23
                         mol_type = other DNA
                         note = Vesicular stomatitis indiana virus
```

```
                        organism = unidentified
SEQUENCE: 16
tatgaaaaaa agtaacagcg atc                                             23

SEQ ID NO: 17           moltype = DNA  length = 11164
FEATURE                 Location/Qualifiers
source                  1..11164
                        mol_type = other DNA
                        note = Vesicular stomatitis indiana virus
                        organism = unidentified
SEQUENCE: 17
acgaagacaa acaaaccatt attatcatta aaaggctcag gagaaacttt aacagtaatc     60
aaaatgtctg ttacagtcaa gagaatcatt gacaacacag tcatagttcc aaaacttcct    120
gcaaatgagg atccagtgga atacccggca gattacttca gaaaatcaaa ggagattcct    180
ctttacatca atactacaaa aagtttgtca gatctaagag gatatgtcta ccaaggcctc    240
aaatccggaa atgtatcaat catacatgtc aacagctact gtatggagc attgaaggac     300
atccggggta agttggataa agattggtca agtttcggaa taaacatcgg gaaggcaggg    360
gatacaatcg gaatatttga ccttgtatcc ttgaaagccc tggacggtgt acttccagat    420
ggagtatcgg atgcttccag aaccagcgca gatgacaaat ggttgccttt gtatctactt    480
ggcttataca gagtgggcag aacacaaatg cctgaataca gaaaaaggct catggatggg    540
ctgacaaatc aatgcaaaat gatcaatgaa cagtttgaac ctcttgtgcc agaaggtcgt    600
gacattttg atgtgtgggg aaatgacagt aattacacaa aaattgtcgc tgcagtggac     660
atgttcttcc acatgttcaa aaaacatgaa tgtgcctcgt tcagatacgg aactattgtt    720
tccagattca agattgtgc tgcattggca acatttggac acctctgcaa ataaccgga     780
atgtctacag aagatgtgac gacctggatc ttgaaccgag aagttgcaga tgagatggtc    840
caaatgatgc ttccaggcca agaaattgac aaggctgatt catacatgcc ttatttgatc    900
gactttggat tgtcttctaa gtctccatat tcttccgtca aaaaccctgc cttccacttc    960
tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgctg acttggcaca acagttttgt gttggagata gcaaatacac tccagatgat   1140
agtaccggag gattgacgac taatgcaccg ccacaaggcg agatgtggt cgaatgctc     1200
ggatggtttg aagatcaaaa cagaaaaccg actcctgata tgatgcagta tgcgaaacga   1260
gcagtcatgt cactgcaagg cctaagagag aagacaattg gcaagtatgc taagtcagag   1320
tttgacaaat gacccatata ttctcagatc acctattata tattatgca gctatgaaaa   1380
aaactaacag atatcatgga taatctcaca aaagttcgtg agtatctcaa gtcctattct   1440
cgtctagatc aggcggtagg agagatagat gagatcgaag cacaacgagc tgaaaagtcc   1500
aattatgagt tgttccaaga ggacggagtg gaagagcata ctaggccctc ttattttcag   1560
gcagcagatg attctgacac agaatctgaa ccagaaattg aagcaatca aggcttgtat    1620
gtaccagatc cggaagctga gcaagttgaa ggctttatac agggccttt agatgactat   1680
gcagatgagg acgtggatgt tgtattcact tcggactgga aacagcctga gcttaatcc    1740
gacgagcatg gaaagacctt acggttgaca ttgccagagg gtttaagtgg agagcagaaa   1800
tcccagtggc ttttgacgat taagcagtc gttcaaagtg ccaaacactg gaatctggca   1860
gagcacat ttgaagcatc gggagaaggg gtcatcataa aaaagcgcca gataactcag     1920
gatgtatata aggtcactcc agtgatgaac acacatccgt cccaatcaga gccgtcatca    1980
gatgtttggt ctctctcaaa gacatccatg actttccaac ccaagaaagc aagtcttcag   2040
cctctccacca tatccttgga tgaattgttc tcatctagag agaattcat ctctgtcgga    2100
ggtaacggac gaatgtctca taagaggcc atcctgctcg gtctgaggta caaaagttg     2160
tacaatcagg cgagagtcaa atattctctg tagactagta tgaaaaaaag taacagatat   2220
cacaatctaa gtgttatcc aatccattca tcatgagttc cttaaagaag attctcggtc    2280
tgaagggaa aggtaagaaa tctaagaaat tagggatcgc accaccccct tatgaagagg    2340
acactaacat ggagtatgct ccgagcgctc caattgacaa atcctatttt ggagttgaca   2400
agatggacac tcatgatccg aatcaattaa gatatgagaa attcttcttt acagtgaaaa   2460
tgacggttag atctaatcgt ccgttcagaa cactactcaga tgtggcagcc gctgtatccc   2520
attgggatca catgtacatc ggaatggcag ggaaacgtcc cttctacaag atcttggctt   2580
ttttgggttc ttctaatcta aaggccactc cagcggtatt ggcagatcaa ggtcaaccag   2640
agtatcatgc tcactgtgaa ggcagggctt atttgccaca cagaatgggg aagaccctc    2700
ccatgctcaa tgtaccagag cacttcagaa gaccattcaa tataggtctt tacaagggaa   2760
cgattgagct cacaatgacc atctacgatg atgagtcact ggaagcagct cctatgatct   2820
gggatcattt caattcttcc aaatttttctg atttcagaga gaaggcctta atgtttgcc    2880
tgattgtcga gaaaaaggca tctgagctt gggtcctgga ttctgtcagc cacttcaaat   2940
gagctagtct agcttccagc ttctgaacaa tccccggttt actcagtctc tcctaattcc   3000
agcctttcga acaactaata tcctgtcttc tctatcccta tgaaaaaac taacagagat    3060
cgatctgttt ccttgacacc atgaagtgcc ttttgtactt agcttttta ttcatcgggg     3120
tgaattgcaa gttcaccata gttttccac acaaccaaaa aggaaactgg aagacgttc      3180
cttccaatta ccattattgc ccgtcaagct cagatttaaa ttggcataat gacttaatag   3240
gcacagcctt acaagtcaaa atgcccaaga gtcacaaggc tattcaagca gacggttgga   3300
tgtgtcatgc ttccaaatgg gtcactactc tgtgatttcc gctggtacgga ccgaagtata   3360
taacacattc catccgatcc ttcactccat ctgtagaaca atgcaaggaa agcattgaac   3420
aaacgaaaca aggaacttgg ctgaatccag gcttcccctc tcaaagttgt ggatatgcaa   3480
ctgtgacgga tgctgaagca gcgattgtcc aggtgactcc tcaccatgtg cttgttgatg   3540
aatacacagg agaatgggtt gattcacagt tcatcaacgg aaaatgcagc aatgacatat   3600
gccccactgt ccataactcc acaacctggc attccgacta taaggtcaaa gggctatgtg   3660
attctaacct catttcatg gacatcacct tcttctcaga ggacgagag ctatcatccc     3720
taggaaagga gggcacaggg ttcagaagta actactttgc ttatgaaact ggagacaagg   3780
cctgcaaaat gcagtactgc aagcattggg gagtcagact cccatcaggt gtctggttcg   3840
agatggctga taaggatctc tttgctgcag ccagattccc tgaatgccca aagggtcaa    3900
gtatctctgc tccatctcag acctcagtgg atgtaagtct cattcaggac gttgagagga   3960
tcttggatta ttccctctgc caagaaacct ggagcaaaat cagagcgggt cttcccatct   4020
ctccagtgga tctcagctat cttgctccta aaaacccagg aaccggtcct gtcttttacca   4080
```

```
taatcaatgg tacectaaaa tactttgaga ccagatacat cagagtcgat attgctgctc  4140
caatcctctc aagaatggtc ggaatgatca gtggaactac cacagaaagg gaactgtggg  4200
atgactgggc tccatatgaa gacgtggaaa ttggacccaa tggagttctg aggaccagtt  4260
caggatataa gtttccttta tatatgattg gacatggtat gttggactcc gatcttcatc  4320
ttagctcaaa ggctcaggtg tttgaacatc ctcacattca agacgctgct tcgcagcttc  4380
ctgatgatga gactttattt tttggtgata ctgggctatc caaaaatcca atcgagtttg  4440
tagaaggttg gttcagtagt tggaagagct ctattgcctc ttttttcttt atcatagggt  4500
taatcattgg actattcttg gttctccgag ttggtattta tctttgcatt aaattaaagc  4560
acaccaagaa aagacagatt tatacagaca tagagatgaa ccgactttgga aagtaactca  4620
aatcctgcac aacagattct tcatgtttga accaaatcaa cttgtgatat catgctcaaa  4680
gaggccttaa ttaaattta attttttaatt tttatgaaaa aaactaacag caatcatgga  4740
agtccacgat tttgagaccg acgagttcaa tgatttcaat gaagatgact atgccacaag  4800
agaattcctg aatcccgatg agcgcatgac gtacttgaat catgctgatt acaatttgaa  4860
ttctcctcta attagtgatg atattgacaa tttgatcagg aaattcaatt ctcttccgat  4920
tccctcgatg tgggatagta agaactggga tggagttctt gagatgttaa catcatgtca  4980
agccaatccc atctcaacat ctcagatgca taaatggatg ggaagttggt taatgtctga  5040
taatcatgat gccagtcaag ggtatagttt tttacatgaa gtggacaaag aggcagaaat  5100
aacatttgac gtggtggaga cctteatecg cggctgggge aacaaaccaa ttgaatacat  5160
caaaaaggaa agatggactg actcattcaa aattctcgct tatttgtgtc aaaagttttt  5220
ggacttacac aagttgacat taatcttaaa tgctgtctct gaggtggaat tgctcaactt  5280
ggcgaggact ttcaaaggca aagtcagaag aagttctcat ggaacgaaca tatgcaggct  5340
tagggttccc agcttgggtc ctacttttat ttcagaagga tggcttact tcaagaaact  5400
tgatattcta atggaccgaa actttctgtt aatggtcaaa gatgtgatta tagggaggat  5460
gcaaacggtg ctatccatgg tatgtagaat agacaacctg ttctcagagc aagacatctt  5520
ctcccttcta aatatctaca gaattggaga taaaattgtg gagaggcagg gaaattttc  5580
ttatgcttg attaaaatgg tggaaccgat atgcaactg aagctgatga aattagcaag  5640
agaatcaagg cctttagtcc cacaattccc tcattttgaa aatcatatca agacttctgt  5700
tgatgaaggg gcaaaaattg accgaggtat aagattcctc catgatcaga taatgagtgt  5760
gaaaacagtg gatctcacac tggtgattta tggatcgttc agacattggg gtcatccttt  5820
tatagattat tacgctggac tagaaaaatt acattcccaa gtaaccatga agaaagatat  5880
tgatgtgtca tatgcaaaag cacttgcaag tgatttagct cggattgttc tatttcaaca  5940
gttcaatgat cataaaaagt ggttcgtgaa tggagacttg ctccctcatg atcatccctt  6000
taaaagtcat gttaaagaaa atacatggcc tacagctgct caagttcaag attttggaga  6060
taaatggcat gaacttccgc tgattaaatg ttttgaaata cccgacttac tagacccatc  6120
gataatatac tctgacaaaa gtcattcaat gaataggtca gaggtgttga aacatgtccg  6180
aatgaatccg aacactccta tccctagtaa aaaggtgttg cagactatgt tggacacaaa  6240
ggctaccaat tggaaagaat tcttaaaga gattgatgag aagggcttag atgatgatga  6300
tctaattatt ggtcttaaag gaaaggagag ggaactgaag ttggcaggta gattttctc  6360
cctaatgtct tggaaattgc gagaaatactt tgtaattacc gaatatttga taaagactca  6420
tttcgtccct atgtttaaag gcctgacaat ggcggacgat ctaactgcag tcattaaaaa  6480
gatgttagat tcctcatccg gccaaggatt gaagtcatat gaggcaattt gcatagccaa  6540
tcacattgat tacgaaaat ggaataacca ccaaggaag ttatcaaacg gcccagtgtt  6600
ccgagttatg ggccagttct taggttatcc atccttaatc gagagaactc atgaattttt  6660
tgagaaaagt cttatatact acaatggaag accagacttg atgcgtgttc acaacaacac  6720
actgatcaat tcaacctccc aacgagtttt ttggcaagga caagagggtg gactggaagg  6780
tctacgcaa aaaggatga gtatcctcaa tctactggtt attcaaagag aggctaaaat  6840
cagaaacact gctgtcaaag tcttggcaca aggtgataat caagttattt gcacacagta  6900
taaaacgaag aaatcgagaa acgttgtaga attacagggt gctctcaatc aaatggtttc  6960
taataatgag aaaattatga ctgcaatcaa aataggga gggaagttag acttttgat  7020
aaatgacgat gagactatgc aatctgcaga ttacttgaat tatggaaaaa taccgatttt  7080
ccgtgagtg attagagggt tagagaccaa gagatgctca cgagtgactt gtgtcaccaa  7140
tgaccaaata cccactgtg ctaatataat gagctcagtt tccacaaatg ctctcaccgt  7200
agctcattt gctgagaacc caatcaatgc catgatacag tacaattatt ttgggacatt  7260
tgctagactc ttgttgatga tgcatgatcc tgctcttcgt caatcattgt atgaagttca  7320
agataagata ccgggcttgc acagttctac tttcaaatac cgcatgttgt atttggaccc  7380
ttccattgga gggagtgtcgg gcatgtcttt gtccaggttt ttgattagag ccttcccaga  7440
tcccgtaaca gaaagtctct cattctggag attcatccat gtacatgctc gaagtgagca  7500
tctgaaggag atgagtgcag tatttggaaa ccccgagata gccaagttcc gaataactca  7560
catagacaag ctagtagaag atccaacctc tctgaacatc gctatgggaa tgagtccagc  7620
gaacttgtta aagactgagg ttaaaaaatg cttaatcgaa tcaagacaaa ccatcaggaa  7680
ccaggtgatt aaggatgcaa ccatatattt gtatcatgaa gaggatcggc tcagaagttt  7740
cttatggtca ataaatcctc tgttccccag attttaagt gaattcaaat caggcacttt  7800
tttggggagtc gcagacggc tcatcagtct atttcaaaat tctcgtacta ttcggaactc  7860
ctttaagaaa aagtatcata gggaattgga tgatttgatt gtgaggagtg aggtatcctg  7920
tttgacacat ttagggaaac ttcatttgag aaggggatca tgtaaaatgt ggacatgttc  7980
agctactcat gctgacacat taagataaca atcctgggc cgtacagtta ttgggacaac  8040
tgtacccca ccattagaaa tgttgggtcc acaacatcga aaagagactc cttgtgcacc  8100
atgtaacaca tcagggttca attatgtttc tgtgcattgt ccagacggga tccatgcgt  8160
ctttagttca cgggaccat tgcctgctta tctagggtct aaaacatctg aatctacatc  8220
tattttgcag ccttgggaaa gggaaagcaa agtcccactg attaaaagag ctacacgtct  8280
tagagatgct atctctcttgg ttgttgaacc cgactctaaa ctagcaatga ctatactttc  8340
taacatccac tcttttaacag gcgaagaatg gaccaaaagg cagcatgggt tcaaaagaac  8400
aggatctgcc cttcataggt tttcgacatc tcggatgagc catggtgggt tcgcatctca  8460
gagcactcga gcattgacca ggttgatggc aactacagac accatgaggt atcgggaga  8520
tcagaatttc gacttttat tccaagcaac gttgctctat gctcaaatta ccaccactgt  8580
tgcaagagac ggatggatca ccagttgtac agatcattat catattgcct gtaagtcctg  8640
tttgagaccc atagaagaga tcaccctgga ctcaagtatg gactacacgc ccccagatgt  8700
atcccatgtg ctgaagacat ggaggaatgg ggaaggttcg tggggacaag agataaaaca  8760
gatctatcct ttagaaggga attggaagaa tttagcaccct gctgagcaat cctatcaagt  8820
```

```
cggcagatgt ataggttttc tatatggaga cttggcgtat agaaaatcta ctcatgccga  8880
ggacagttct ctatttcctc tatctataca aggtcgtatt agaggtcgag gtttcttaaa  8940
agggttgcta gacggattaa tgagagcaag ttgctgccaa gtaatacacc ggagaagtct  9000
ggctcatttg aagaggccgg ccaacgcagt gtacggaggt ttgatttact tgattgataa  9060
attgagtgta tcacctccat tcctttctct tactagatca ggacctatta gagacgaatt  9120
agaaacgatt ccccacaaga tcccaacctc ctatccgaca agcaaccgtg atatgggggt  9180
gattgtcaga aattacttca aataccaatg ccgtctaatt gaaaagggaa aatacagatc  9240
acattattca caattatggt tattctcaga tgtcttatcc atagacttca ttggaccatt  9300
ctctatttcc accaccctct tgcaaatcct atacaagcca tttttatctg ggaaagataa  9360
gaatgagttg agagagctgg caaatctttc ttcattgcta agatcaggag aggggtggga  9420
agacatacat gtgaaattct tcaccaagga catattattg tgtccagagg aaatcagaca  9480
tgcttgcaag ttcgggattg ctaaggataa taataaagac atgagctatc ccccttgggg  9540
aagggaatcc agagggacaa ttacaacaat ccctgtttat tatacgacca ccccttaccc  9600
aaagatgcta gagatgcctc caagaatcca aaatcccctg ctgtccggaa tcaggttggg  9660
ccaattacca actggcgctc attataaaat tcggagtata ttacatggaa tgggaatcca  9720
ttacagggac ttcttgagtt gtggagacgg ctccggaggg atgactgctg cattactacg  9780
agaaaatgtg catagcagag gaatattcaa tagtctgtta gaattatcag ggtcagtcat  9840
gcgaggcgcc tctcctgagc cccccagtgc cctagaaact ttaggaggag ataaatcgag  9900
atgtgtaaat ggtgaaacat gttgggaata tccatctgac ttatgtgacc caaggacttg  9960
ggactatttc ctccgactca aagcaggctt ggggcttcaa attgatttaa ttgtaatgga 10020
tatggaagtt cgggattctt ctactagcct gaaaattgag acgaatgtta gaaattatgt 10080
gcaccggatt ttggatgagc aaggagtttt aatctacaag acttatggaa catatatttg 10140
tgagagcgaa aagaatgcag taacaatcct tggtcccatg ttcaagacgg tcgacttagt 10200
tcaaacagaa tttagtagtt ctcaaacgtc tgaagtatat atggtatgta aaggtttgaa 10260
gaaattaatc gatgaaccca atcccgattg gtcttccatc aatgaatcct ggaaaaacct 10320
gtacgcattc cagtcatcag aacaggaatt tgccagagca aagaaggtta gtacatactt 10380
taccttgaca ggtattccct cccaattcat tcctgatcct tttgtaaaca ttgagactat 10440
gctacaaata ttcggagtac ccacgggtgt gtctcatgcg gctgccttaa aatcatctga 10500
tagacctgca gatttattga ccattagcct ttttttatatg gcgattatat cgtattataa 10560
catcaatcat atcagagtag gaccgatacc tccgaacccc ccatcagatg gaattgcaca 10620
aaatgtgggg atcgctataa ctggtataag cttttggctg agtttgatgg agaaagacat 10680
tccactatat caacagtgtt tagcagttat ccagcaatca ttcccgatta ggtgggaggc 10740
tgtttcagta aaaggaggat acaagcagaa gtggagtact agaggtgatg ggctcccaaa 10800
agatacccga atttcagact ccttggcccc aatcgggaac tggatcagat ctctggaatt 10860
ggtccgaaac caagttcgtc taaatccatt caatgagatc ttgttcaatc agctatgtcg 10920
tacagtggat aatcatttga aatggtcaaa tttgcgaaaa aacacaggaa tgattgaatg 10980
gatcaataga cgaatttcaa aagaagaccg gtctatactg atgttgaaga gtgacctaca 11040
cgaggaaaac tcttggagag attaaaaaat catgaggaga ctccaaactt taagtatgaa 11100
aaaaactttg atccttaaga ccctcttgtg gtttttattt tttatctggt tttgtggtct 11160
tcgt                                                             11164

SEQ ID NO: 18         moltype =   length =
SEQUENCE: 18
000
```